United States Patent
Kho et al.

(10) Patent No.: US 9,515,265 B2
(45) Date of Patent: Dec. 6, 2016

(54) ORGANIC LIGHT-EMITTING DEVICE

(71) Applicant: SAMSUNG DISPLAY CO., LTD., Yongin, Gyeongg-Do (KR)

(72) Inventors: Sam-Il Kho, Yongin (KR); Hyoung-Kun Kim, Yongin (KR); Mi-Kyung Kim, Yongin (KR); Hwan-Hee Cho, Yongin (KR)

(73) Assignee: SAMSUNG DISPLAY CO., LTD., Yongin, Gyeonggi-Do (KR)

(*) Notice: Subject to any disclaimer, the term of this patent is extended or adjusted under 35 U.S.C. 154(b) by 365 days.

(21) Appl. No.: 14/291,516

(22) Filed: May 30, 2014

(65) Prior Publication Data
US 2015/0053942 A1 Feb. 26, 2015

(30) Foreign Application Priority Data
Aug. 23, 2013 (KR) .................. 10-2013-0100564

(51) Int. Cl.
*H01L 51/50* (2006.01)
*H01L 51/00* (2006.01)
*C07C 211/61* (2006.01)
*C07D 209/82* (2006.01)

(52) U.S. Cl.
CPC ......... *H01L 51/0052* (2013.01); *C07C 211/61* (2013.01); *C07D 209/82* (2013.01); *H01L51/006* (2013.01); *H01L 51/0059* (2013.01); *H01L 51/0072* (2013.01); *H01L 51/506* (2013.01); *H01L 51/5064* (2013.01)

(58) Field of Classification Search
None
See application file for complete search history.

(56) References Cited

U.S. PATENT DOCUMENTS

| | | | |
|---|---|---|---|
| 2007/0278938 A1 | 12/2007 | Yabunouchi et al. | |
| 2013/0140530 A1* | 6/2013 | Kho | H01L 51/006 257/40 |
| 2014/0061630 A1 | 3/2014 | Yabunouchi et al. | |
| 2014/0252327 A1 | 9/2014 | Cho et al. | |
| 2014/0374722 A1* | 12/2014 | Kim | C07D 209/08 257/40 |

FOREIGN PATENT DOCUMENTS

| | | |
|---|---|---|
| KR | 10-2013-0062103 A | 6/2013 |
| KR | 10-2014-0109179 A | 9/2014 |
| WO | WO 2007/125714 A1 | 11/2007 |
| WO | WO 2009/145016 A1 | 12/2009 |

* cited by examiner

*Primary Examiner* — Gregory Clark
(74) *Attorney, Agent, or Firm* — Lee & Morse, P.C.

(57) ABSTRACT

Provided is an organic light-emitting device, including a first electrode; a second electrode facing the first electrode; an emission layer disposed between the first electrode and the second electrode; a first hole transport layer that is disposed between the emission layer and the first electrode and includes a first compound and a first charge-generation material; a second hole transport layer that is disposed between the emission layer and the first hole transport layer and includes a second compound; a third hole transport layer that is disposed between the emission layer and the second hole transport layer and includes a third compound and a second charge-generation material; and a fourth hole transport layer that is disposed between the emission layer and the third hole transport layer and includes a fourth compound. The first, second, third, and fourth compounds are each represented by Formula 1 or 2:

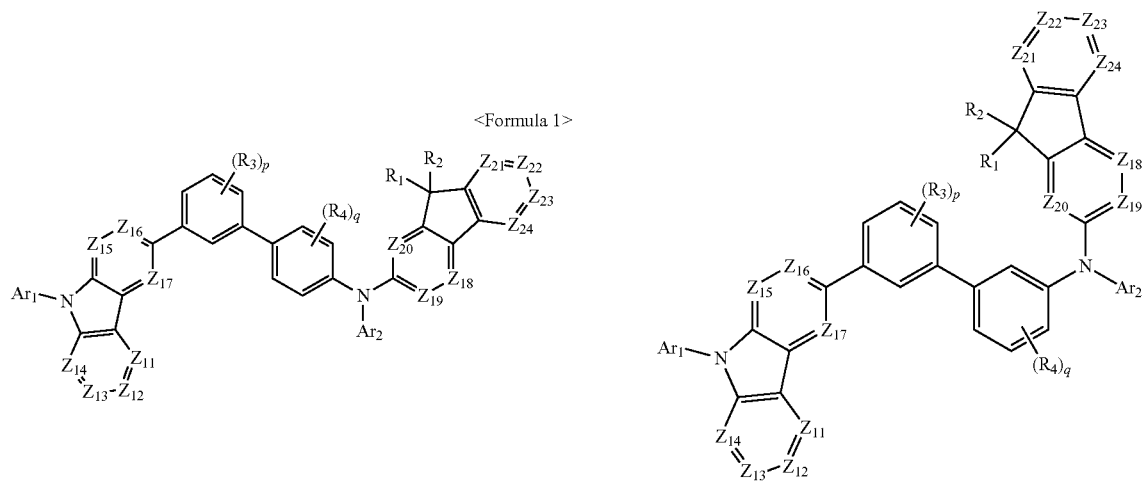
20 Claims, 2 Drawing Sheets

ORGANIC LIGHT-EMITTING DEVICE

CROSS-REFERENCE TO RELATED APPLICATION

Korean Patent Application No. 10-2013-0100564, filed on Aug. 23, 2013, in the Korean Intellectual Property Office, and entitled: "Organic Light-Emitting Device," is incorporated by reference herein in its entirety.

BACKGROUND

1. Field

Embodiments relates to an organic light-emitting device, for example, an organic light-emitting device including a plurality of hole transport layers including materials that may have different hole transport characteristics, electrical stability, and charge-generation characteristics.

2. Description of the Related Art

Organic light emitting devices are self-emission devices that may have wide viewing angles, high contrast ratios, short response time, and excellent brightness, driving voltage, and response speed characteristics, and produce full-color images.

SUMMARY

Embodiments may be realized by providing an organic light-emitting device, including a first electrode; a second electrode facing the first electrode; an emission layer disposed between the first electrode and the second electrode; a first hole transport layer that is disposed between the emission layer and the first electrode and includes a first compound and a first charge-generation material; a second hole transport layer that is disposed between the emission layer and the first hole transport layer and includes a second compound; a third hole transport layer that is disposed between the emission layer and the second hole transport layer and includes a third compound and a second charge-generation material; and a fourth hole transport layer that is disposed between the emission layer and the third hole transport layer and includes a fourth compound. The first compound, the second compound, the third compound, and the fourth compound are each independently a compound represented by Formula 1 or 2:

<Formula 1>

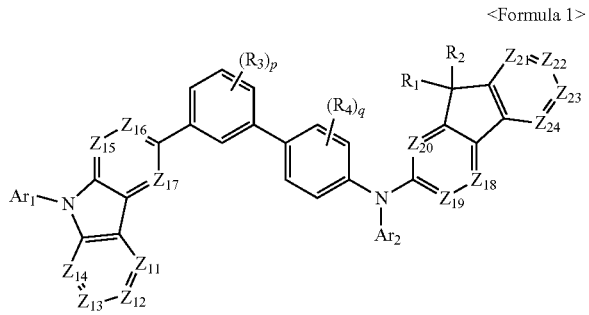

<Formula 2>

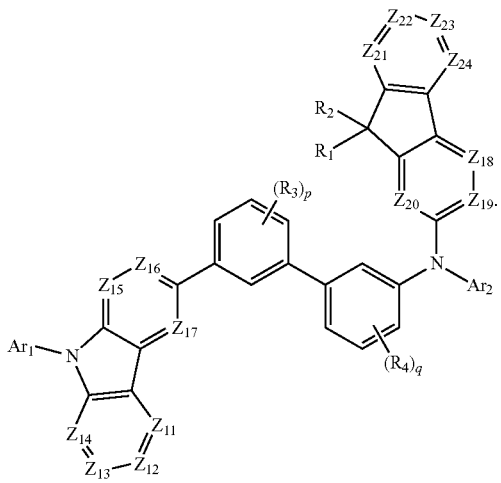

In Formulae 1 and 2,
$Z_{11}$ is N or $C(R_{11})$, $Z_{12}$ is N or $C(R_{12})$, $Z_{13}$ is N or $C(R_{13})$, $Z_{14}$ is N or $C(R_{14})$, $Z_{15}$ is N or $C(R_{15})$, $Z_{16}$ is N or $C(R_{16})$, $Z_{17}$ is N or $C(R_{17})$, $Z_{18}$ is N or $C(R_{18})$, $Z_{19}$ is N or $C(R_{19})$, $Z_{20}$ is N or $C(R_{20})$, $Z_{21}$ is N or $C(R_{21})$, $Z_{22}$ is N or $C(R_{22})$, $Z_{23}$ is N or $C(R_{23})$, and $Z_{24}$ is N or $C(R_{24})$.

$Ar_1$ and $Ar_2$ are each independently selected from:
a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group; and
a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group, each substituted with at least one selected from a deuterium, a halogen atom, a hydroxyl group, a cyano group, a nitro group, an amino group, an amidino group, a hydrazine group, a hydrazone group, a carboxyl group and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_2$-$C_{60}$ aryloxy group, a $C_6$-$C_{60}$ arylthio group, and a $C_2$-$C_{60}$ heteroaryl group.

$R_1$ and $R_2$ are each independently selected from:
a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;
a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group; and a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group, each substituted with at least one selected from a deuterium, a halogen atom, a hydroxyl group, a cyano group, a nitro group, an amino group, an amidino group, a hydrazine group, a hydrazone group, a carboxyl group and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_2$-$C_{60}$ aryloxy group, a $C_6$-$C_{60}$ arylthio group, and a $C_2$-$C_{60}$ heteroaryl group.

$R_3$, $R_4$, and $R_{11}$ to $R_{24}$ are each independently selected from:

a hydrogen, a deuterium, a halogen atom, a hydroxyl group, a cyano group, a nitro group, an amino group, an amidino group, a hydrazine group, a hydrazone group, a carboxyl group and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group, each substituted with at least one selected from a deuterium, a halogen atom, a hydroxyl group, a cyano group, a nitro group, an amino group, an amidino group, a hydrazine group, a hydrazone group, a carboxyl group and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_2$-$C_{60}$ aryloxy group, a $C_6$-$C_{60}$ arylthio group, and a $C_2$-$C_{60}$ heteroaryl group; and —$N(Q_{11})(Q_{12})$, —$Si(Q_{13})(Q_{14})(Q_{15})$, and —$B(Q_{16})(Q_{17})$ (wherein $Q_{11}$ to $Q_{17}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group).

p and q are each independently an integer of 1 to 4.

Embodiments may be realized by providing an organic light-emitting device, including a first electrode; a second electrode facing the first electrode; an emission layer disposed between the first electrode and the second electrode; a first hole transport layer that is disposed between the emission layer and the first electrode and includes a first compound and a first charge-generation material; a second hole transport layer that is disposed between the emission layer and the first hole transport layer and includes a second compound; a third hole transport layer that is disposed between the emission layer and the second hole transport layer and includes a third compound and a second charge-generation material; and a fourth hole transport layer that is disposed between the emission layer and the third hole transport layer and includes a fourth compound. The first compound, the second compound, the third compound, and the fourth compound are each independently a compound represented by Formula 1A or 2A:

<Formula 1A>

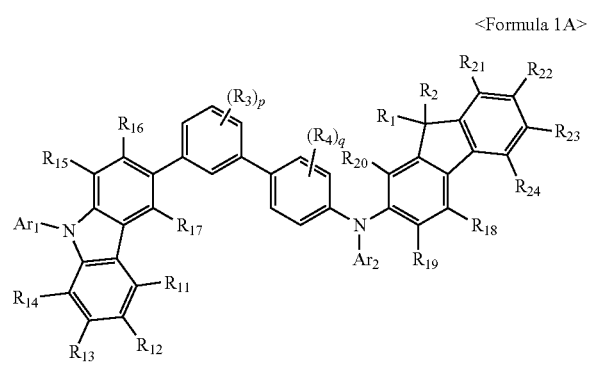

<Formula 2A>

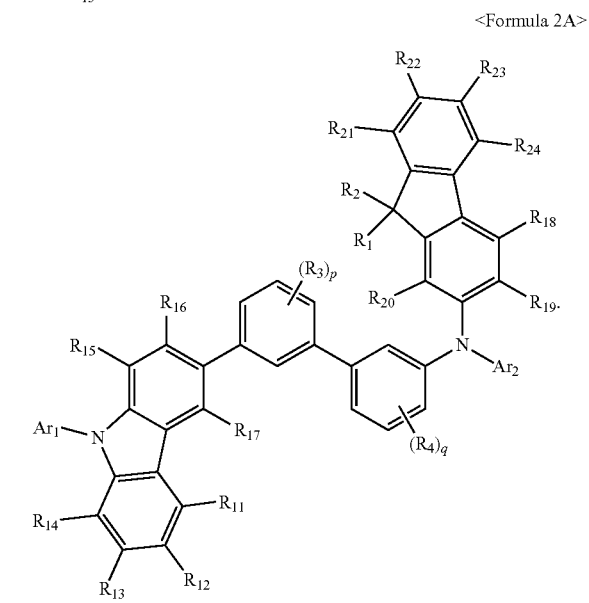

In Formulae 1A and 2A, $Ar_1$, $Ar_2$, $R_1$ to $R_4$, $R_{11}$ to $R_{24}$, p and q may each independently be the same as groups defined for Formula 1 or Formula 2.

In an embodiment, $Ar_1$ and $Ar_2$ are each independently represented by one of Formulae 3-1 to 3-20:

3-1

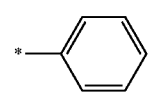

3-2

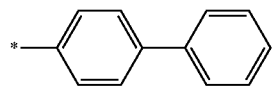

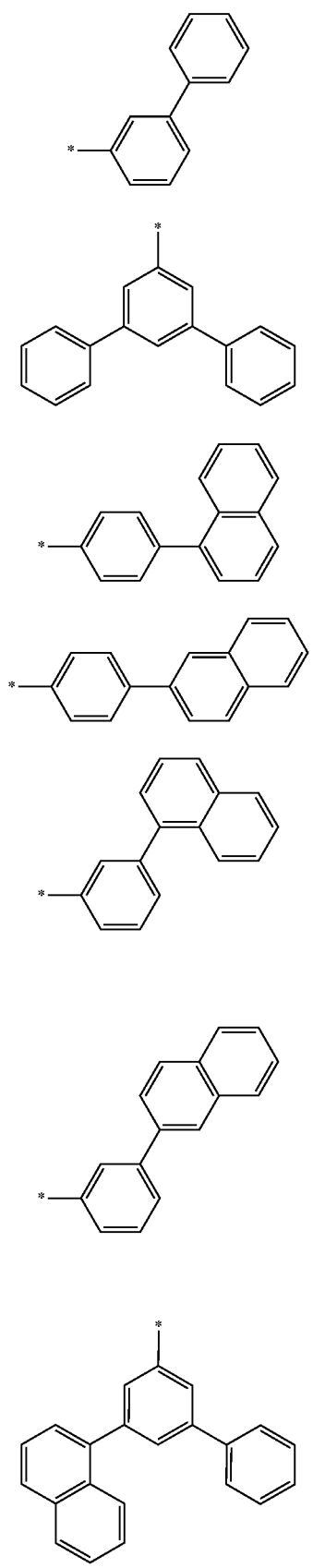
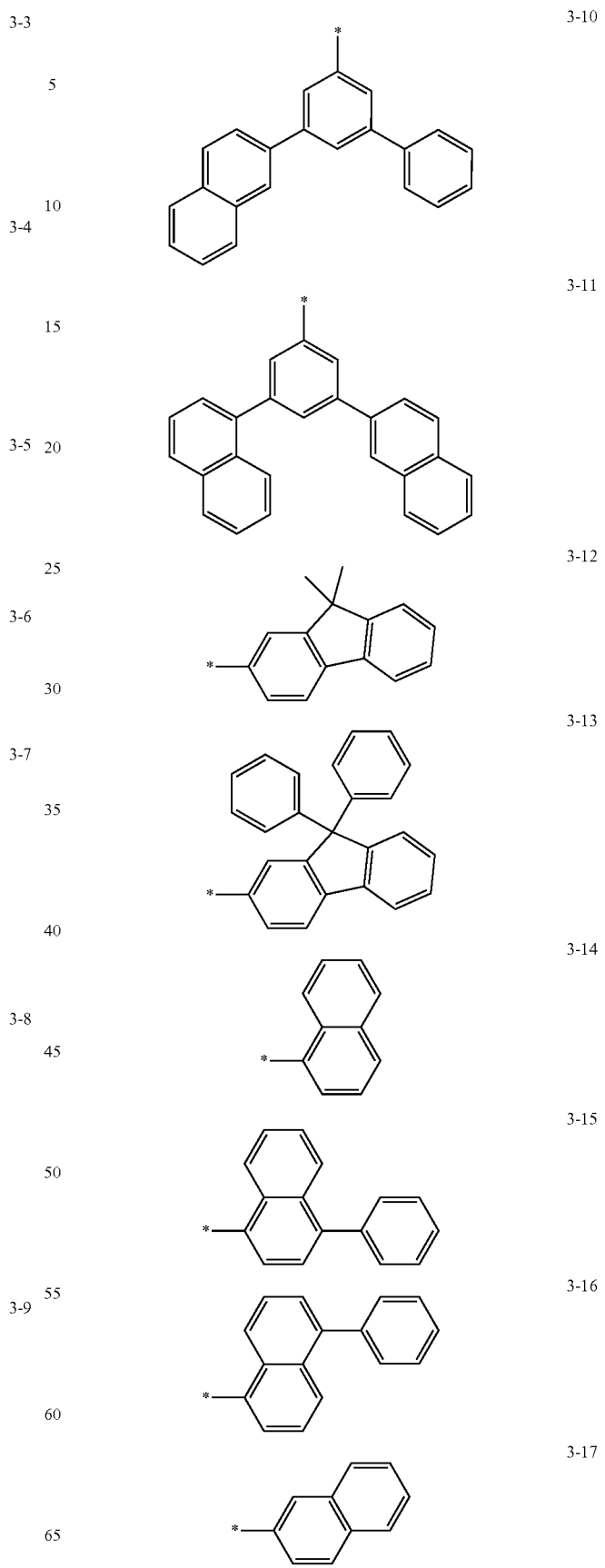

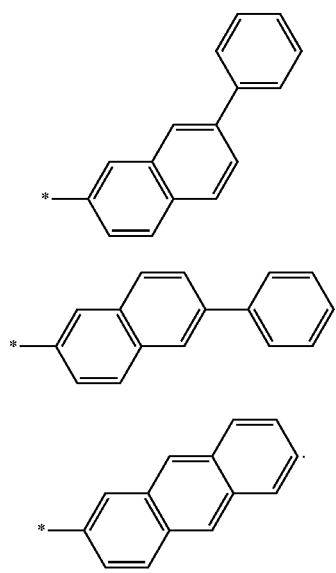
3-18
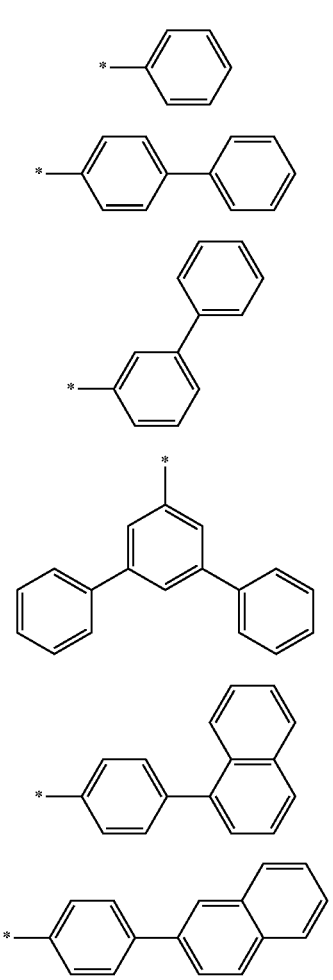
3-19
3-20
R$_1$ and R$_2$ are each independently a C$_1$-C$_{20}$ alkyl group or a group represented by Formula 3-1 to 3-20:
3-1
3-2
3-3
3-4
3-5
3-6
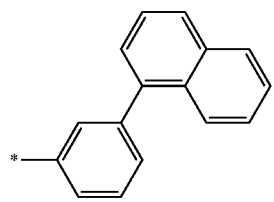
3-7
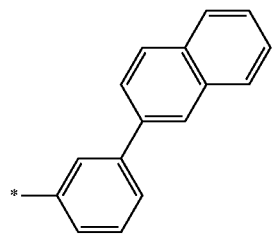
3-8
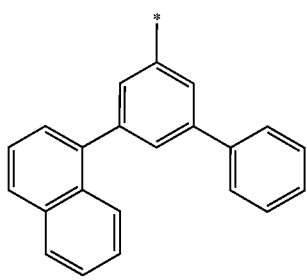
3-9
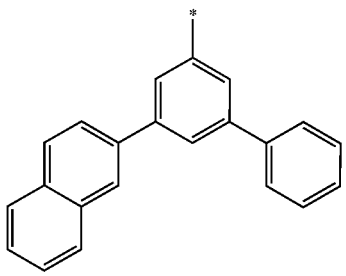
3-10
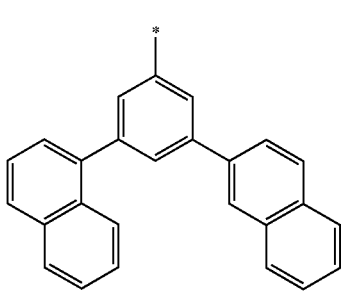
3-11
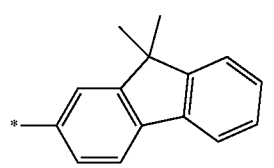
3-12

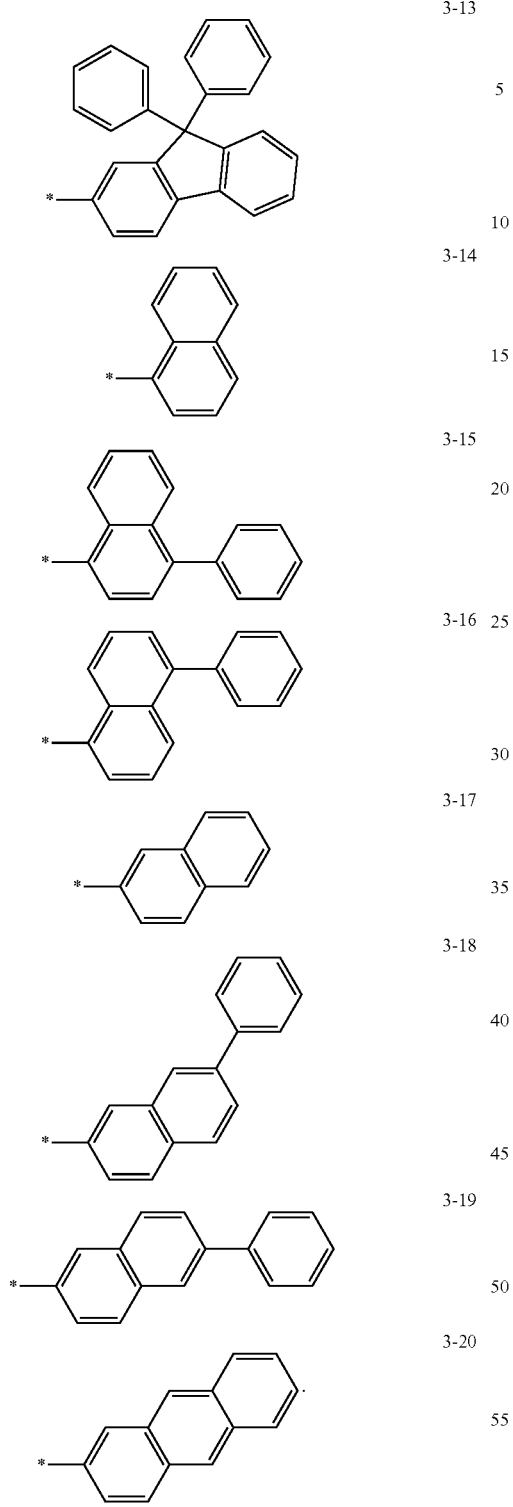

$R_3$, $R_4$ and $R_{11}$ to $R_{24}$ are each independently a hydrogen, a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, or a group represented by Formulae 3-1 to 3-20:

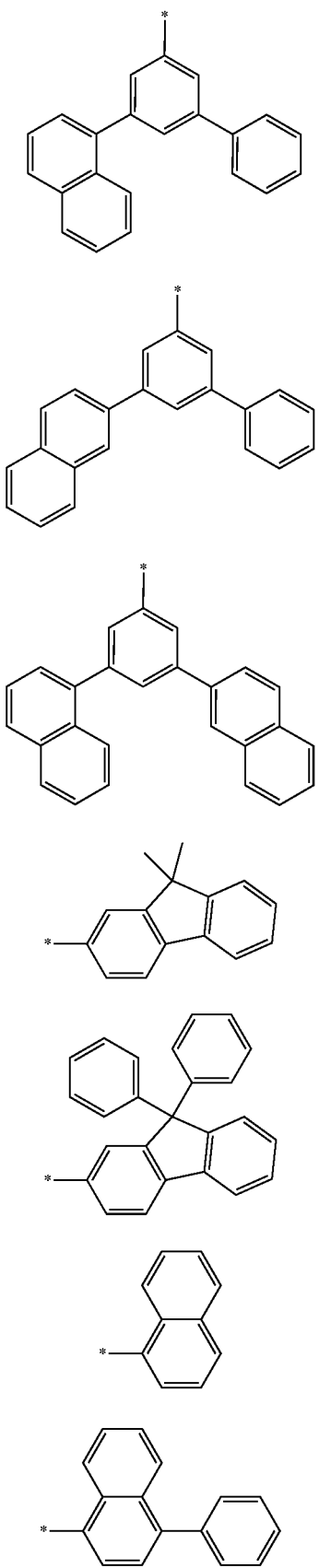

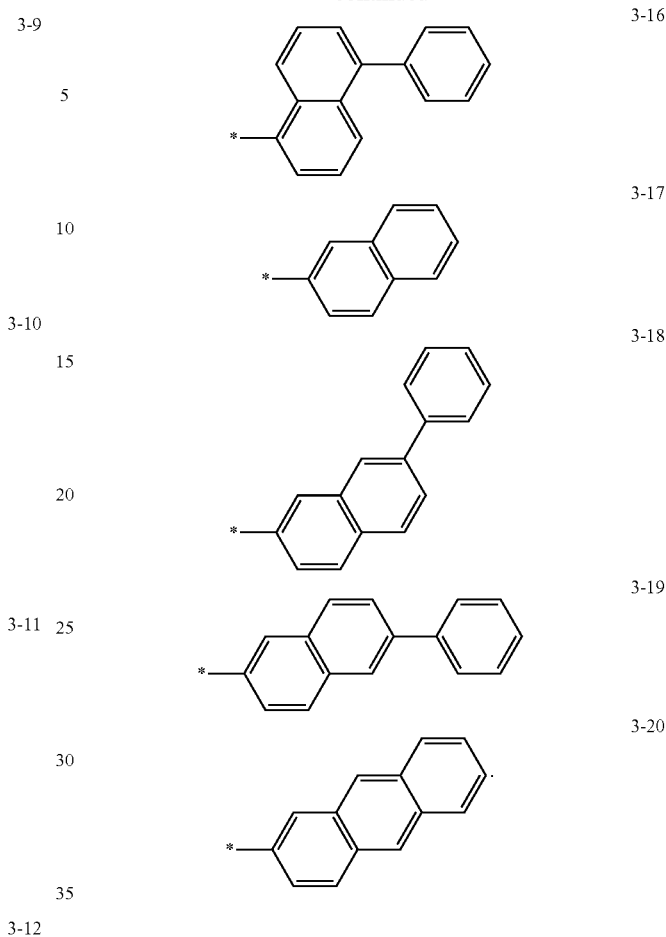

p and q are each independently an integer of 1 to 4.

BRIEF DESCRIPTION OF THE DRAWINGS

Features will become apparent to those of skill in the art by describing in detail exemplary embodiments with reference to the attached drawings in which.

These and/or other aspects will become apparent and more readily appreciated from the following description of the embodiments, taken in conjunction with the accompanying drawings in which.

DETAILED DESCRIPTION

Figure 1:
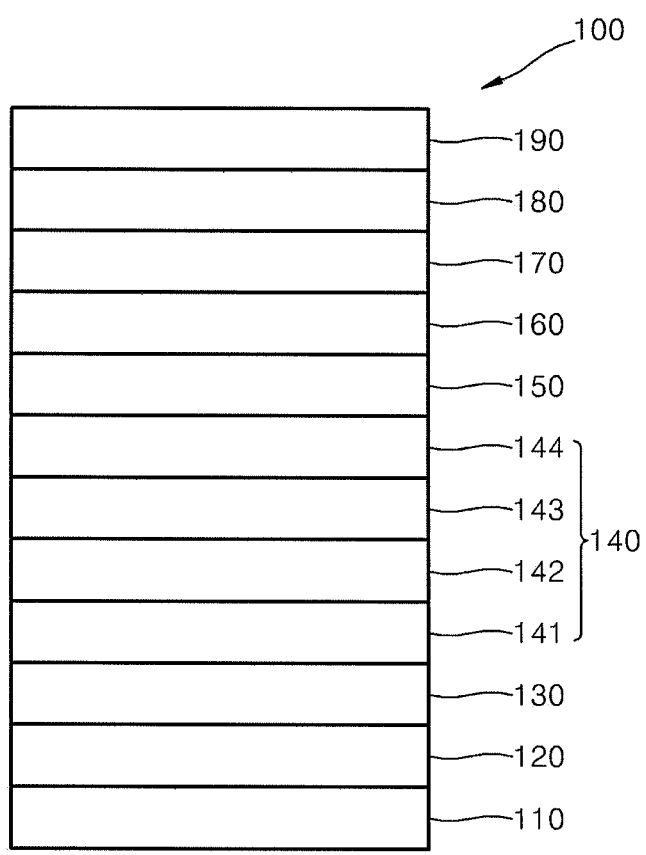
FIG. 1 illustrates a schematic cross-sectional view of an organic light-emitting device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Expressions such as "at least one of," when preceding a list of elements, modify the entire list of elements and do not modify the individual elements of the list.

The term "organic layer" used herein refers to a single layer and/or a plurality of layers disposed between the first electrode and the second electrode of an organic light-emitting device.

FIG. 1 illustrates a schematic view of an organic light-emitting diode 100 according to an embodiment. Hereinafter, the structure of an organic light-emitting device according to an embodiment and a method of manufacturing an organic light-emitting device according to an embodiment will be described in connection with FIG. 1.

The organic light-emitting device 100 includes a substrate 110, a first electrode 120, a hole injection layer 130, a first hole transport layer 141, a second hole transport layer 142, a third hole transport layer 143, a fourth hole transport layer 144, a buffer layer 150, an emission layer 160, an electron transport layer 170, an electron injection layer 180, and a second electrode 190.

For use as the substrate 110, any substrate that can be used in an organic light-emitting device may be used. For example, the substrate 110 may be a glass substrate or transparent plastic substrate, each with excellent mechanical strength, thermal stability, transparency, surface smoothness, ease of handling, and water repellency.

The first electrode 120 may be formed by, for example, depositing or sputtering a material for a first electrode on the substrate 110. The first electrode 120 may be an anode, and the material for the first electrode may be selected from materials with a high work function to make holes be easily injected. The first electrode 120 may be a reflective electrode or a transmissive electrode. The material for the first electrode 120 may be a transparent and highly conductive material, and examples of such a material are indium tin oxide (ITO), indium zinc oxide (IZO), tin oxide ($SnO_2$), and zinc oxide (ZnO). According to an embodiment, magnesium (Mg), aluminum (Al), aluminum-lithium (Al—Li), calcium (Ca), magnesium-indium (Mg—In), or magnesium-silver (Mg—Ag) may be used, and the first electrode 120 may be formed as a reflective electrode.

The first electrode 120 may have a single-layer structure, or a multi-layer structure including two or more layers. For example, the first electrode 120 may have a multi-layer structure including two different materials. For example, the first electrode 120 may have a three-layered structure of ITO/Ag/ITO.

The hole injection layer 130 is disposed on the first electrode 120. According to purpose, the hole injection layer 130 may not be formed.

The hole injection layer (HIL) 130 may be formed on the first electrode 120 by using various methods, such as vacuum deposition, spin coating, casting, or langmuir-blodgett (LB).

When a hole injection layer 130 is formed by vacuum deposition, the deposition conditions may vary according to a material that is used to form the hole injection layer 130, and the structure and thermal characteristics of the hole injection layer 130. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the hole injection layer 130 is formed by spin coating, coating conditions may vary according to the material used to form the hole injection layer 130, and the structure and thermal properties of the hole injection layer 130. For example, a coating speed may be from about 2000 rpm to about 5000 rpm, and a temperature at which a heat treatment is performed to remove a solvent after coating may be from about 80° C. to about 200° C.

Exemplary materials for forming the hole injection layer 130 include N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine (NPB), 4,4',4''-tris(N,N-diphenylamino)triphenylamine (TDATA), 4,4',4''-tris[2-naphthyl(phenyl)amino]triphenylamine (2-TNATA), polyaniline/dodecylbenzenesulfonic acid (PANI/DBSA), poly(3,4-ethylenedioxythiophene)/poly (4-styrenesulfonate) (PEDOT/PSS), polyaniline/camphor sulfonicacid (PANI/CSA), and (polyaniline)/poly(4-styrenesulfonate) (PANI/PSS):

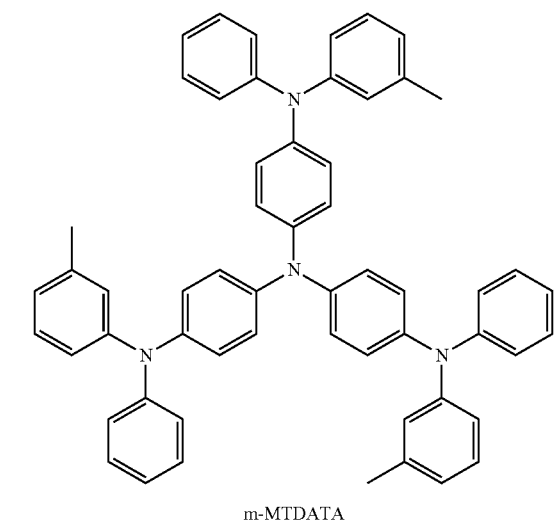

m-MTDATA

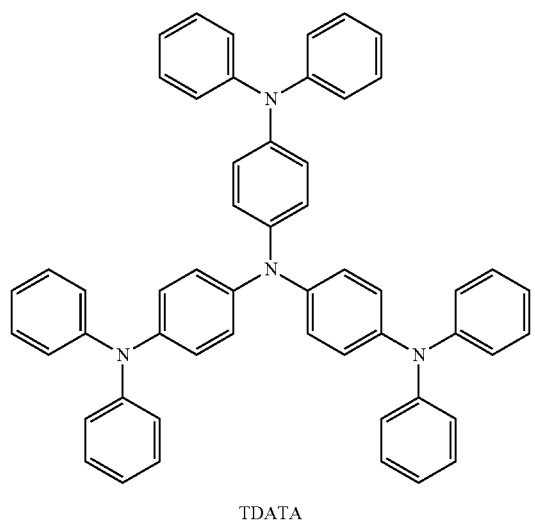

TDATA

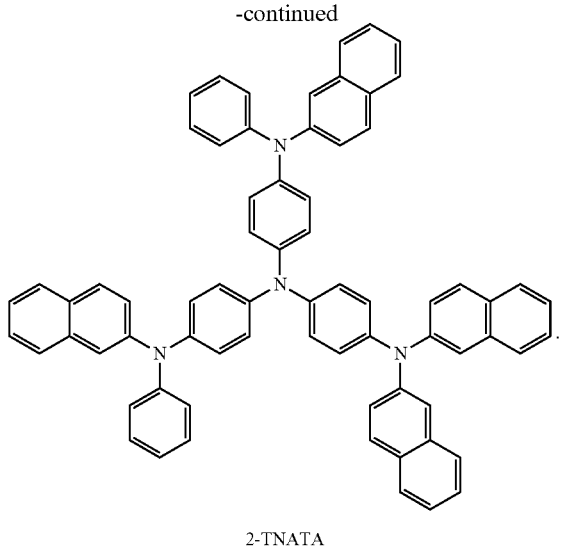

2-TNATA

A thickness of the hole injection layer 130 may be in a range of about 100 Å to about 10,000 Å, for example, about 100 Å to about 1000 Å. Maintaining the thickness of the hole injection layer 130 within the range described above may help provide the hole injection layer 130 with satisfactory hole injection characteristics without a substantial increase in a driving voltage.

Then, the hole transport layer 140 may be formed on the hole injection layer 130. The hole transport layer 140 may include the first hole transport layer 141, the second hole transport layer 142, the third hole transport layer 143, and the fourth hole transport layer 144, which are sequentially stacked in this stated order.

First, the first hole transport layer 141 may be formed on the hole injection layer 130 by using various methods, such as vacuum deposition, spin coating, casting, or a LB method. When the first hole transport layer 141 is formed using vacuum deposition or spin coating, the deposition and coating conditions may be similar to those for the formation of the hole injection layer 130, though the deposition and coating conditions may vary according to a compound that is used to form the first hole transport layer 141.

As a material for forming the first hole transport layer 141, a first compound that is doped with a first charge-generation material may be used. An amount of the first charge-generation material may be in a range of about 0.01 to about 3 wt % based on 100 wt % of the first hole transport layer 141. For example, an amount of the first charge-generation material may be in a range of about 1 to about 2 wt % based on 100 wt % of the first hole transport layer. The first charge-generation material is a material that generates charges and may be homogeneously or non-homogeneously dispersed in the first hole transport layer 141. Maintaining the amount of the first charge-generation material within these ranges may help generate an appropriate amount of charge in the first hole transport layer 141.

A thickness of the first hole transport layer 141 may be in a range of about 5 nm to about 30 nm. For example, a thickness of the first hole transport layer 141 may be in a range of about 8 nm to about 12 nm. Maintaining the thickness of the first hole transport layer 141 within these ranges may help provide satisfactory hole transport characteristics and an appropriate amount of charge without a substantial increase in driving voltage.

First, the second hole transport layer 142 may be formed on the first hole transport layer 141 by using various methods, such as vacuum deposition, spin coating, casting, or a LB method. When the second hole transport layer 142 is formed using vacuum deposition or spin coating, the deposition and coating conditions may be similar to those for the formation of the hole injection layer 130, though the deposition and coating conditions may vary according to a compound that is used to form the second hole transport layer 142.

As a material for forming the second hole transport layer 142, a second compound may be used.

A thickness of the first hole transport layer 142 may be in a range of about 60 nm to about 100 nm. For example, a thickness of the second hole transport layer 142 may be in a range of about 60 nm to about 80 nm. Maintaining the thickness of the second hole transport layer 142 within these ranges may help provide satisfactory hole transport characteristics and hole mobility without a substantial increase in driving voltage.

First, the third hole transport layer 143 may be formed on the second hole transport layer 142 by using various methods, such as vacuum deposition, spin coating, casting, or a LB method. When the third hole transport layer 143 is formed using vacuum deposition or spin coating, the deposition and coating conditions may be similar to those for the formation of the hole injection layer 130, though the deposition and coating conditions may vary according to a compound that is used to form the third hole transport layer 143.

As a material for forming the third hole transport layer 143, a third compound that is doped with a second charge-generation material may be used. An amount of the second charge-generation material may be in a range of about 0.01 to about 3 wt % based on 100 wt % of the third hole transport layer 143. For example, an amount of the second charge-generation material may be in a range of about 1 to about 2 wt % based on 100 wt % of the third hole transport layer 143. The second charge-generation material is a material that generates charges and may be homogeneously or non-homogeneously dispersed in the third hole transport layer 143. Maintaining the amount of the second charge-generation material within these ranges may help generate an appropriate amount of charge in the third hole transport layer 143.

A thickness of the third hole transport layer 143 may be in a range of about 5 nm to about 30 nm. For example, a thickness of the third hole transport layer 143 may be in a range of about 8 nm to about 12 nm. Maintaining the thickness of the third hole transport layer 143 within these ranges may help provide satisfactory hole transport characteristics and an appropriate intensity of charge without a substantial increase in driving voltage.

First, the fourth hole transport layer 144 may be formed on the third hole transport layer 143 by using various methods, such as vacuum deposition, spin coating, casting, or a LB method. When the fourth hole transport layer 144 is formed using vacuum deposition or spin coating, the deposition and coating conditions may be similar to those for the formation of the hole injection layer 130, though the deposition and coating conditions may vary according to a compound that is used to form the fourth hole transport layer 144.

As a material for forming the fourth hole transport layer 144, a fourth compound may be used.

A thickness of the fourth hole transport layer 144 may be in a range of about 60 nm to about 100 nm. For example, a thickness of the fourth hole transport layer 144 may be in a range of about 50 nm to about 60 nm. Maintaining the thickness of the fourth hole transport layer 144 within these ranges may help provide satisfactory hole transport characteristics and hole mobility without a substantial increase in driving voltage.

The first compound, the second compound, the third compound, and the fourth compound may each independently be a compound represented by Formula 1 or 2 below:

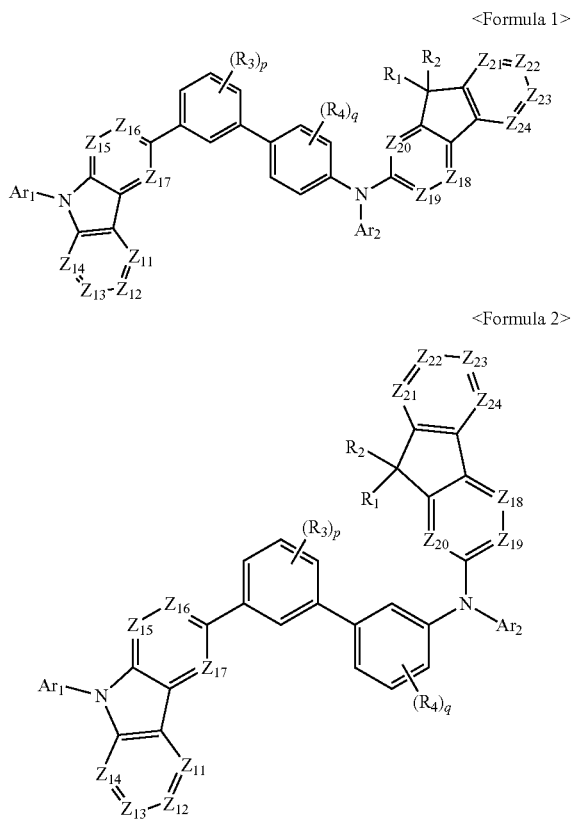

<Formula 1>

<Formula 2> wherein in Formulae 1 and 2, $Z_{11}$ is N or $C(R_{11})$, $Z_{12}$ is N or $C(R_{12})$, $Z_{13}$ is N or $C(R_{13})$, $Z_{14}$ is N or $(R_{14})$, $Z_{15}$ is N or $C(R_{15})$, $Z_{16}$ is N or $C(R_{16})$, $Z_{17}$ is N or $C(R_{17})$, $Z_{18}$ is N or $C(R_{18})$, $Z_{19}$ is N or $C(R_{19})$, $Z_{20}$ is N or $C(R_{20})$, $Z_{21}$ is N or $C(R_{21})$, $Z_{22}$ is N or $C(R_{22})$, $Z_{23}$ is N or $C(R_{23})$, and $Z_{24}$ is N or $C(R_{24})$;

$Ar_1$ and $Ar_2$ are each independently selected from a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group, each substituted with at least one selected from a deuterium, a halogen atom, a hydroxyl group, a cyano group, a nitro group, an amino group, an amidino group, a hydrazine group, a hydrazone group, a carboxyl group and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_2$-$C_{60}$ aryloxy group, a $C_6$-$C_{60}$ arylthio group, and a $C_2$-$C_{60}$ heteroaryl group; and $R_1$ and $R_2$ are each independently selected from a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group, each substituted with at least one selected from a deuterium, a halogen atom, a hydroxyl group, a cyano group, a nitro group, an amino group, an amidino group, a hydrazine group, a hydrazone group, a carboxyl group and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_2$-$C_{60}$ aryloxy group, a $C_6$-$C_{60}$ arylthio group, and a $C_2$-$C_{60}$ heteroaryl group; and $R_3$, $R_4$, and $R_{11}$ to $R_{24}$ may each independently be selected from a hydrogen, a deuterium, a halogen atom, a hydroxyl group, a cyano group, a nitro group, an amino group, an amidino group, a hydrazine group, a hydrazone group, a carboxyl group and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group, each substituted with at least one selected from a deuterium, a halogen atom, a hydroxyl group, a cyano group, a nitro group, an amino group, an amidino group, a hydrazine group, a hydrazone group, a carboxyl group and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_2$-$C_{60}$ aryloxy group, a $C_6$-$C_{60}$ arylthio group, and a $C_2$-$C_{60}$ heteroaryl group; and —$N(Q_{11})(Q_{12})$, —$Si(Q_{13})(Q_{14})(Q_{15})$, and —$B(Q_{16})(Q_{17})$ (wherein $Q_{11}$ to $Q_{17}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group); and p and q are each independently an integer of 1 to 4.

For example, in Formulae 1 and 2, $Z_{11}$ is $C(R_{11})$, $Z_{12}$ is $C(R_{12})$, $Z_{13}$ is $C(R_{13})$, $Z_{14}$ is $C(R_{14})$, $Z_{15}$ is $C(R_{15})$, $Z_{16}$ is $C(R_{16})$, $Z_{17}$ is $C(R_{17})$, $Z_{18}$ is $C(R_{18})$, $Z_{19}$ is $C(R_{19})$, $Z_{20}$ is $C(R_{20})$, $Z_{21}$ is $C(R_{21})$, $Z_{22}$ is $C(R_{22})$, $Z_{23}$ is $C(R_{23})$, and $Z_{24}$ is $C(R_{24})$.

For example, $Ar_1$ and $Ar_2$ in Formulae 1 and 2 may each independently be selected from i) a phenyl group, a pentalenyl group, an indenyl group, a naphthyl group group, an azulenyl group, an indacenyl group, an acenaphtyl group, a fluorenyl group, a spiro-fluorenyl group, a phenalenyl group, a phenanthrenyl group, an anthryl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, a dibenzofuranyl group, a dibenzothiophenyl group, and a benzocarbazolyl group; and a phenyl group, a pentalenyl group, an indenyl group, a naphthyl group, an azulenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, a indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, a isothiazolyl group, a benzothiazolyl group, an isooxazolyl group, an oxazolyl group, a triazolyl group, a tetrazolyl group, a oxadiazolyl group, a triazinyl group, a benzooxazolyl group, a dibenzofuranyl group, a dibenzothiophenyl group, and a benzocarbazolyl group, a each substituted with at least one selected from deuterium, a halogen atom, a hydroxyl group, a cyano group, a nitro group, an amino group, an amidino group, a hydrazine, a hydrazone, a carboxyl group and a salt thereof, a sulfonic acid and a salt thereof, a phosphoric acid and a salt thereof, a $C_1$-$C_{20}$ alkyl group, a $C_1$-$C_{20}$ alkoxy group, a $C_6$-$C_{20}$ aryl group, and a $C_2$-$C_{20}$ heteroaryl group.

For example, $Ar_1$ and $Ar_2$ in Formulae 1 and 2 may each independently be selected from i) a phenyl group, a pentalenyl group, an indenyl group, a naphtyl group, an azulenyl group, an indacenyl group, an acenaphtyl group, a fluorenyl group, a spiro-fluorenyl group, a phenalenyl group, a phenanthrenyl group, an anthryl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, a dibenzofuranyl group, a dibenzothiophenyl group, and a benzocarbazolyl group; and ii) a phenyl group, a pentalenyl group, an indenyl group, a naphtyl group, an azulenyl group, an indacenyl group, an acenaphtyl group, a fluorenyl group, a spiro-fluorenyl group, a phenalenyl group, a phenanthrenyl group, an anthryl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, a dibenzofuranyl group, a dibenzothiophenyl group, and a benzocarbazolyl group, each substituted with at least one selected from a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, and a $C_2$-$C_{20}$ heteroaryl group For example, $Ar_1$ and $Ar_2$ in Formulae 1 and 2 may each independently be represented by one of Formulae 3-1 to 3-20 below:

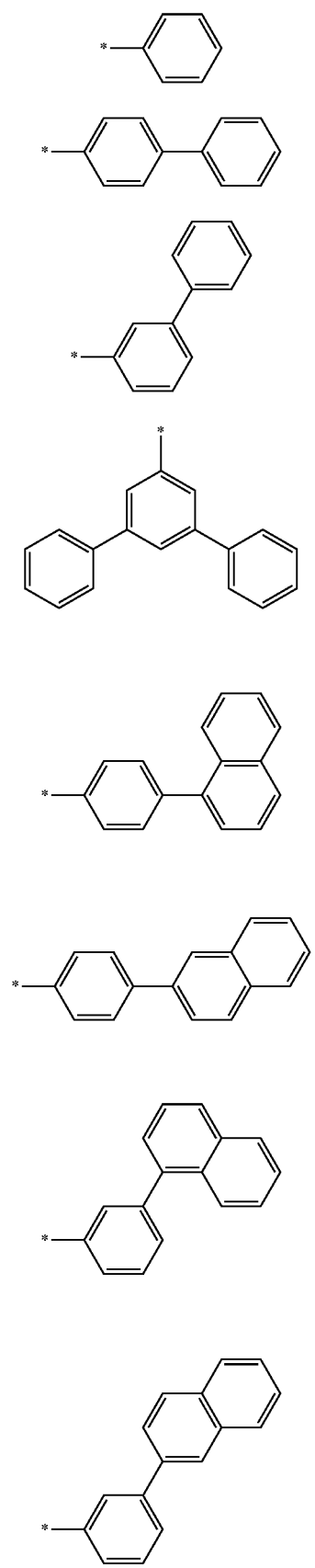
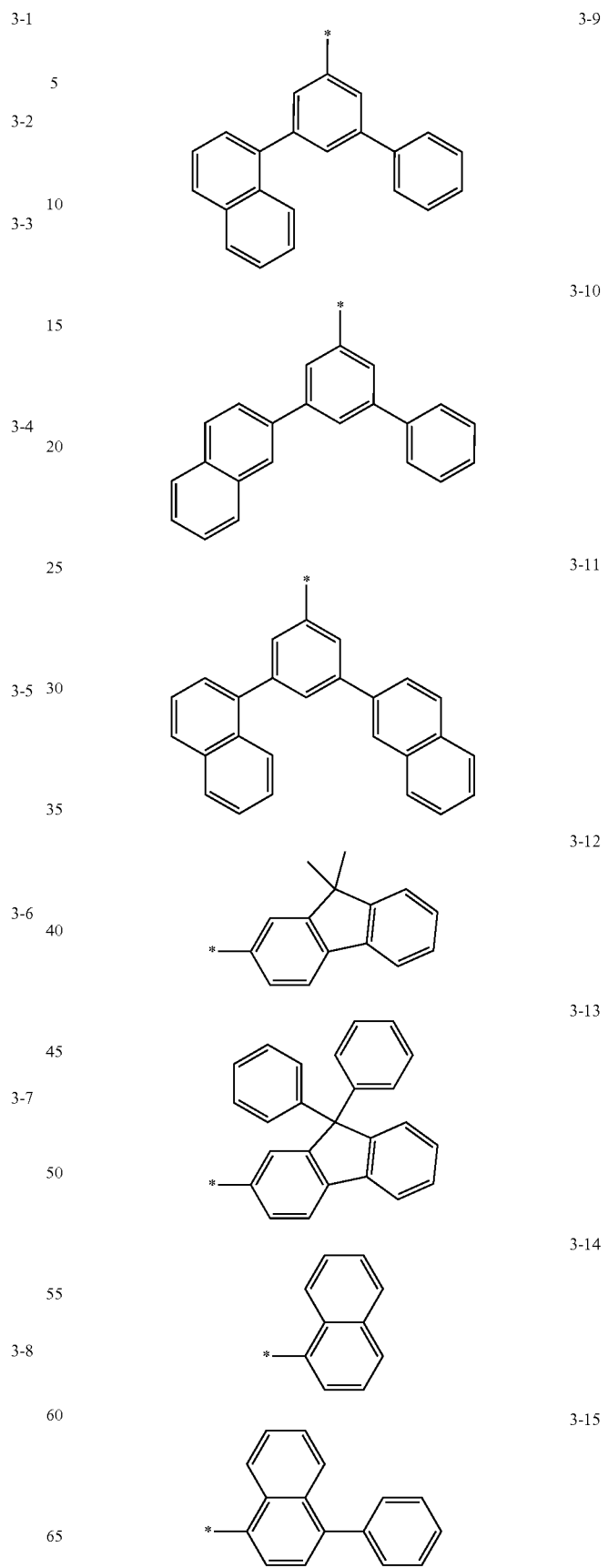

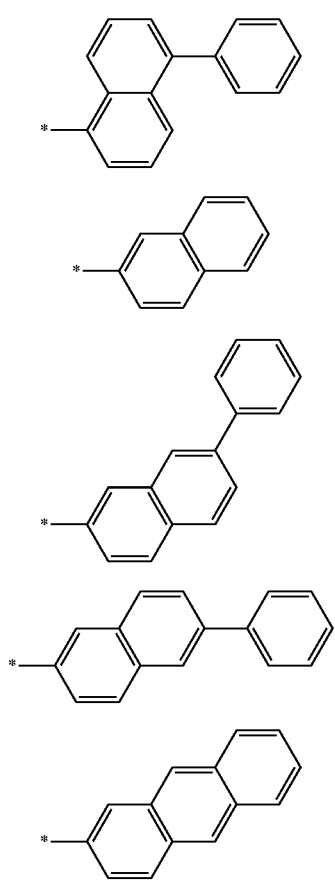

3-16

3-17

3-18

3-19

3-20 in Formulae 3-1 to 3-20 may indicate a binding site to a nitrogen atom (N) of Formulae 1 and 2.

For example, $R_1$ and $R_2$ in Formulae 1 and 2 may each independently be selected from i) a $C_1$-$C_{20}$ alkyl group;

ii) a $C_1$-$C_{20}$ alkyl group, substituted with at least one selected from a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a phenyl group, a naphtyl group, a fluorenyl group, a spiro-fluorenyl group group, a phenanthrenyl group, an anthryl group, a fluoranthenyl group, a triphenylenyl group, a pyrenyl group, a chrysenyl group, a pyridinyl group, a pyrazinyl group, a pyrimidinyl group, a pyridazinyl group, a isoindolyl group, an indolyl group, a quinolinyl group, a benzoquinolinyl group, a quinoxalinyl group, a quinazolinyl group, a cinnolinyl group, a carbazolyl group, and a triazinyl group;

iii) a phenyl group, a naphtyl group, a fluorenyl group, a spiro-fluorenyl group group, a phenanthrenyl group, an anthryl group, a fluoranthenyl group, a triphenylenyl group, a pyrenyl group, a chrysenyl group, a pyridinyl group, a pyrazinyl group, a pyrimidinyl group, a pyridazinyl group, a isoindolyl group, an indolyl group, a quinolinyl group, a benzoquinolinyl group, a quinoxalinyl group, a quinazolinyl group, a cinnolinyl group, a carbazolyl group, and a triazinyl group; and iv) a phenyl group, a naphtyl group, a fluorenyl group, a spiro-fluorenyl group group, a phenanthrenyl group, an anthryl group, a fluoranthenyl group, a triphenylenyl group, a pyrenyl group, a chrysenyl group, a pyridinyl group, a pyrazinyl group, a pyrimidinyl group, a pyridazinyl group, a isoindolyl group, an indolyl group, a quinolinyl group, a benzoquinolinyl group, a quinoxalinyl group, a quinazolinyl group, a cinnolinyl group, a carbazolyl group, and a triazinyl group, each substituted with at least one selected from a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphtyl group, a fluorenyl group, a spiro-fluorenyl group group, a phenanthrenyl group, an anthryl group, a fluoranthenyl group, a triphenylenyl group, a pyrenyl group, a chrysenyl group, a pyridinyl group, a pyrazinyl group, a pyrimidinyl group, a pyridazinyl group, a isoindolyl group, an indolyl group, a quinolinyl group, a benzoquinolinyl group, a quinoxalinyl group, a quinazolinyl group, a cinnolinyl group, a carbazolyl group, and a triazinyl group.

For example, $R_1$ and $R_2$ in Formulae 1 and 2 are each independently selected from a methyl group, an ethyl group, a propyl group, a butyl group, a pentyl group, a hexyl group, a heptyl group, and groups represented by Formulae 3-1 to 3-20:

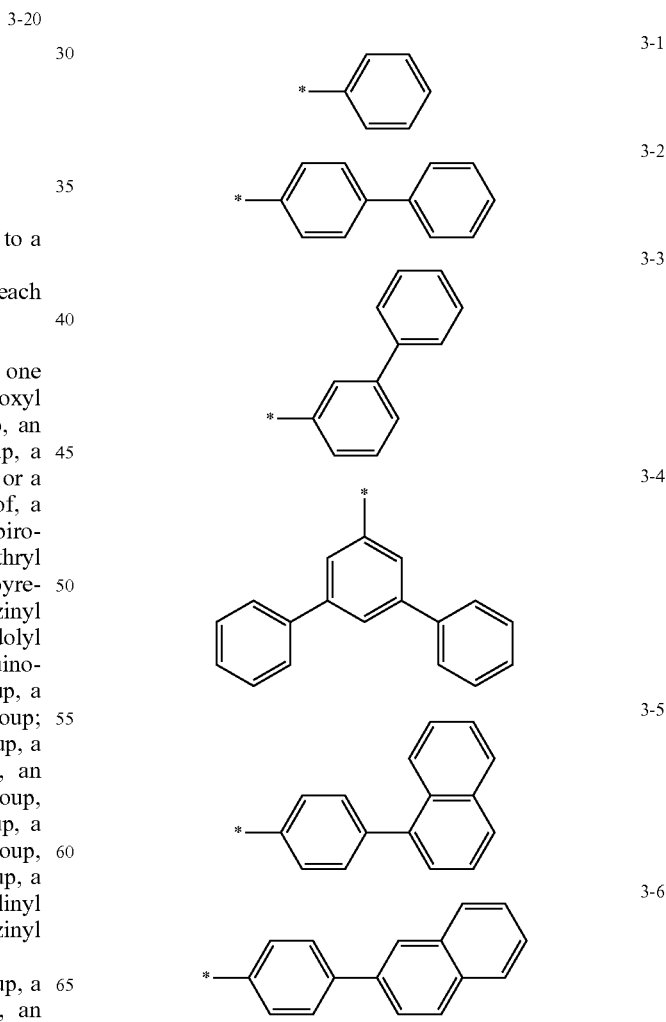

-continued
3-7
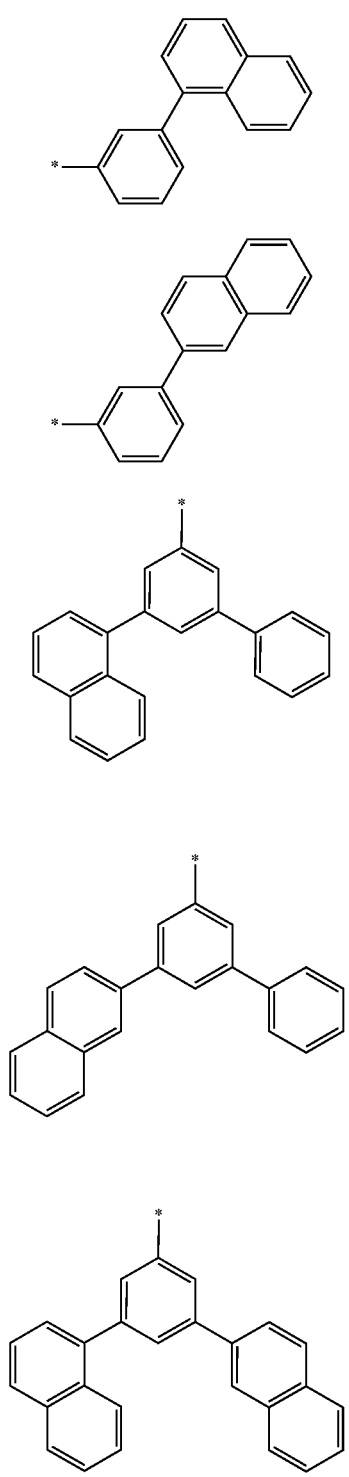
3-8
3-9
3-10
3-11
3-12
-continued
3-13
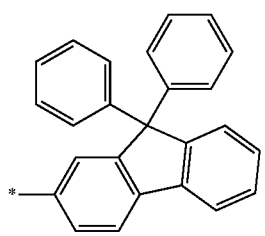
3-14
3-15
3-16
3-17
3-18
3-19
3-20
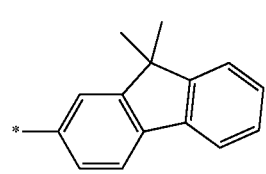
in Formulae 3-1 to 3-20 indicates a carbon of fluorene of Formula 1.
For example, $R_3$, $R_4$, and $R_{11}$ to $R_{24}$ in Formulae 1 and 2 may each independently be selected from
i) hydrogen, deuterium, a halogen atom, a hydroxyl group, a cyano group, a nitro group, an amino group, an amidino group, hydrazine, hydrazone, a carboxyl group and a salt thereof, a sulfonic acid and a salt thereof, a phosphoric acid and a salt thereof, and a $C_1$-$C_{20}$ alkyl group;

ii) a $C_1$-$C_{20}$ alkyl group, substituted with at least one selected from a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a phenyl group, a naphtyl group, a fluorenyl group, a spiro-fluorenyl group group, a phenanthrenyl group, an anthryl group, a fluoranthenyl group, a triphenylenyl group, a pyrenyl group, a chrysenyl group, a pyridinyl group, a pyrazinyl group, a pyrimidinyl group, a pyridazinyl group, a isoindolyl group, an indolyl group, a quinolinyl group, a benzoquinolinyl group, a quinoxalinyl group, a quinazolinyl group, a cinnolinyl group, a carbazolyl group, and a triazinyl group;

iii) a phenyl group, a naphtyl group, a fluorenyl group, a spiro-fluorenyl group group, a phenanthrenyl group, an anthryl group, a fluoranthenyl group, a triphenylenyl group, a pyrenyl group, a chrysenyl group, a pyridinyl group, a pyrazinyl group, a pyrimidinyl group, a pyridazinyl group, a isoindolyl group, an indolyl group, a quinolinyl group, a benzoquinolinyl group, a quinoxalinyl group, a quinazolinyl group, a cinnolinyl group, a carbazolyl group, and a triazinyl group; and iv) a phenyl group, a naphtyl group, a fluorenyl group, a spiro-fluorenyl group group, a phenanthrenyl group, an anthryl group, a fluoranthenyl group, a triphenylenyl group, a pyrenyl group, a chrysenyl group, a pyridinyl group, a pyrazinyl group, a pyrimidinyl group, a pyridazinyl group, a isoindolyl group, an indolyl group, a quinolinyl group, a benzoquinolinyl group, a quinoxalinyl group, a quinazolinyl group, a cinnolinyl group, a carbazolyl group, and a triazinyl group, each substituted with at least one selected from a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphtyl group, a fluorenyl group, a spiro-fluorenyl group group, a phenanthrenyl group, an anthryl group, a fluoranthenyl group, a triphenylenyl group, a pyrenyl group, a chrysenyl group, a pyridinyl group, a pyrazinyl group, a pyrimidinyl group, a pyridazinyl group, a isoindolyl group, an indolyl group, a quinolinyl group, a benzoquinolinyl group, a quinoxalinyl group, a quinazolinyl group, a cinnolinyl group, a carbazolyl group, and a triazinyl group.

For example, $R_3$, $R_4$, and $R_{11}$ to $R_{24}$ in Formulae 1 and 2 may each independently be selected from hydrogen, deuterium, a halogen atom, a hydroxyl group, a cyano group, a nitro group, an amino group, an amidino group, hydrazine, hydrazone, a carboxyl group and a salt thereof, a sulfonic acid and a salt thereof, a phosphoric acid and a salt thereof, and a $C_1$-$C_{20}$ alkyl group.

For example, $R_3$, $R_4$, and $R_{11}$ to $R_{24}$ in Formulae 1 and 2 may each independently be selected from a hydrogen, a deuterium, a halogen atom, a hydroxyl group, a cyano group, a nitro group, an amino group, an amidino group, a hydrazine group, a hydrazone group, a carboxyl group and a salt thereof, a sulfonic acid and a salt thereof, a phosphoric acid and a salt thereof, a methyl group, an ethyl group, a propyl group, a butyl group, a pentyl group, a hexyl group, a heptyl group, and groups represented by Formulae 3-1 to 3-20:

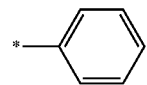

3-1

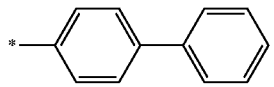

3-2

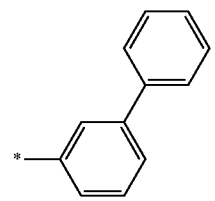

3-3

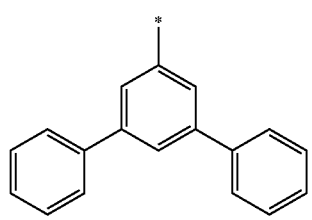

3-4

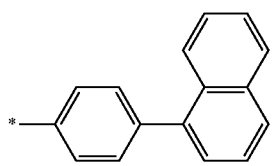

3-5

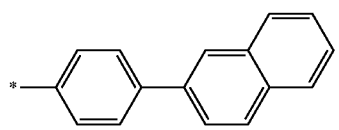

3-6

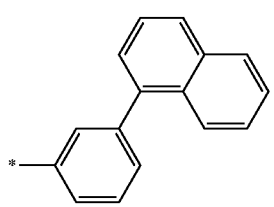

3-7

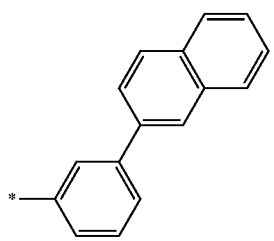

3-8

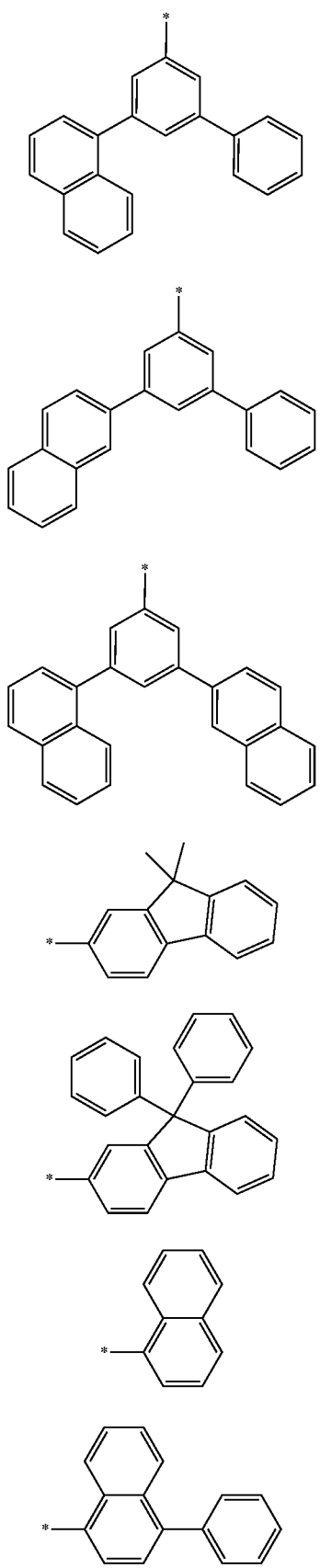
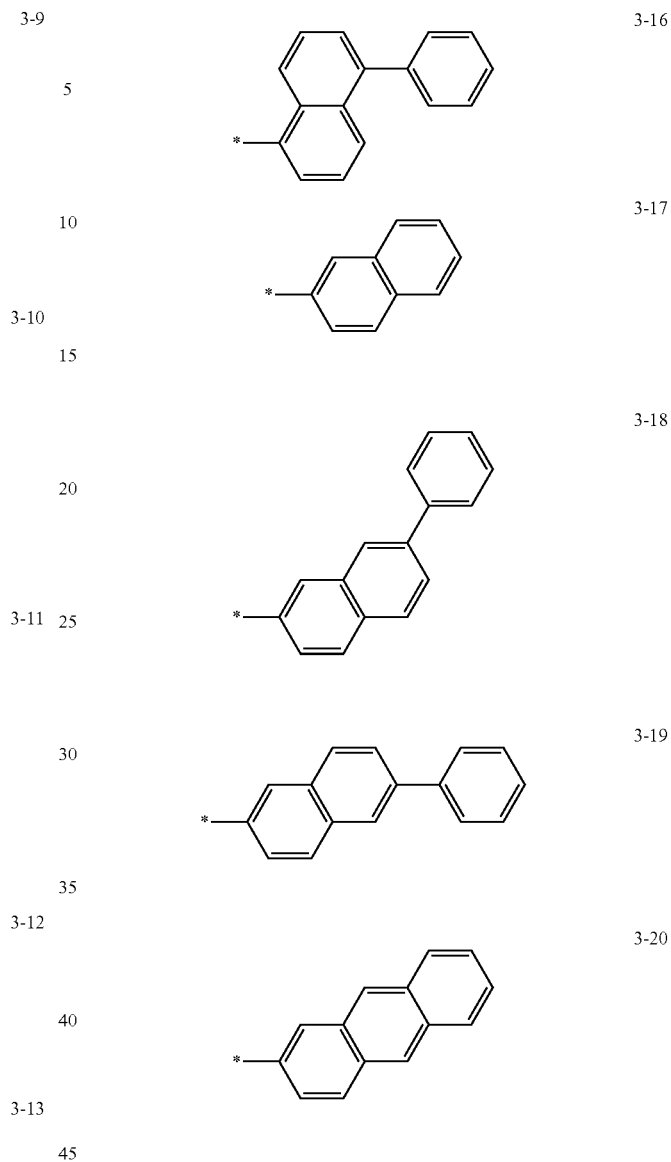
The first compound, the second compound, the third compound, and the fourth compound may each independently be a compound represented by Formula 1A or 2A below:
<Formula 1A>
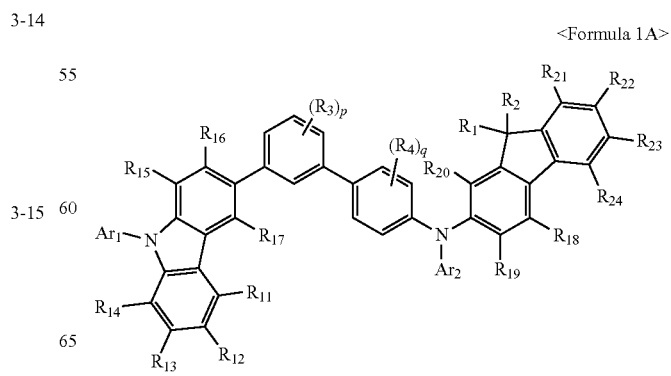

<Formula 2A>
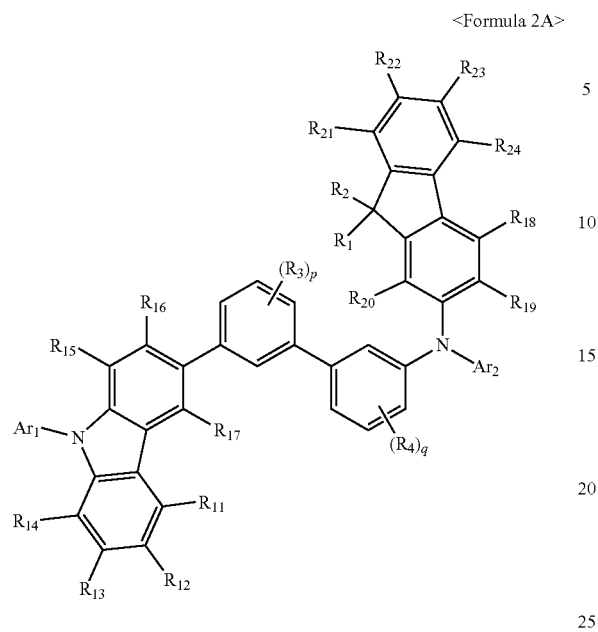
wherein in Formulae 1A and 2A, $Ar_1$, $Ar_2$, $R_1$ to $R_4$, $R_{11}$ to $R_{24}$, p and q may each independently be the same as groups defined for Formula 1 or Formula 2.
In an embodiment, $Ar_1$ and $Ar_2$ may each independently be represented by one of Formulae 3-1 to 3-20 below:
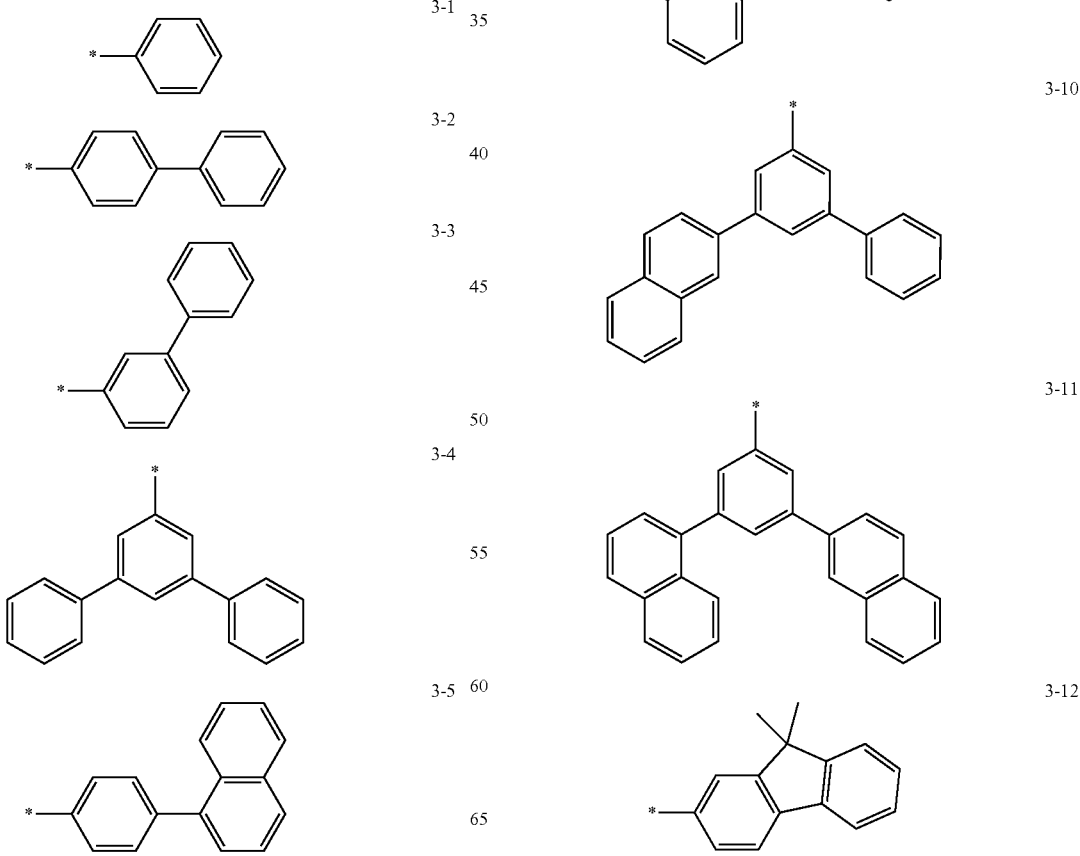

-continued
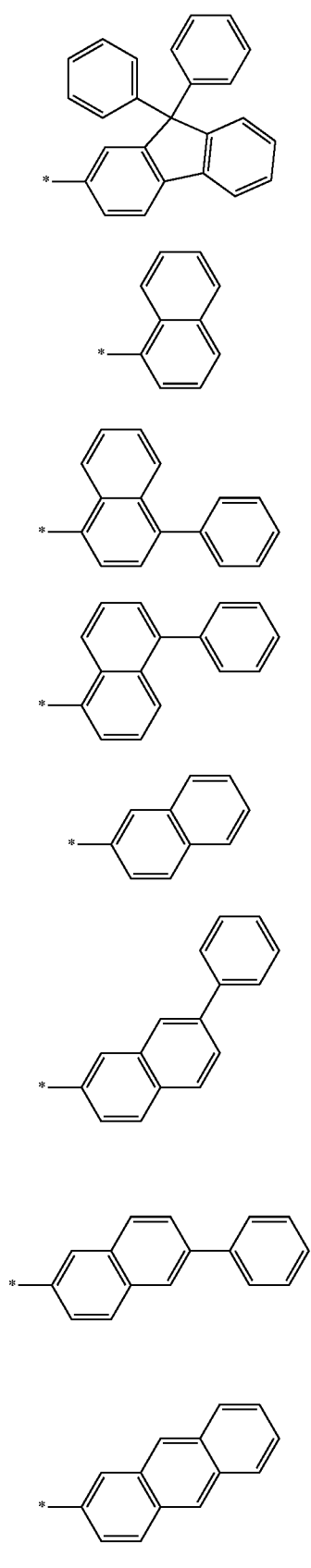
$R_1$ and $R_2$ are each independently a $C_1$-$C_{20}$ alkyl group or a group represented by Formula 3-1 to 3-20 below:
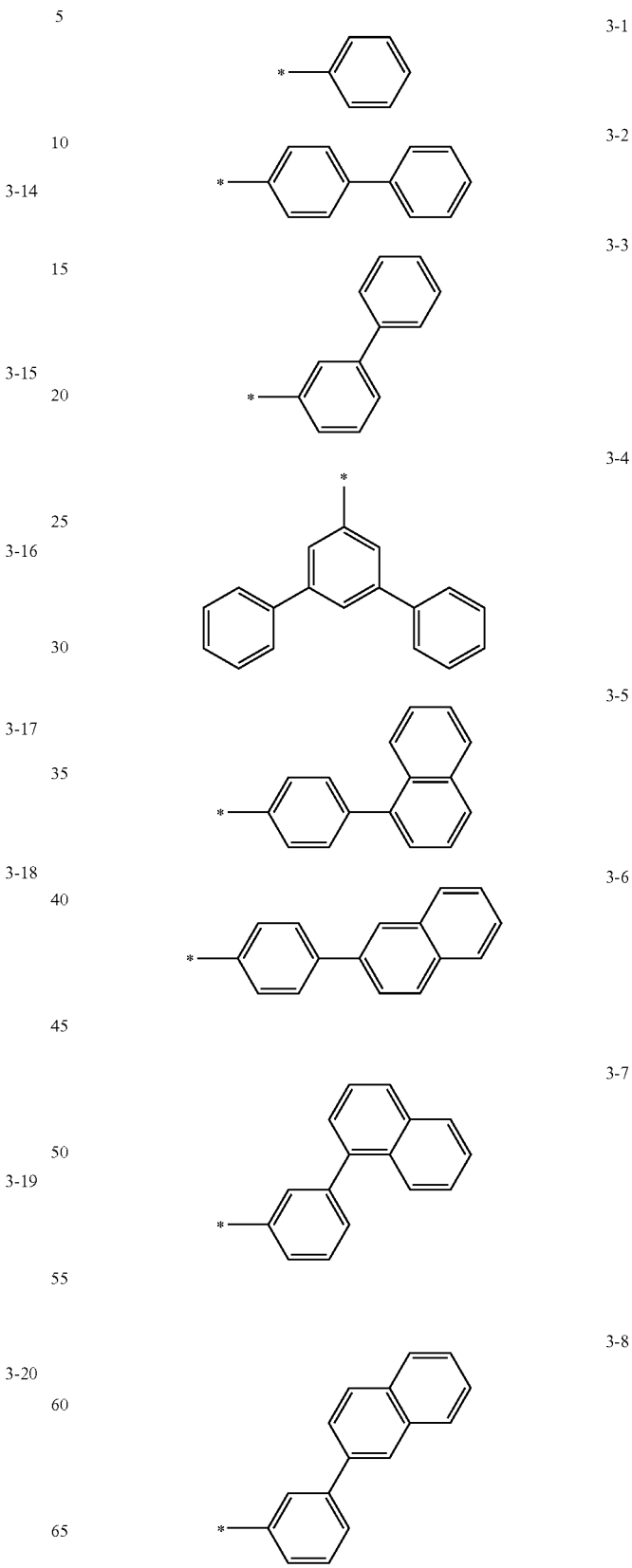

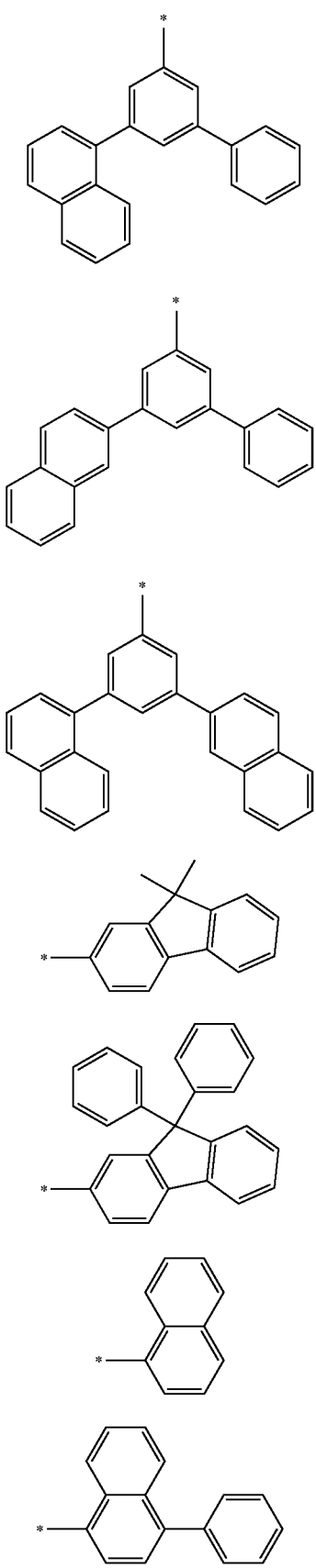

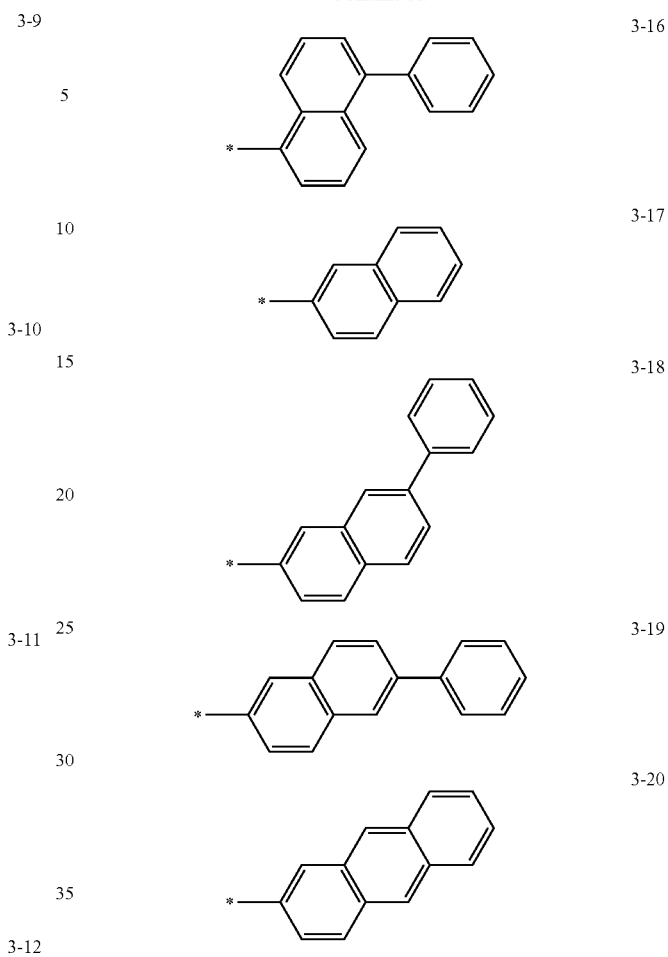

$R_3$, $R_4$ and $R_{11}$ to $R_{24}$ are each independently a hydrogen, a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, or a group represented by Formulae 3-1 to 3-20 below:

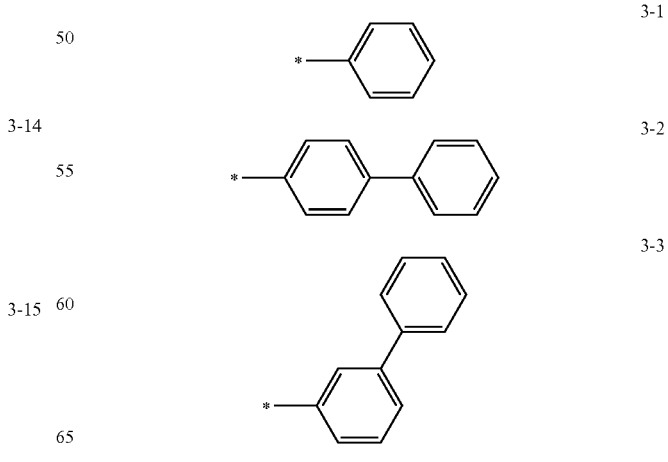

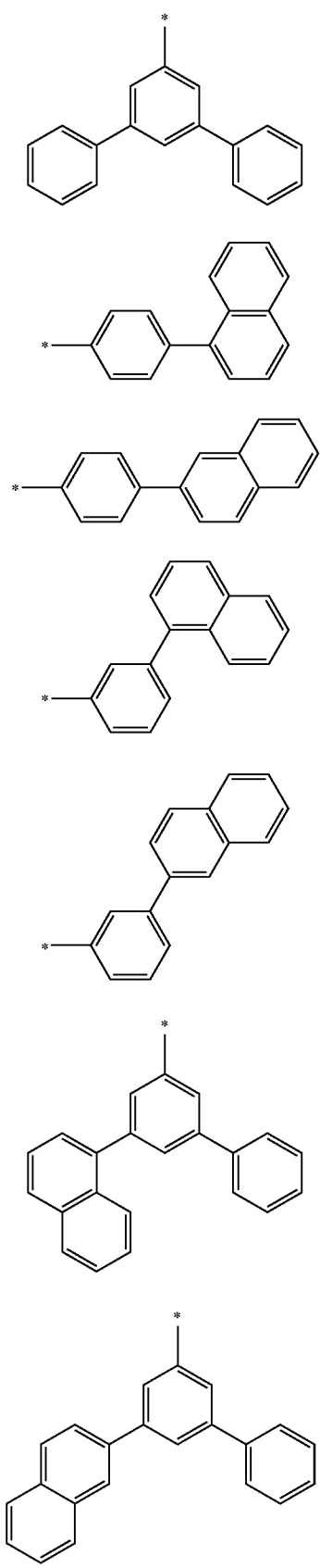
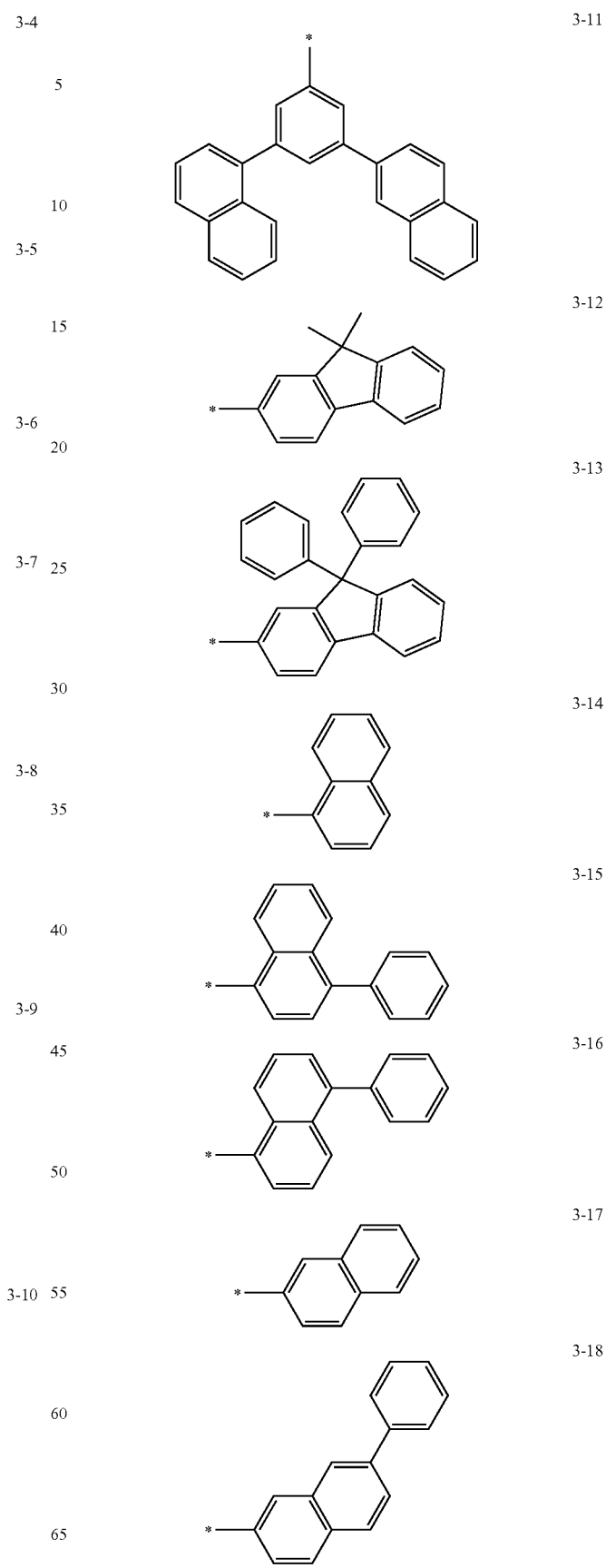

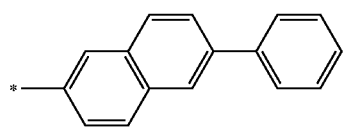
3-19
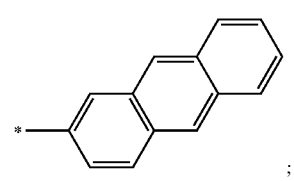
3-20
and
p and q are each independently an integer of 1 to 4.
For example, $R_3$, $R_4$, and $R_{11}$ to $R_{24}$ in Formulae 1A and 2A may each be hydrogen.
In an embodiment, the first compound, the second compound, the third compound, and the fourth compound may each independently be selected from Compounds 1 to 96 below:
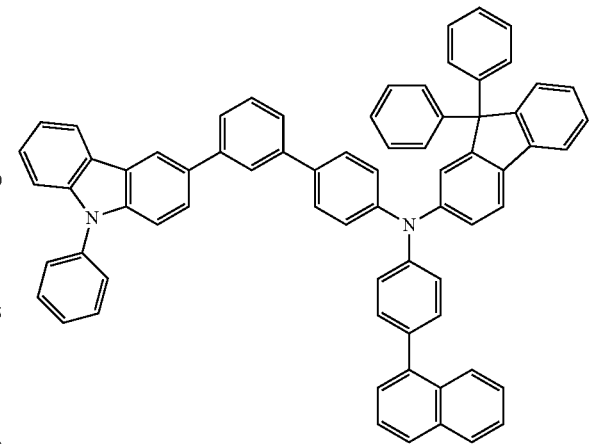
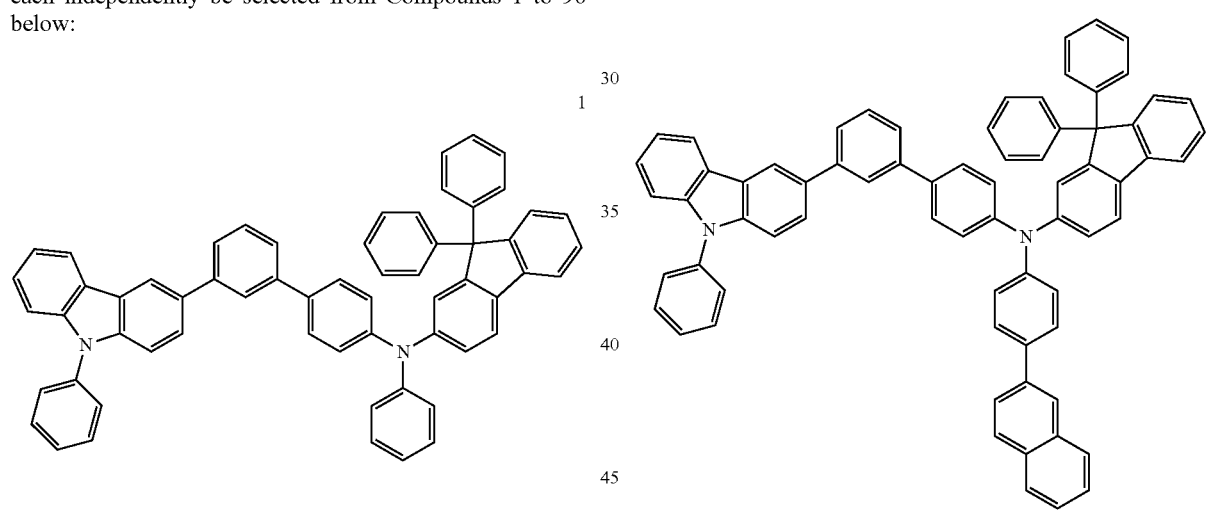
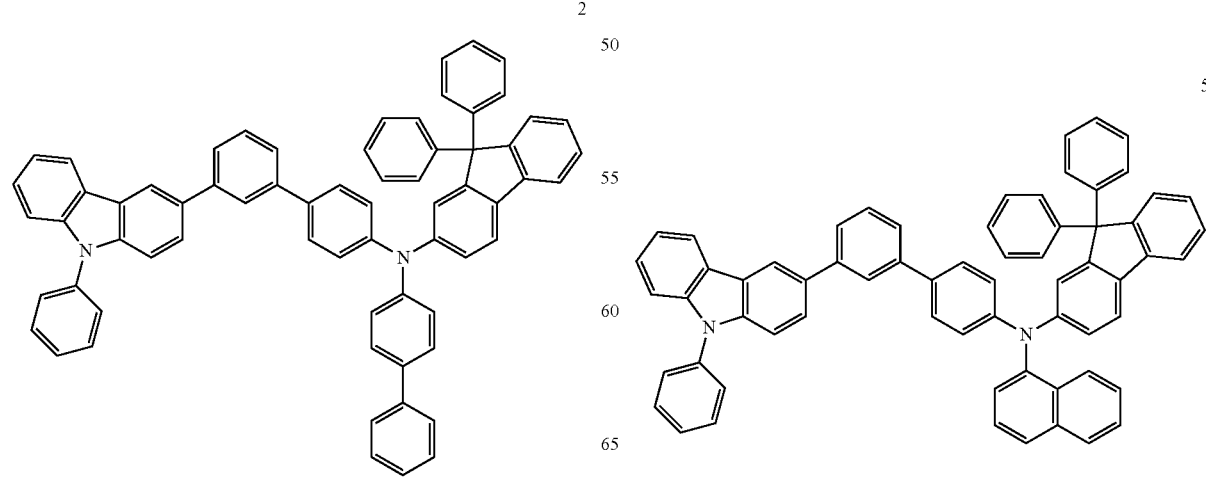

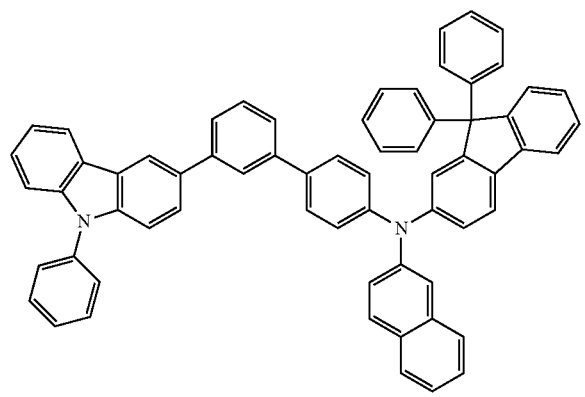
6
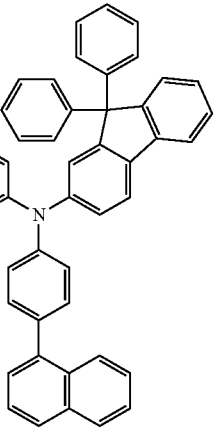
5
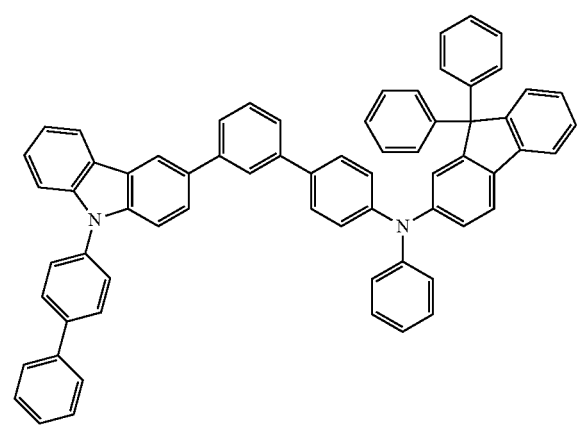
7
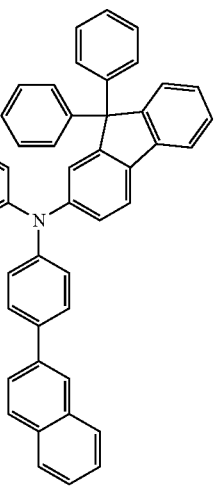
9
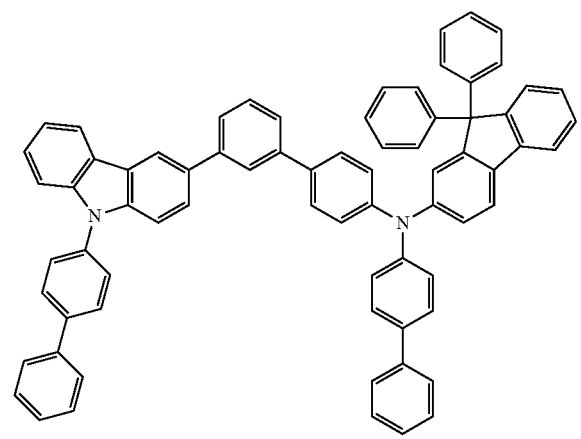
8
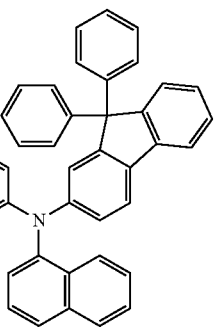
10
11

12
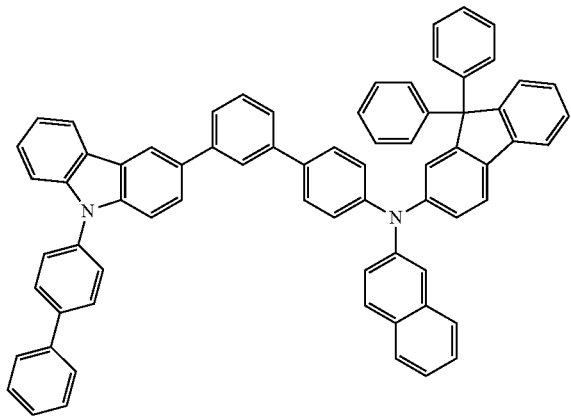
13
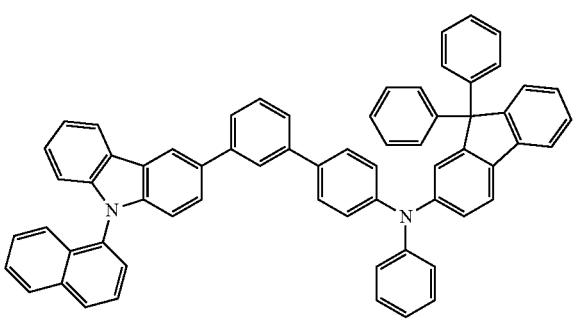
14
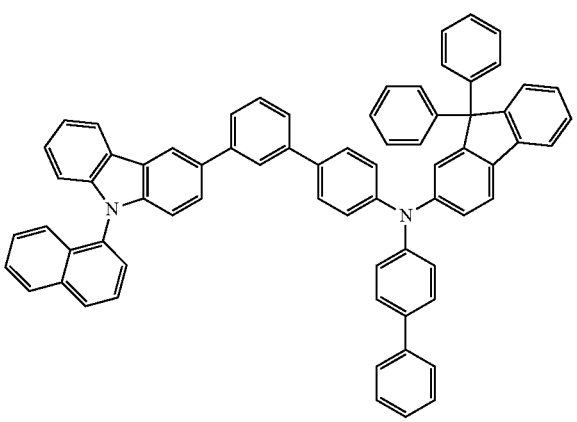
15
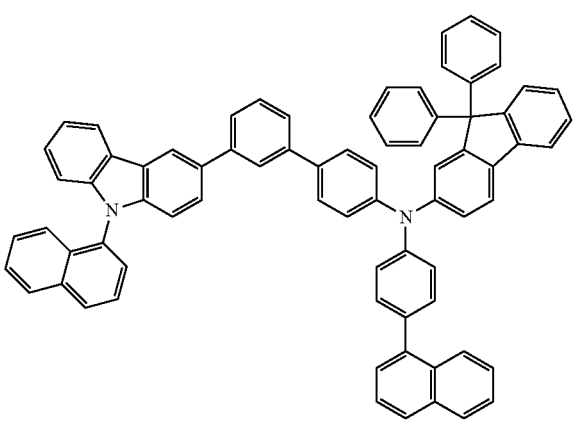
16
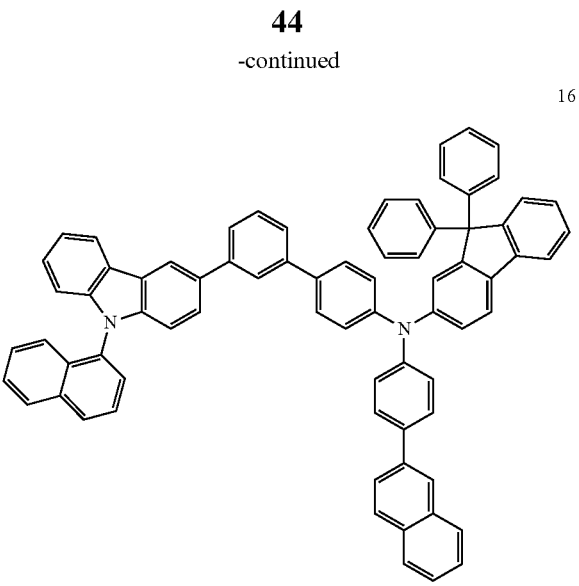
17
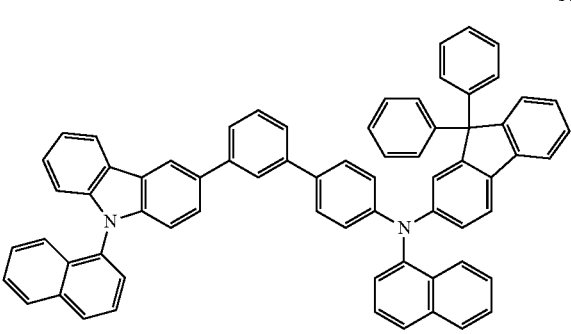
18
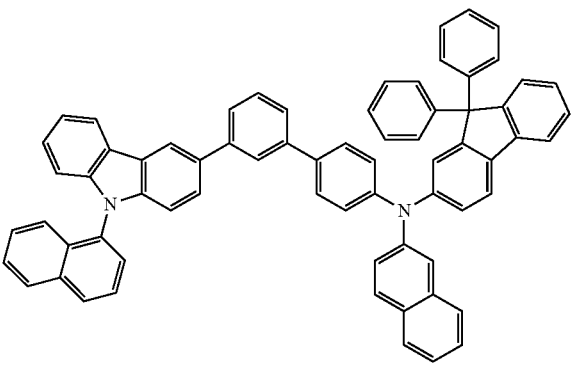
19
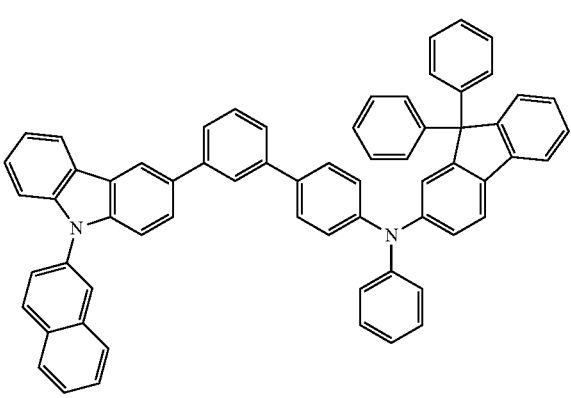

20
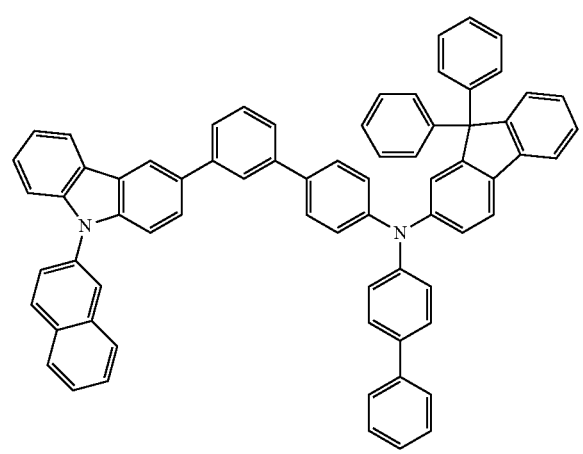
21
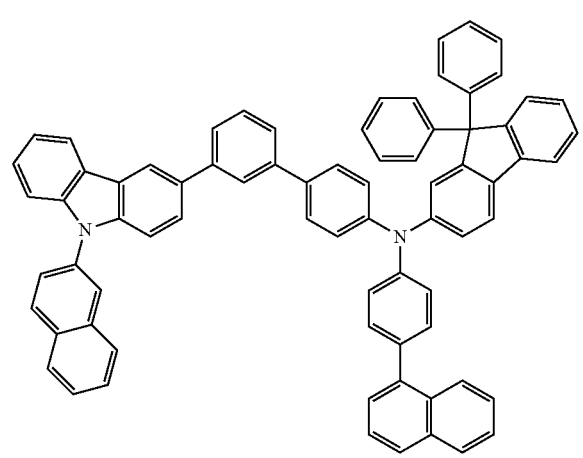
22
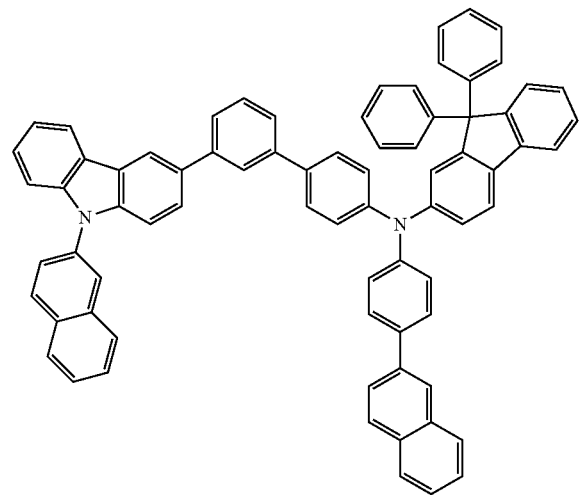
23
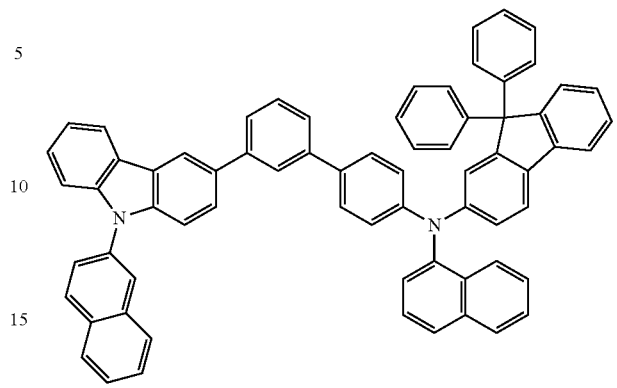
24
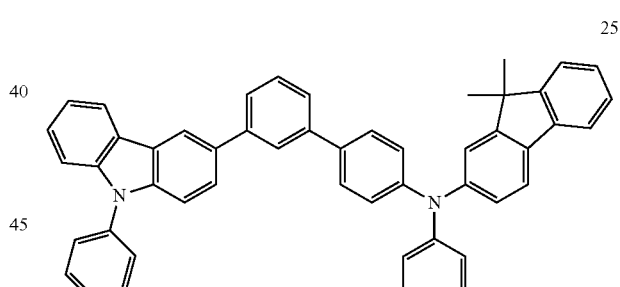
25
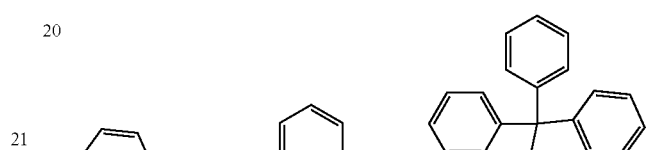
26
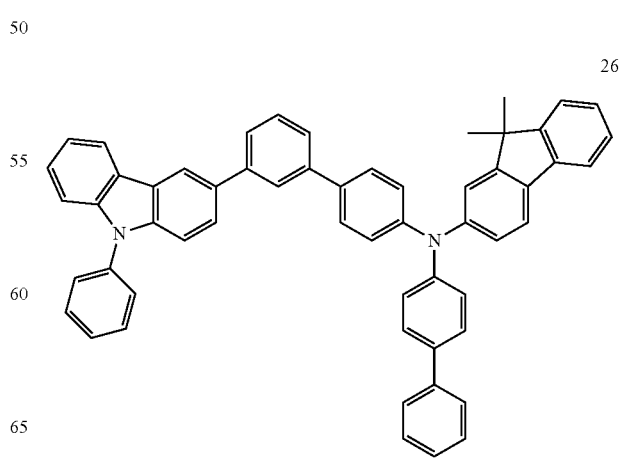

27
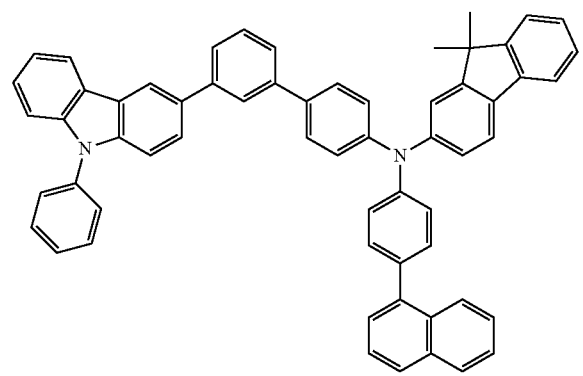
28
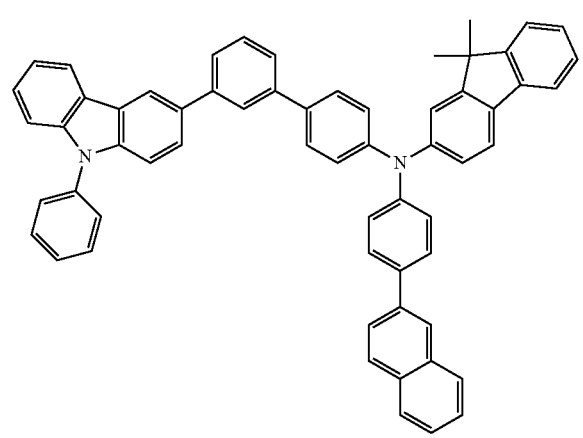
29
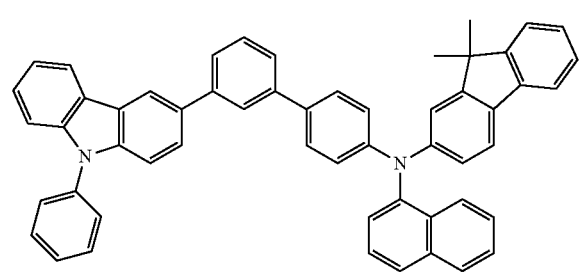
30
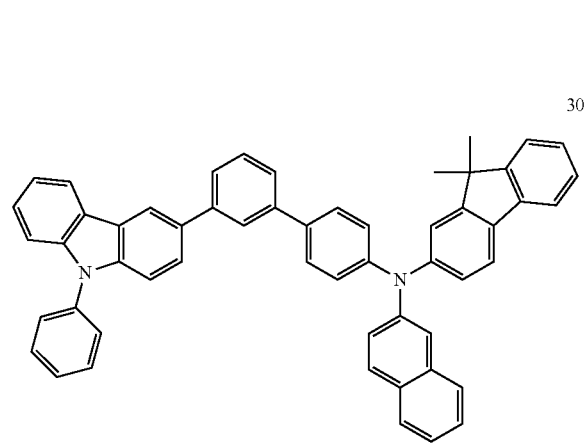
31
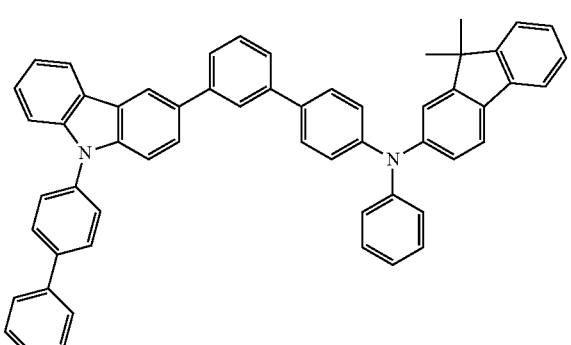
32
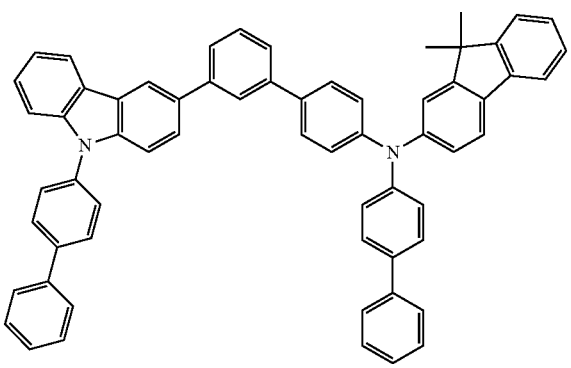
33
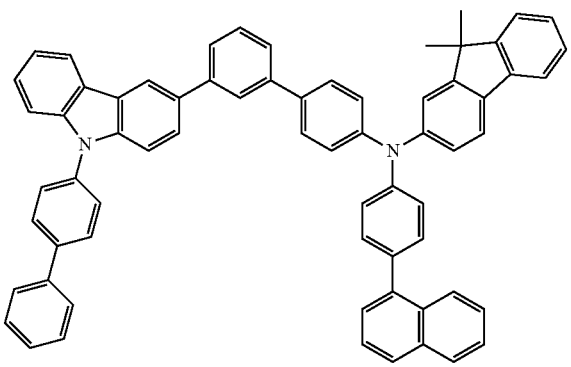
34
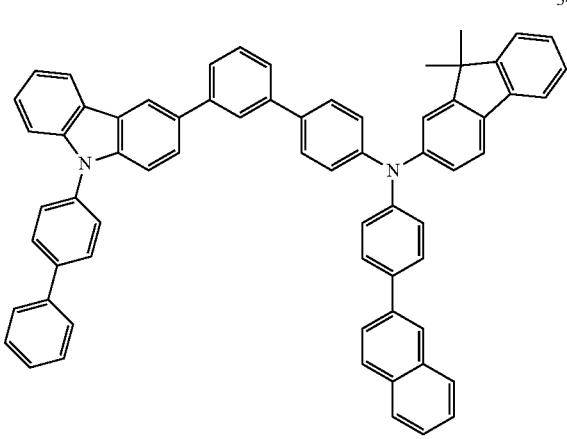

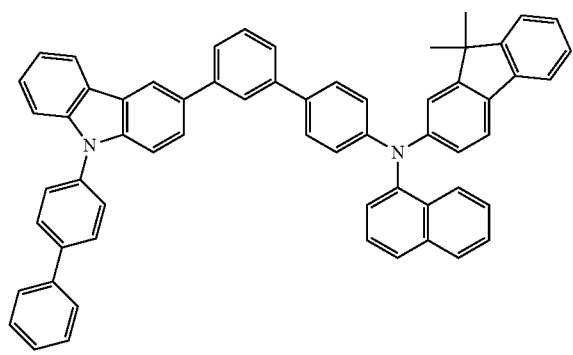
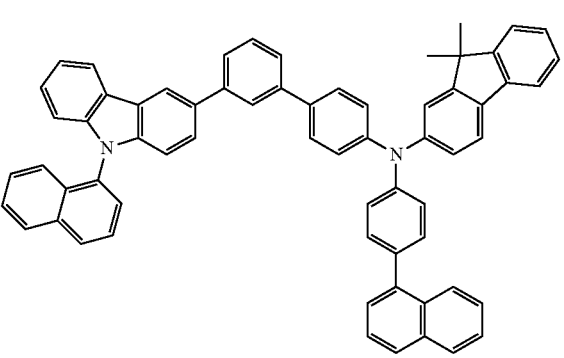

-continued
43
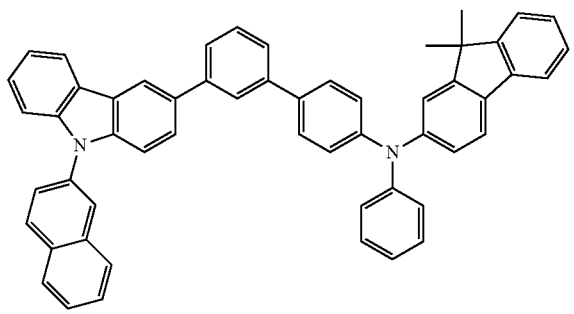
44
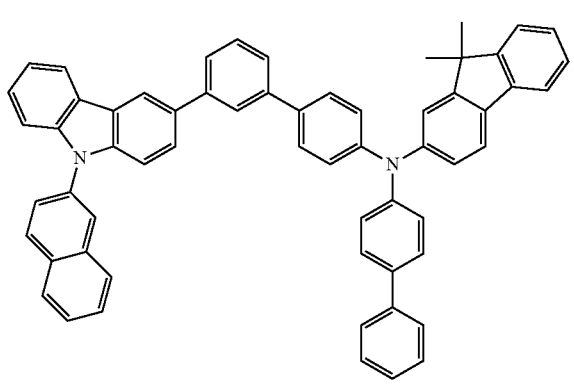
45
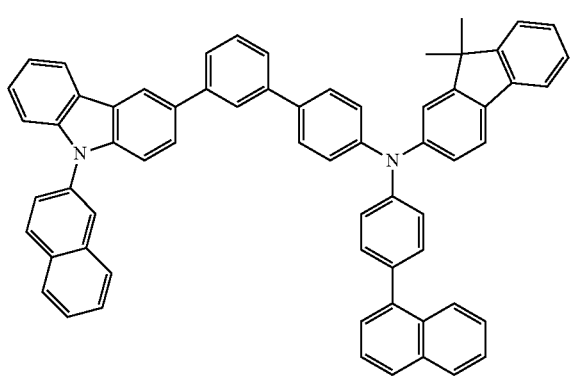
46
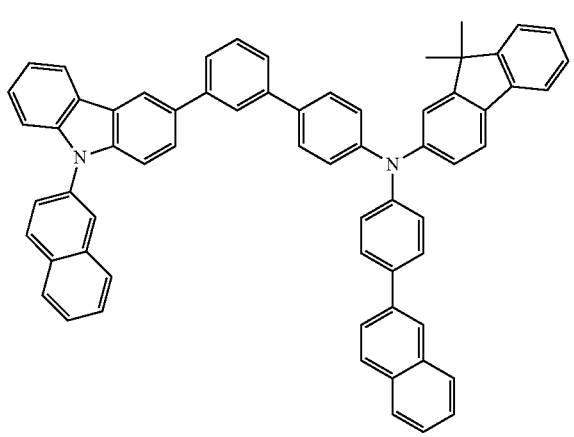
-continued
47
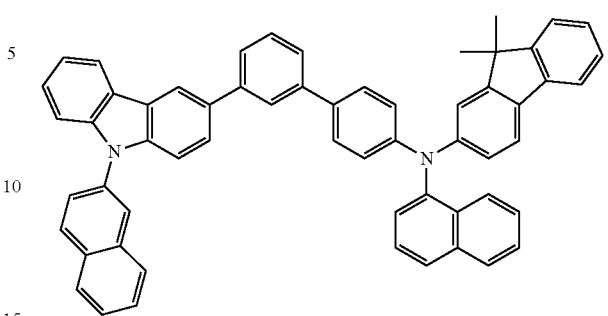
48
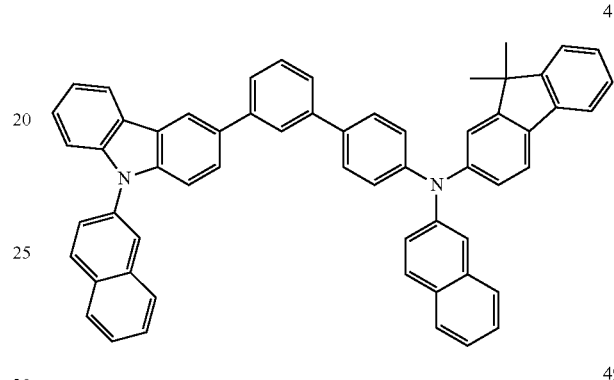
49
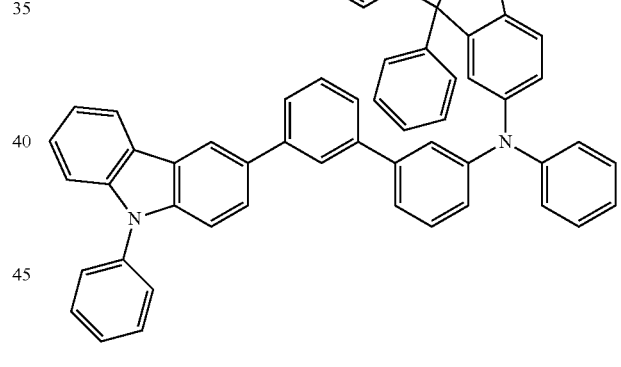
50
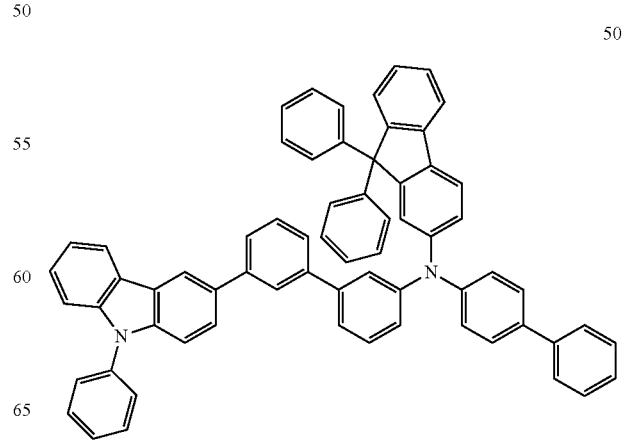

51
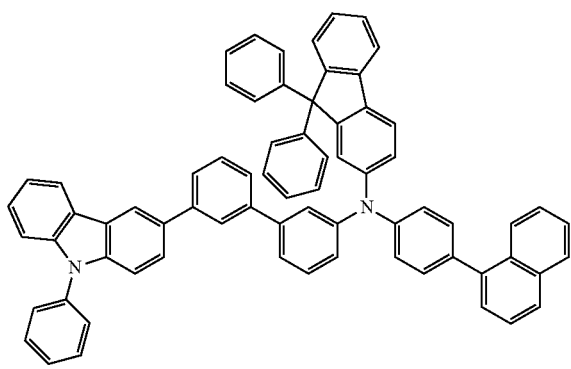
52
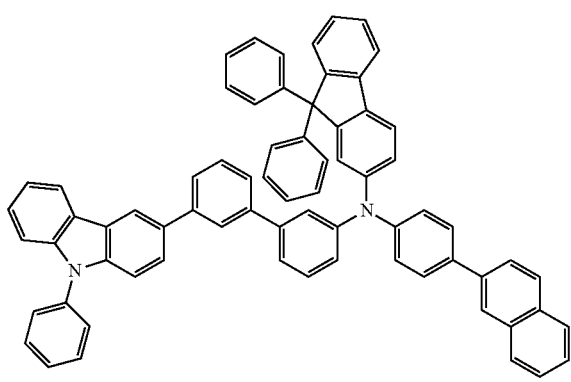
53
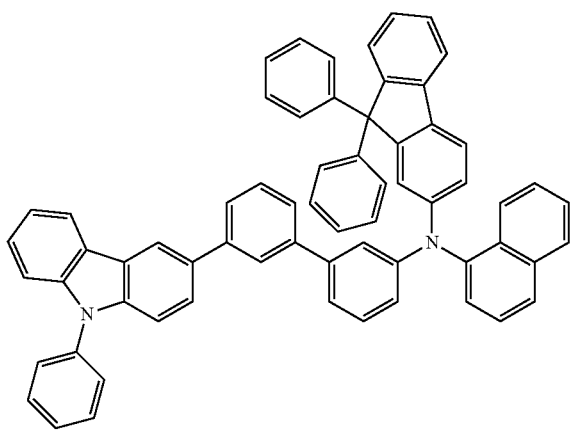
54
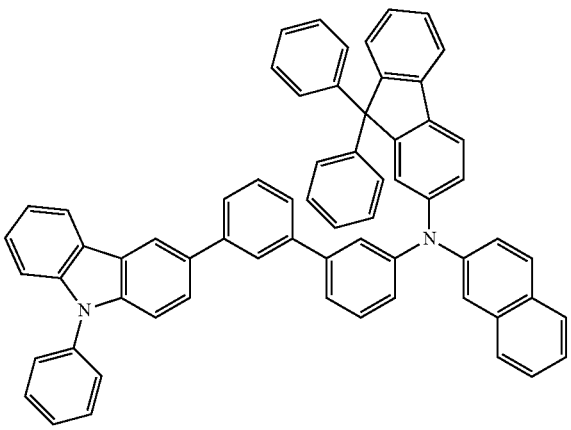
55
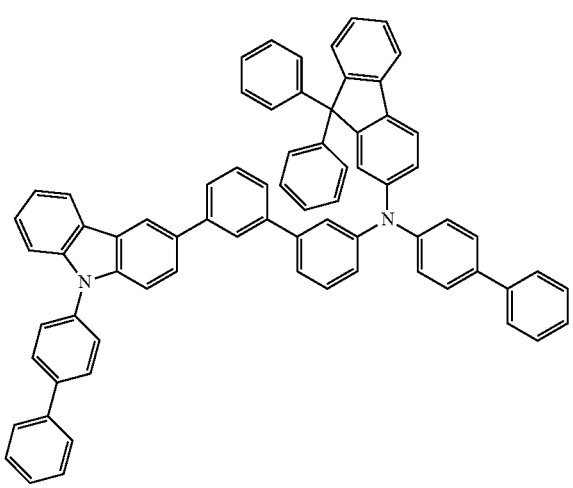
56

57
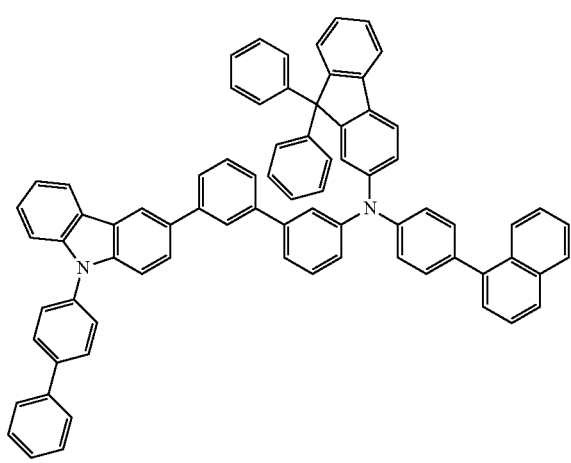
58
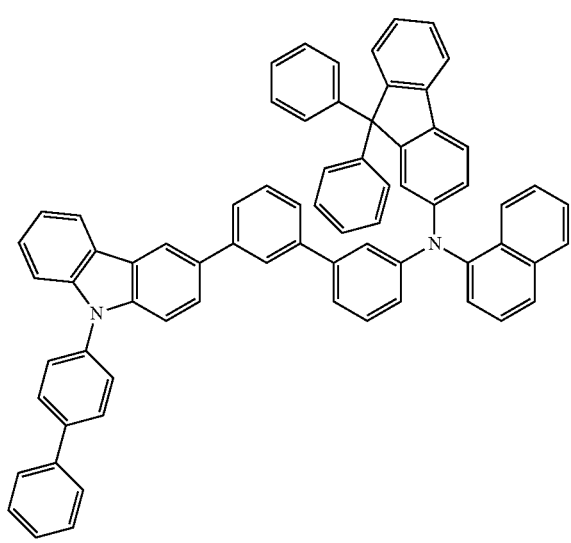
59
60
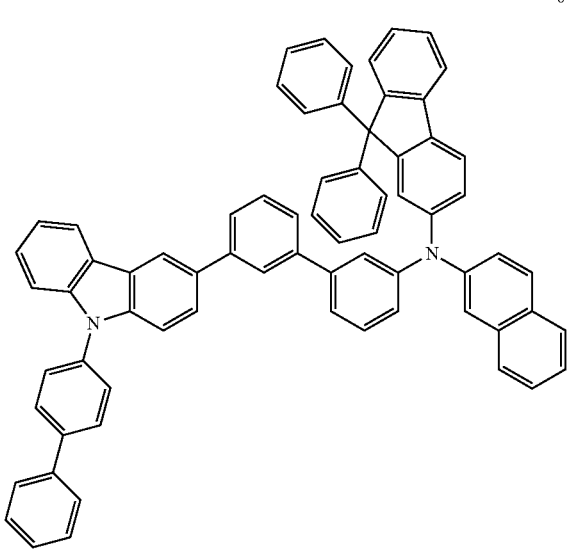
61
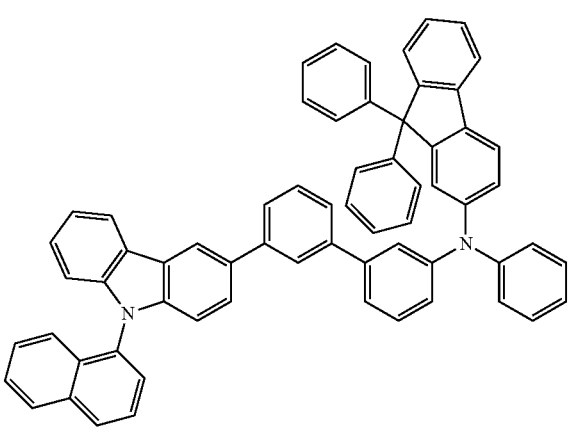
62
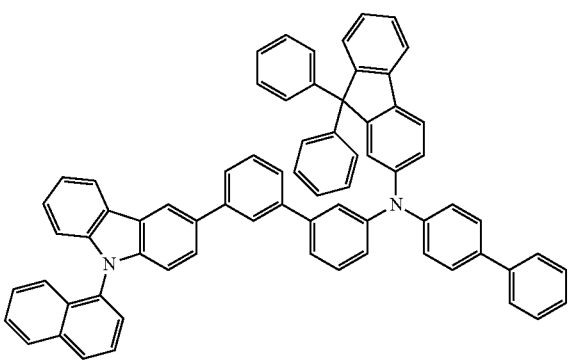

63
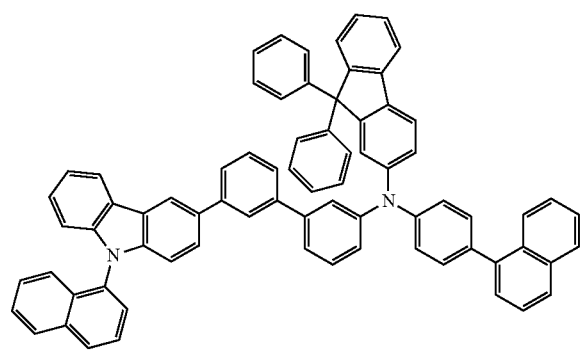
64
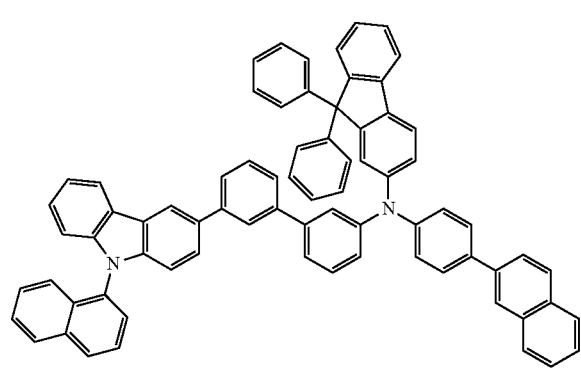
65
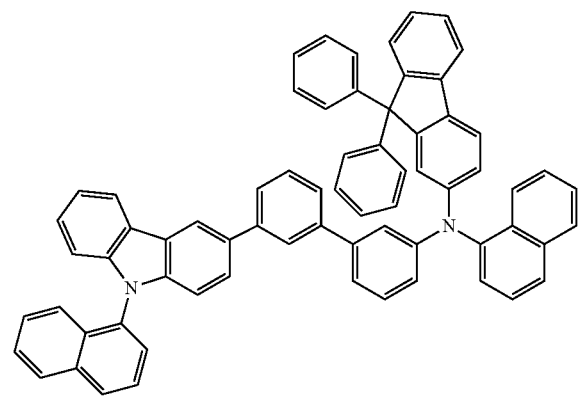
66
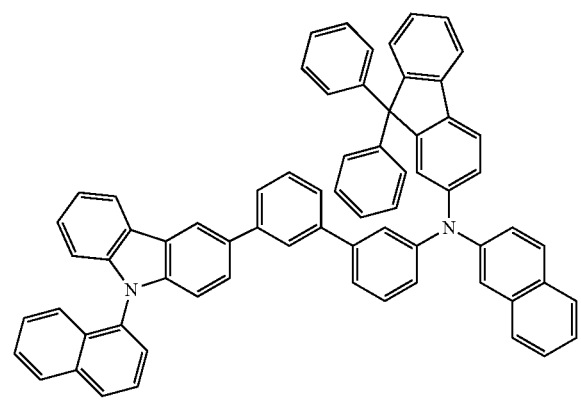
67
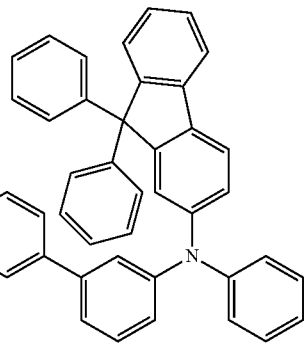
68
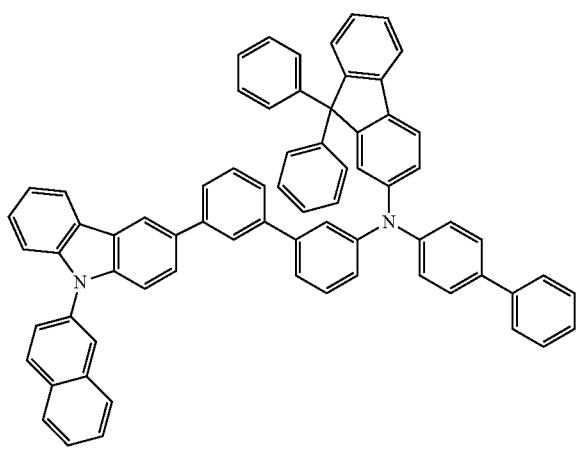
69
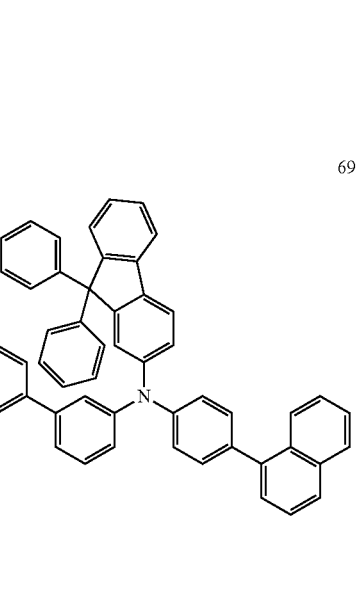

70
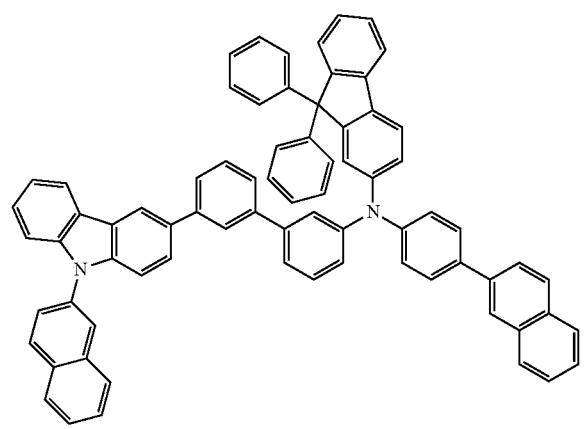
71
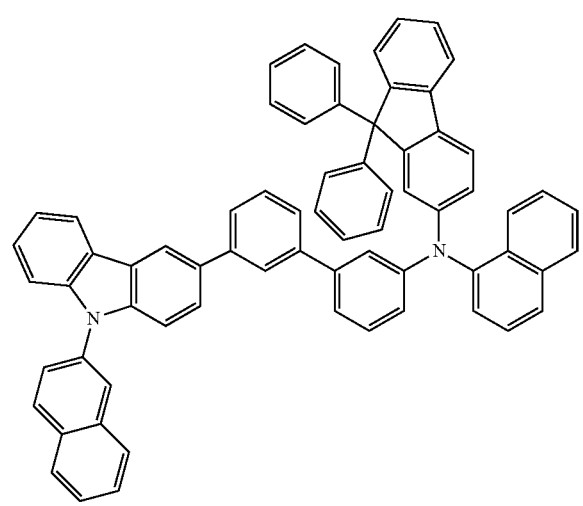
72
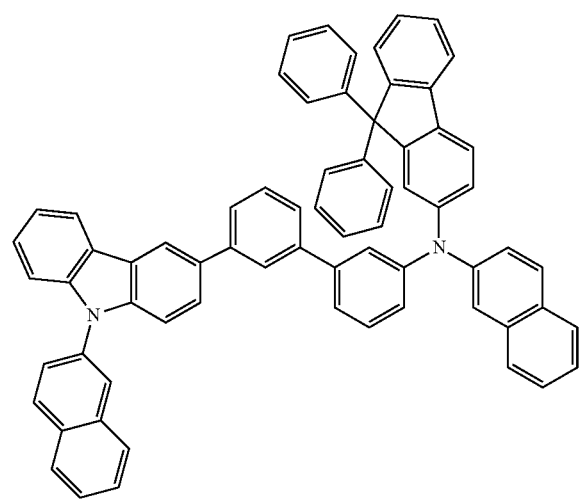
73
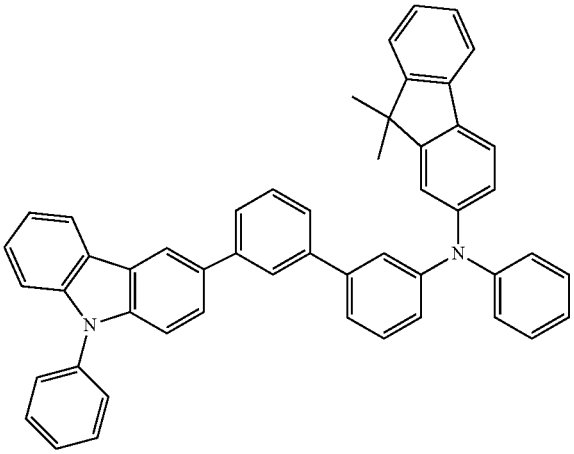
74
75
76
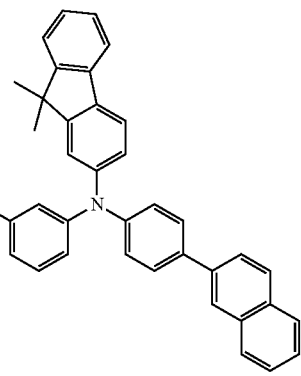

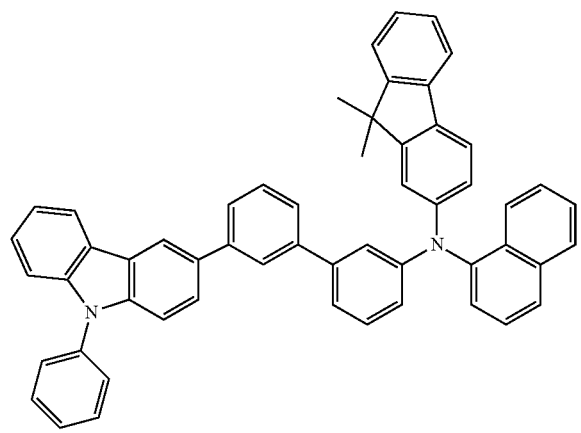
77
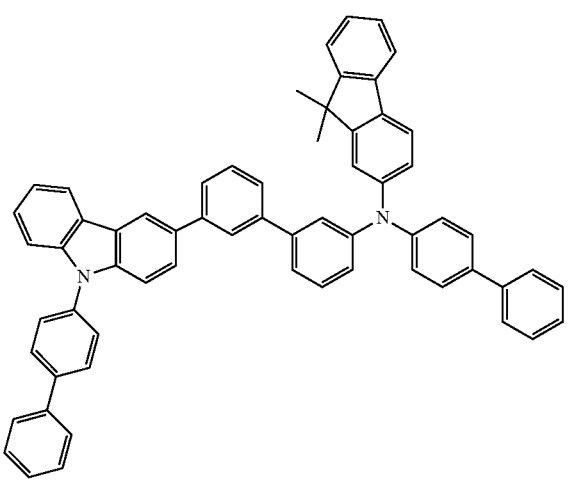
80
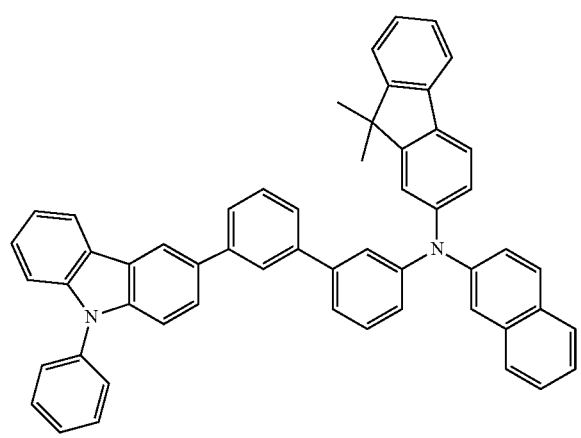
78
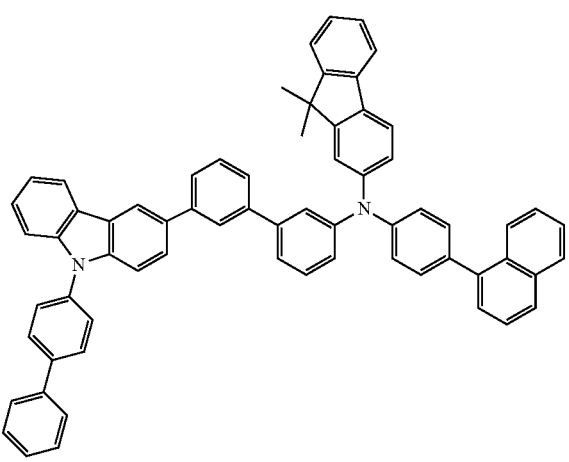
81
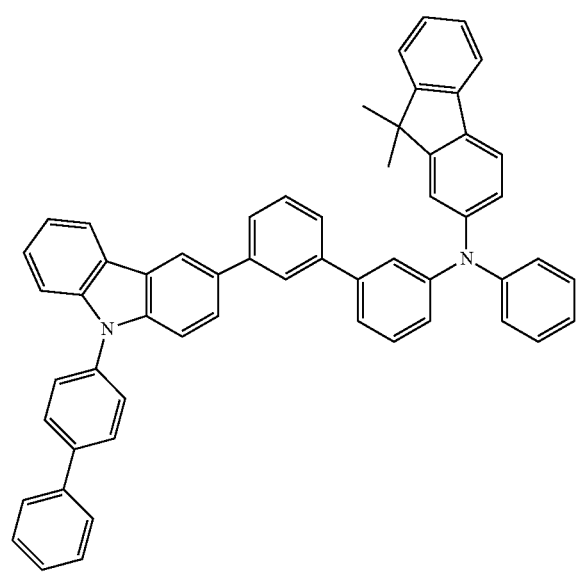
79
82

83
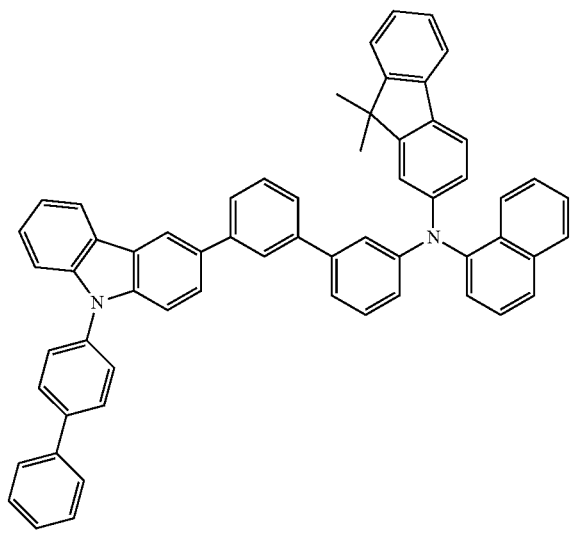
84
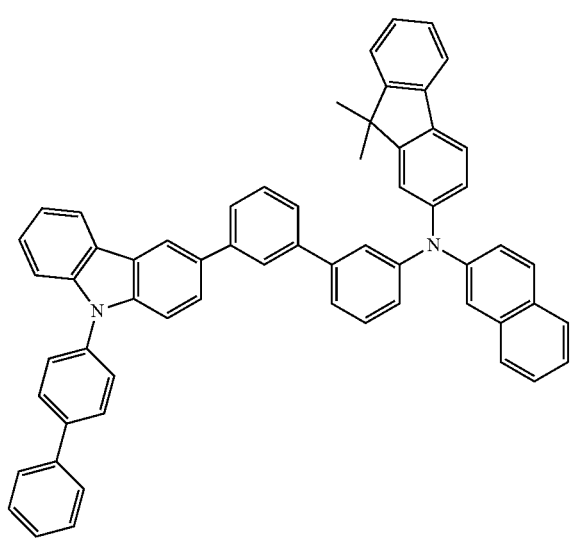
85
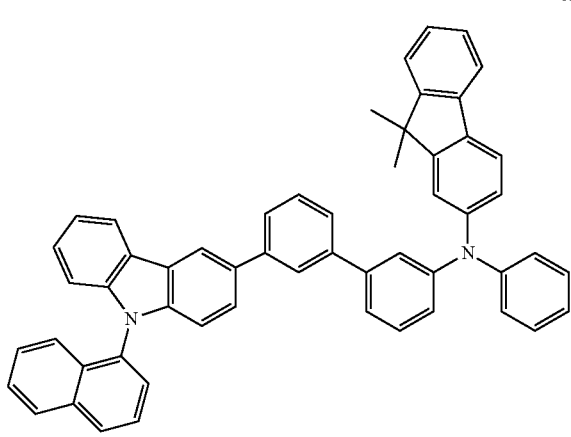
86
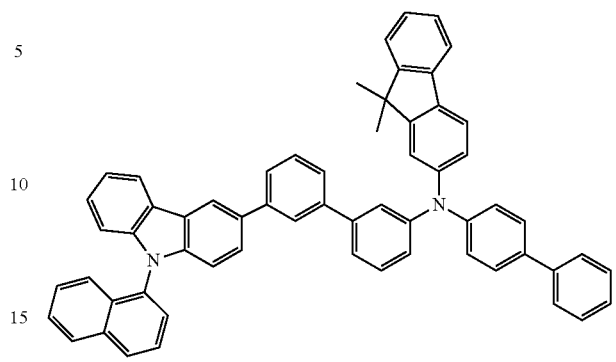
87
88
89

90
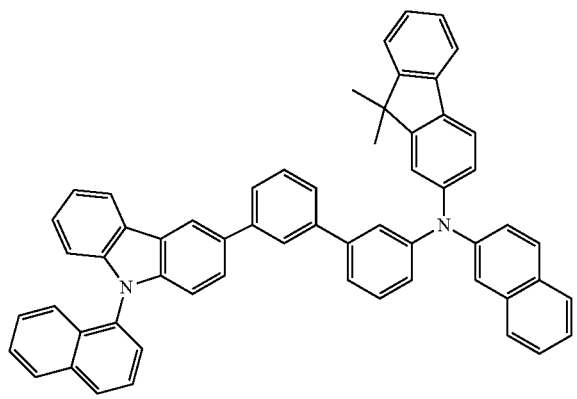
91
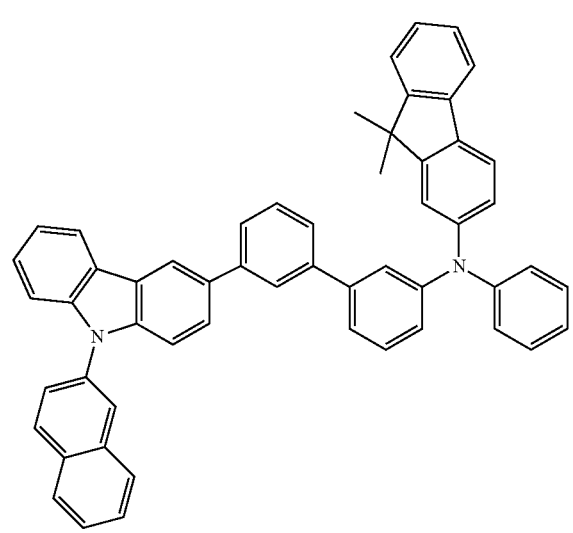
93
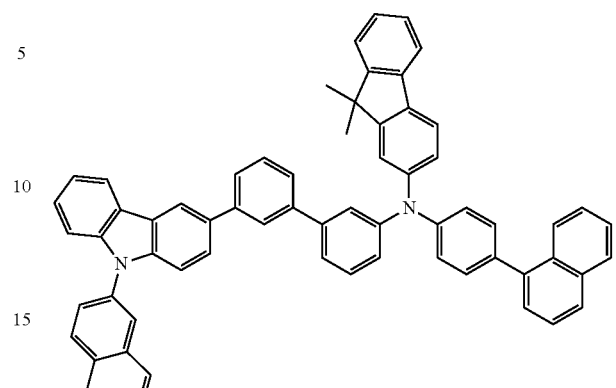
94
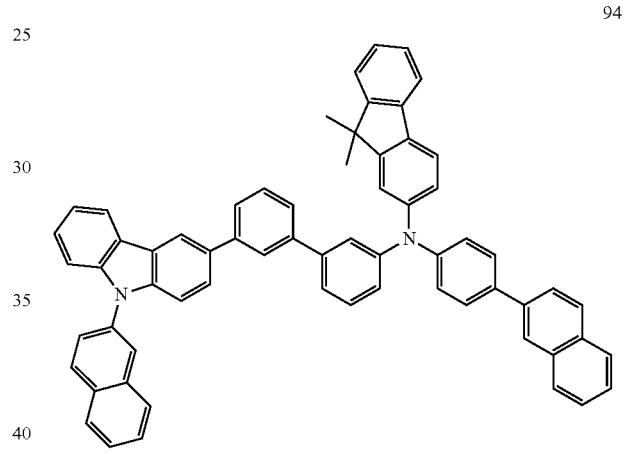
92
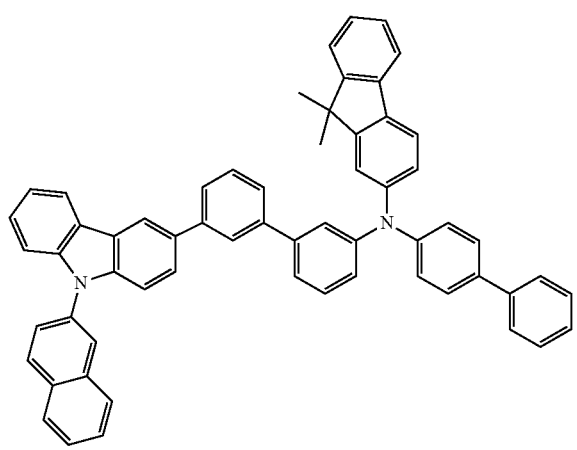
95

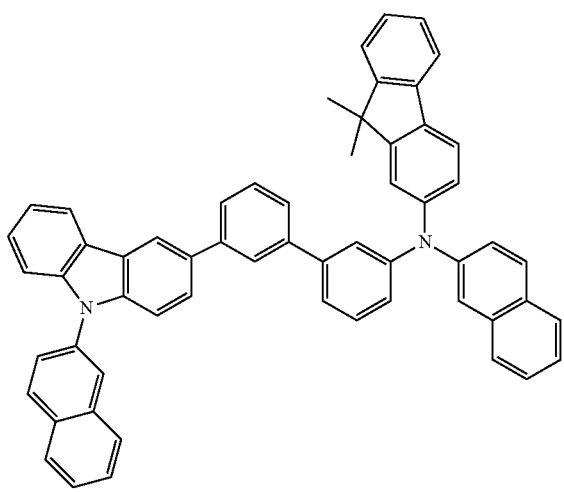

96

According to an embodiment, the first compound may be identical to the third compound, and the second compound may be identical to the fourth compound.

According to another embodiment, the first compound may be identical to the second compound, and the third compound may be identical to the fourth compound.

The first charge-generation material and the second charge-generation material may each independently be selected from a quinone derivative, a metal oxide, or a compound containing a cyano group.

For example, the first charge-generation material and the second charge-generation material may each independently be selected from tetracyanoquinonedimethane (TCNQ), 2,3,5,6-tetrafluoro-tetracyano-1,4-benzoquinonedimethane (F4-TCNQ) or Compound 501 below:

<Compound 501>

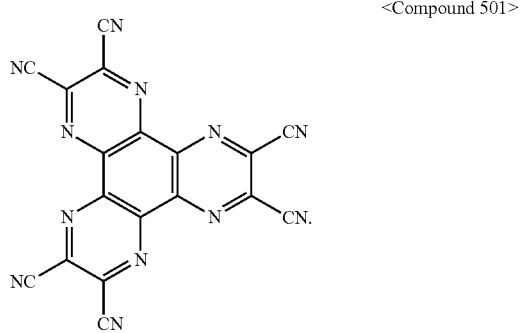 [SMILES: N#Cc1nc2c3nc(C#N)c(C#N)nc3c3nc(C#N)c(C#N)nc3c2nc1C#N]

The first hole transport layer 141 may contact the second hole transport layer 142. When the first hole transport layer 141 contacts the second hole transport layer 142, a charge balance may improve.

The third hole transport layer 143 may contact the fourth hole transport layer 144. When the third hole transport layer 143 contacts the fourth hole transport layer 144, a charge balance may improve.

The buffer layer 150 may be formed on the fourth hole transport layer 144. When the buffer layer 150 is formed using vacuum deposition or spin coating, the deposition and coating conditions may be similar to those for the formation of the hole injection layer 130, though the deposition and coating conditions may vary according to a compound that is used to form the buffer layer 150.

As a material for forming the buffer layer 150, the first compound may be used. As another example, the material for forming the buffer layer 150 may be the fourth compound. As another example, for use as the material for forming the buffer layer 150, the fourth compound and a luminescent host material may be mixed, and may have a value between a HOMO (highest occupied molecular orbital) energy potential of the fourth hole transport layer 144 and a HOMO energy potential of the emission layer 160 to decrease a driving voltage. An energy potential of the buffer layer 150 may be in a range of about 5.4 eV to about 5.9 eV. The material for forming the buffer layer 150 may be a material that has lower electron mobility and more rigidity than a hole transport material.

A thickness of the buffer layer 150 may be in a range of about 1 nm to about 20 nm. For example, a thickness of the buffer layer 150 may be in a range of about 5 nm to about 10 nm. Maintaining the thicknesses of the buffer layer 150 within this range may help improve, without a substantial increase in driving voltage, efficiency of an organic light-emitting diode due to the compensation for an optical resonance distance according to the wavelength of light emitted from an emission layer 160.

The emission layer 160 may be formed on the buffer layer 150. When the emission layer 160 is formed by vacuum deposition or spin coating, the deposition or coating conditions may be similar to those applied to form the hole injection layer 130, although the deposition or coating conditions may vary according to the material that is used to form the emission layer 160.

The emission layer 160 may include a host and a dopant. Examples of a host are Alq$_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl)anthracene (TBADN), E3, distyrylarylene (DSA), dmCBP (see the following chemical structure), and Compounds 501 to 509 illustrated below:

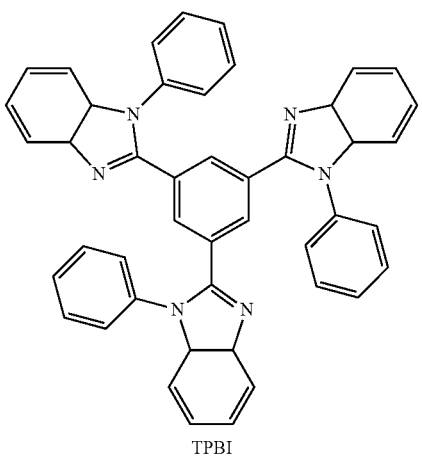

TPBI

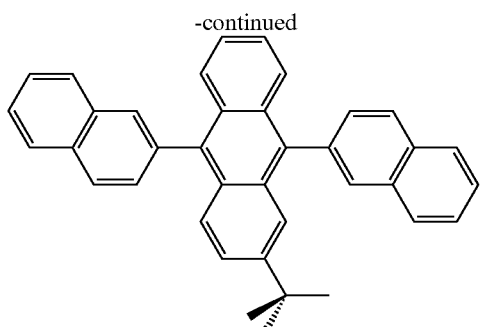
TBADN
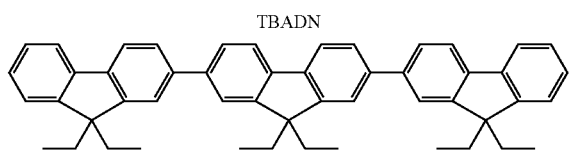
E3
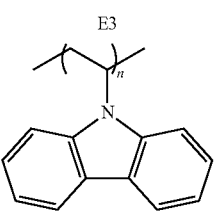
PVK
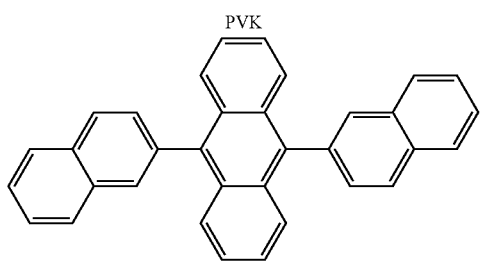
ADN
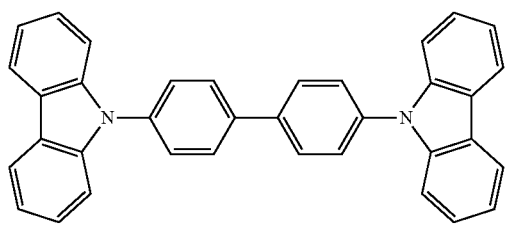
CBP
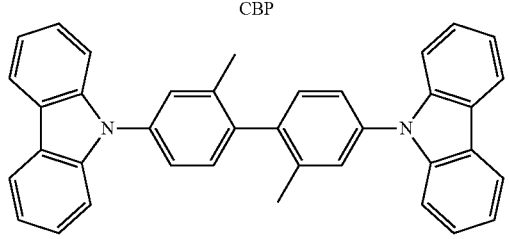
dmCBP
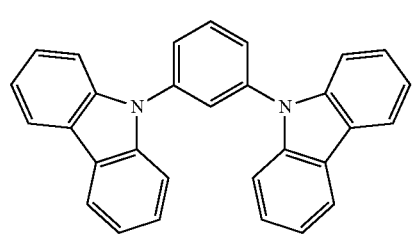
501
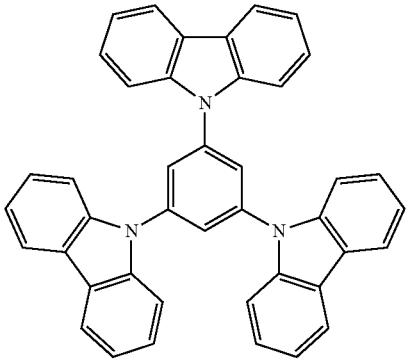
502
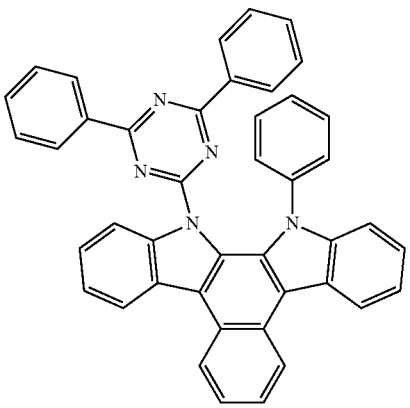
503
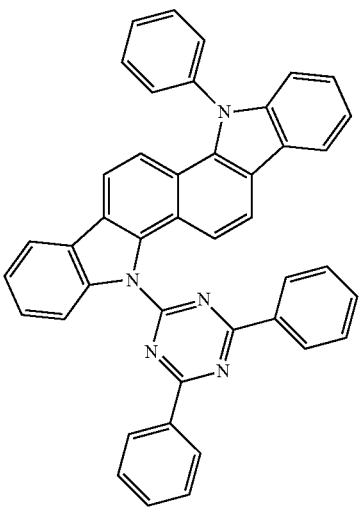
504

-continued

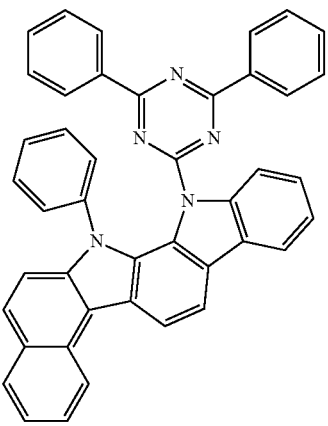
505

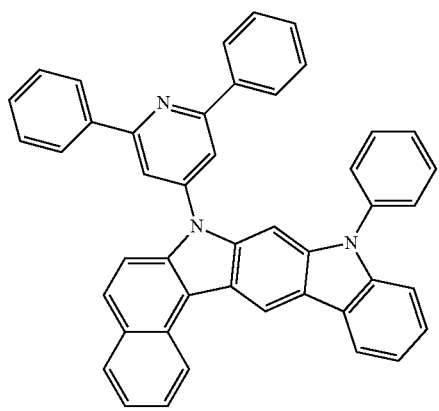
506

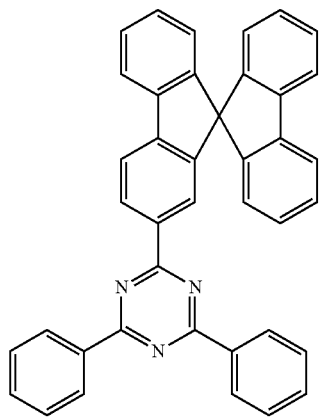
507

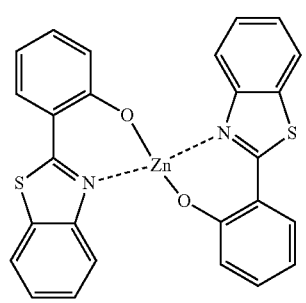
508

-continued

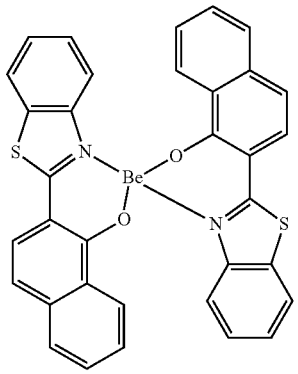
509

In an embodiment, the host may be an anthracene-based compound represented by Formula 400 below:

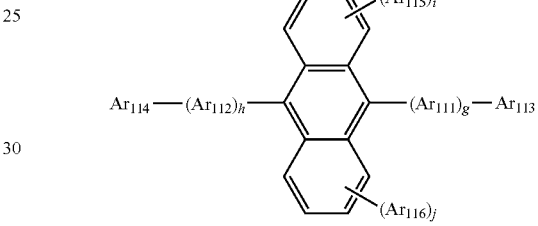
<Formula 400> wherein, in Formula 400, $Ar_{111}$ and $Ar_{112}$ may each independently be a substituted or unsubstituted $C_6$-$C_{60}$ arylene group; $Ar_{113}$ to $Ar_{116}$ may each independently be a substituted or unsubstituted $C_1$-$C_{10}$ alkyl group, or a substituted or unsubstituted $C_6$-$C_{60}$ aryl group; and g, h, I, and j are each independently an integer of 0 to 4.

For example, $Ar_{111}$ and $Ar_{112}$ in Formula 60 may each independently be a phenylene group, a naphthylene group, a phenanthrenyl group, or a pyrenylene group; or a phenylene group, a naphthylene group, a phenanthrenyl group, a fluorenyl group, or a pyrenylene group, each substituted with at least one of a phenyl group, a naphthyl group, and an anthryl group.

g, h, i, and j in Formula 60 may each be independently 0, 1, or 2.

$Ar_{113}$ to $Ar_{116}$ in Formula 400 may each independently be a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; or a phenyl group, a naphthyl group, an anthryl group, a pyrenyl group, a phenanthrenyl group, and a fluorenyl group, each substituted with at least one of a deuterium atom, a halogen atom, a hydroxyl group, a cyano group, a nitro group, an amino group, an amidino group, a hydrazine, a hydrazone, a carboxyl group or salt thereof, a sulfonic group or salt thereof, a phosphoric acid group or salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, pyrenyl group, a phenanthrenyl group, a fluorenyl group, and

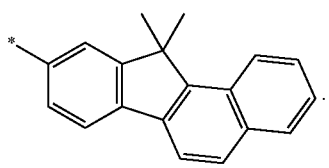 [SMILES: *c1ccc2c(c1)C(C)(C)c1c-2ccc2ccccc12]
For example, the anthracene-based compound represented by Formula 400 may be one of the following compounds:
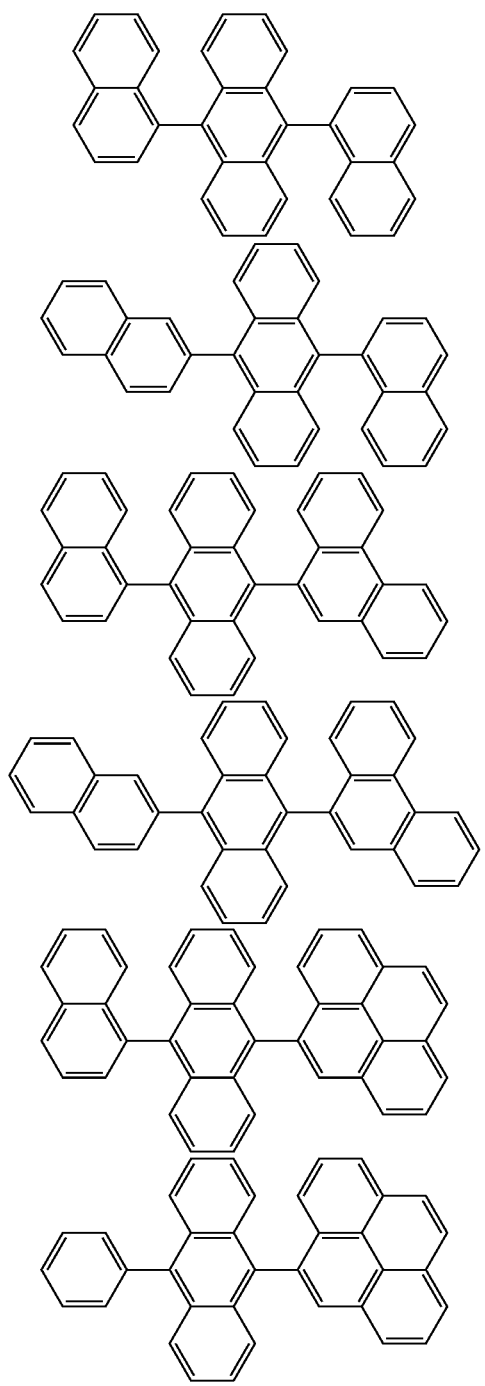
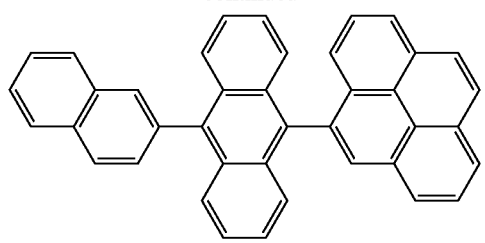
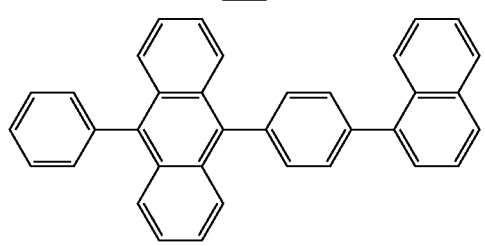
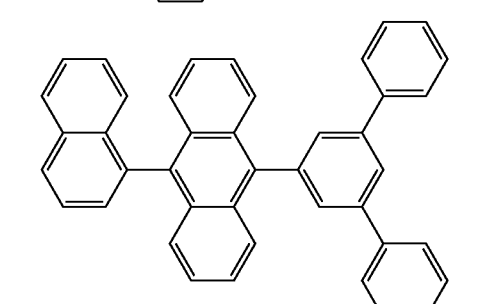
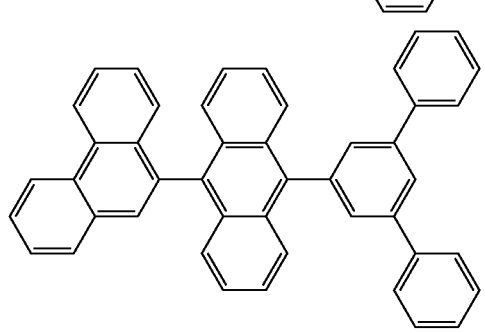
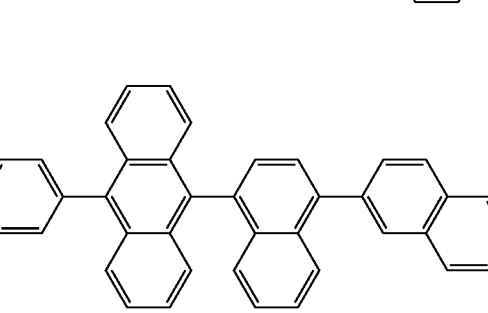
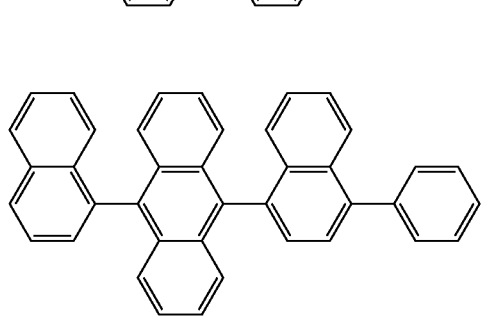

75
-continued
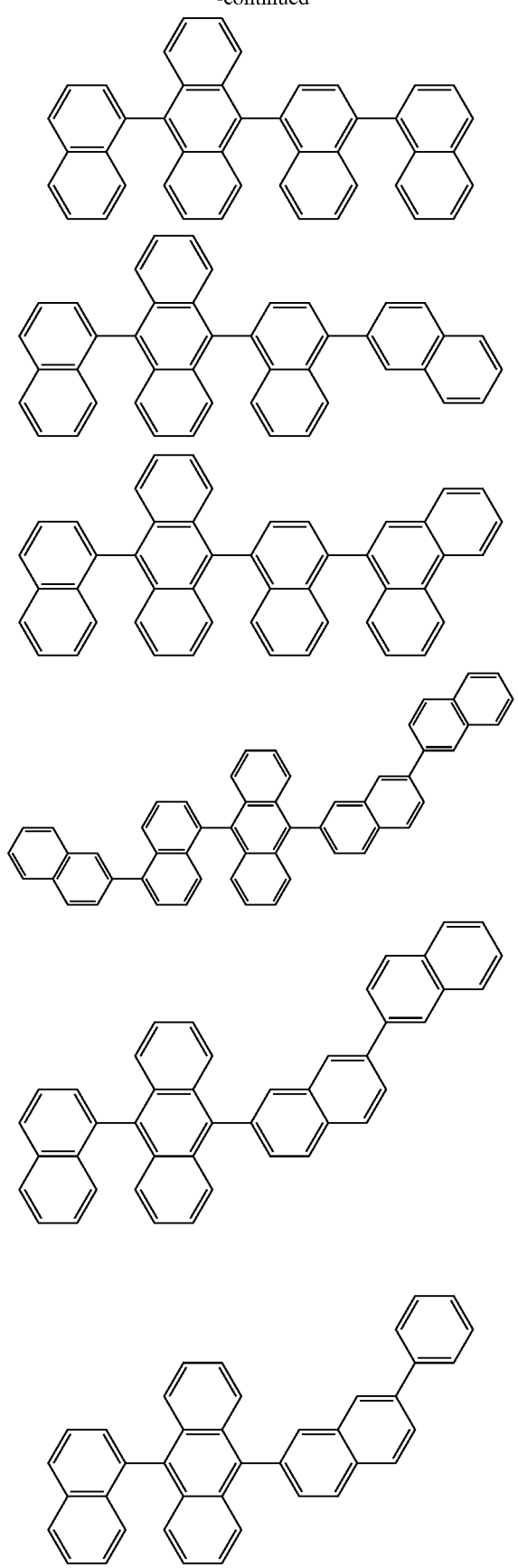
76
-continued
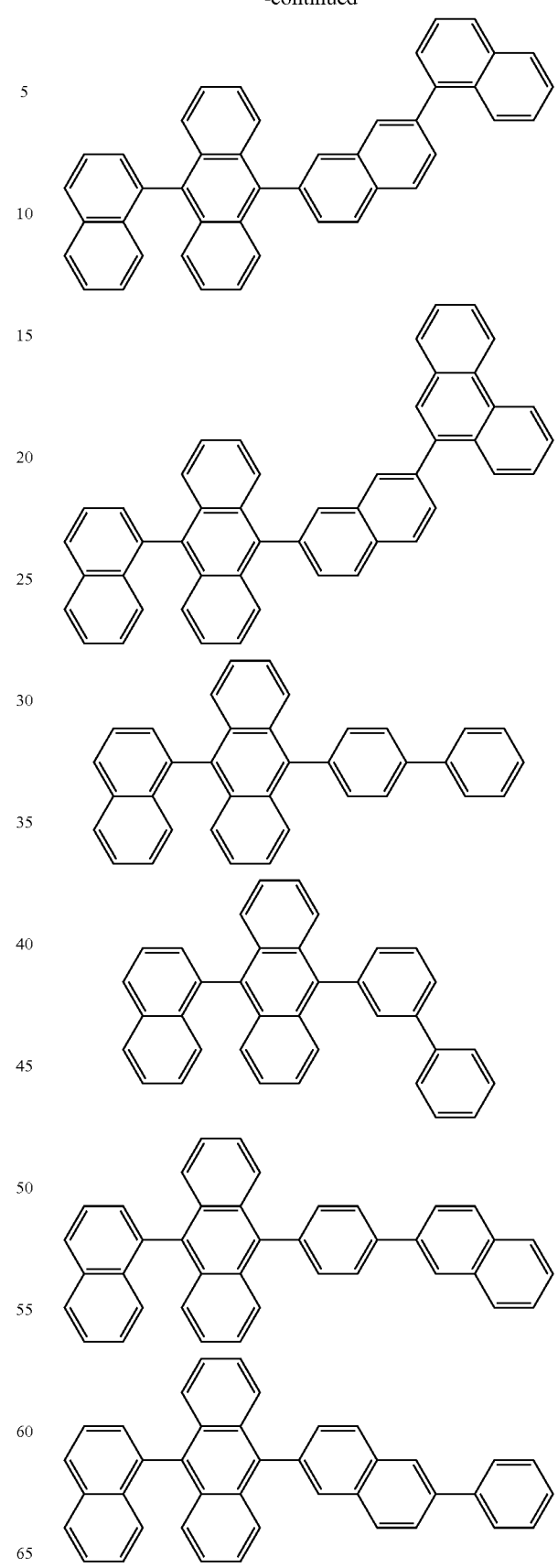

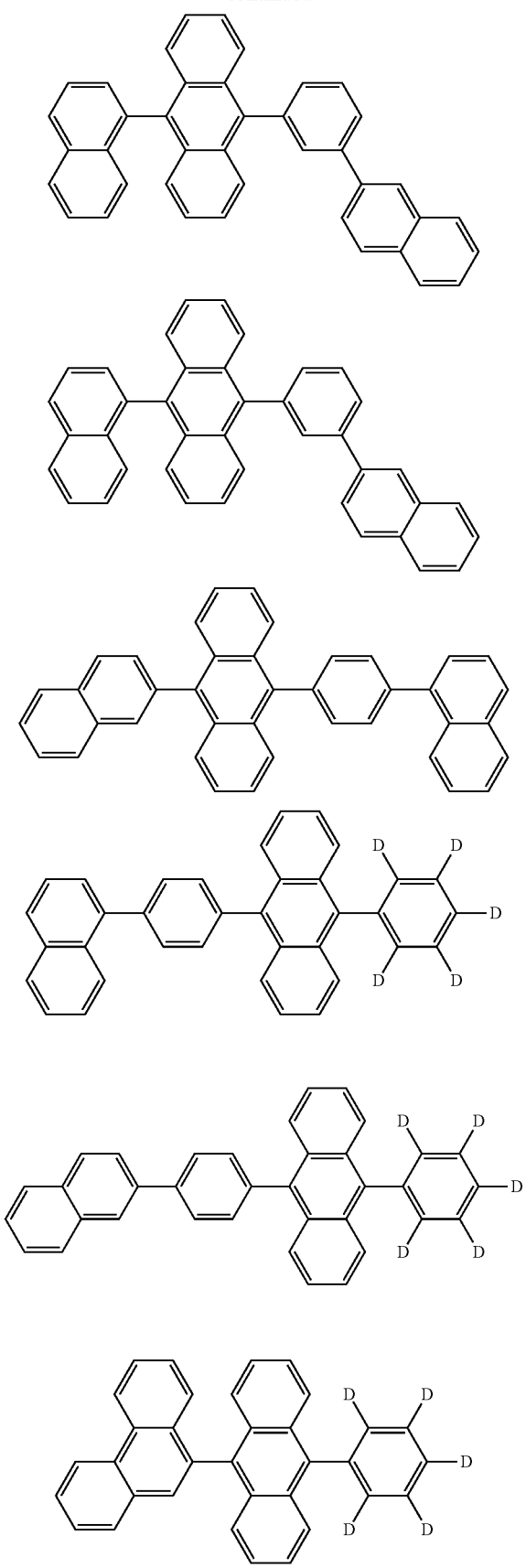
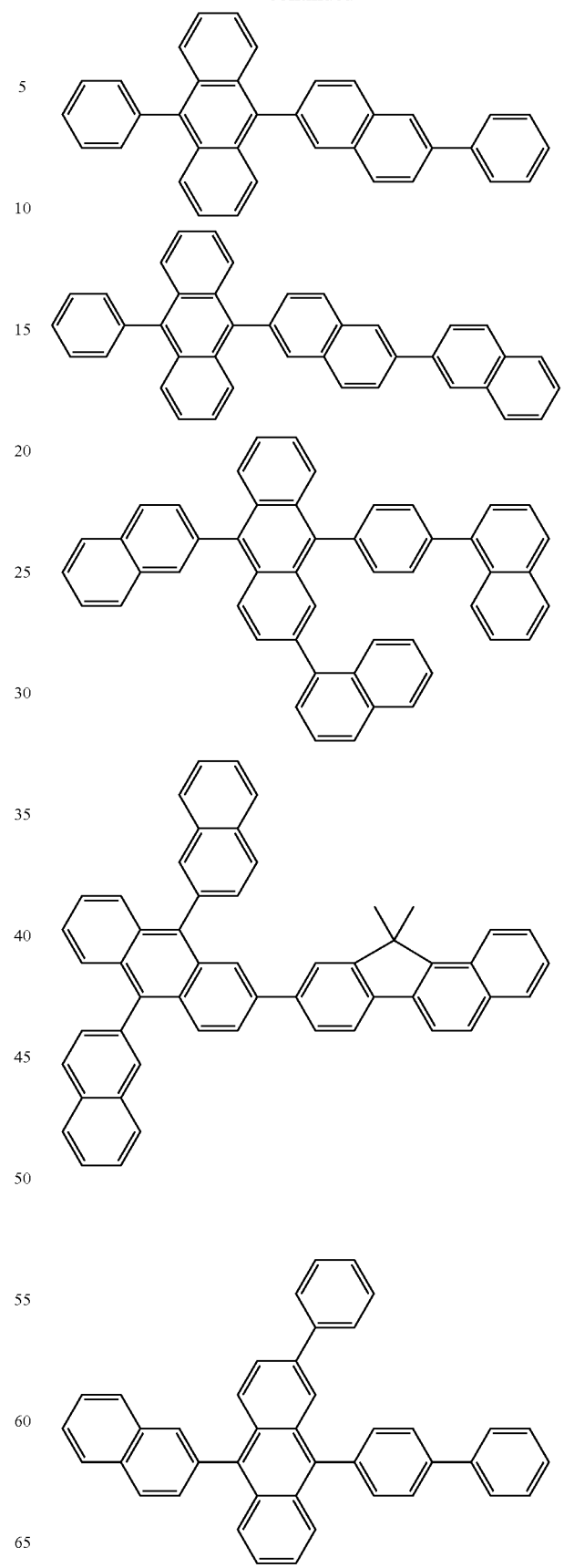

-continued

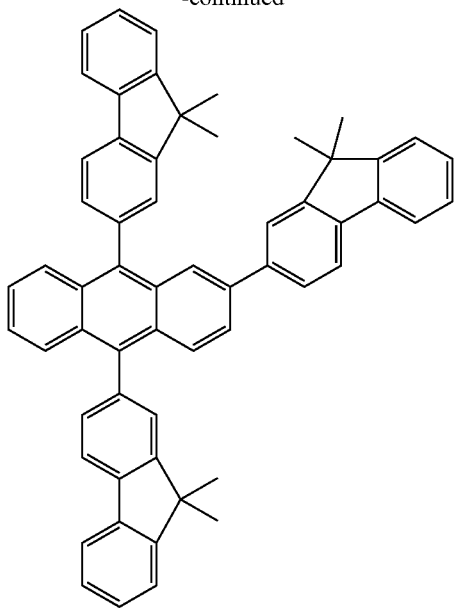

In an embodiment, the host may be an anthracene-based compound represented by Formula 401 below:

<Formula 401>

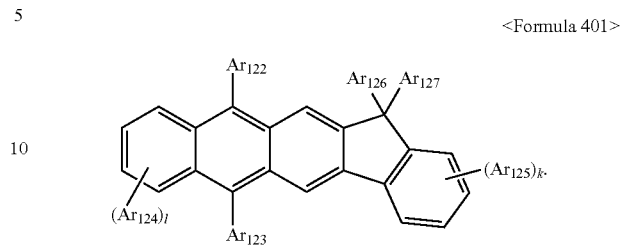

$Ar_{122}$ to $Ar_{125}$ in Formula 401 are the same as described in detail in connection with $Ar_{113}$ in Formula 400.

$Ar_{126}$ and $Ar_{127}$ in Formula 401 may each independently be a $C_1$-$C_{10}$ alkyl group (for example, a methyl group, an ethyl group, or a propyl group).

k and l in Formula 401 may each independently be an integer of 0 to 4. For example, k and l may be 0, 1, or 2.

For example, the anthracene-based compound represented by Formula 401 may be one of the following compounds:

81
-continued

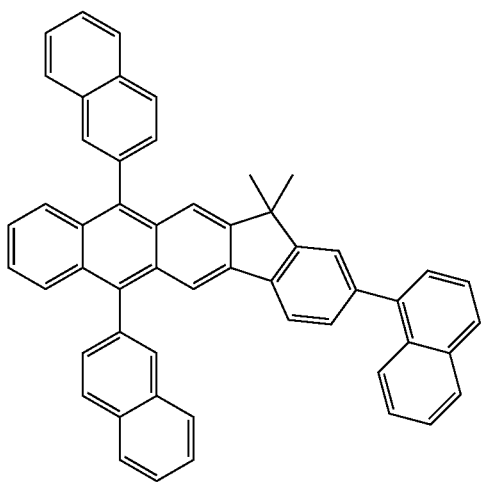

82
-continued

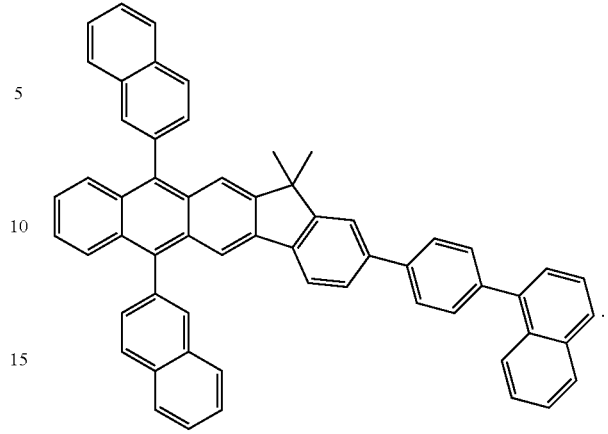

The dopant may be at least one of a fluorescent dopant and a phosphorescent dopant. The dopant may be selected from an anthracene-based compound, an arylamine-based compound, and a styryl-based compound.

For example, a blue dopant may be selected from terfluorene and compounds illustrated below:

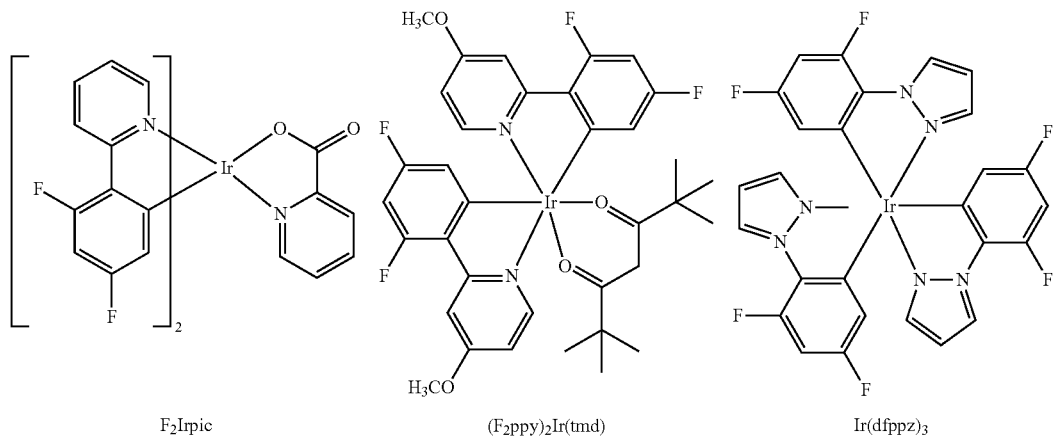

F₂Irpic      (F2ppy)₂Ir(tmd)      Ir(dfppz)₃

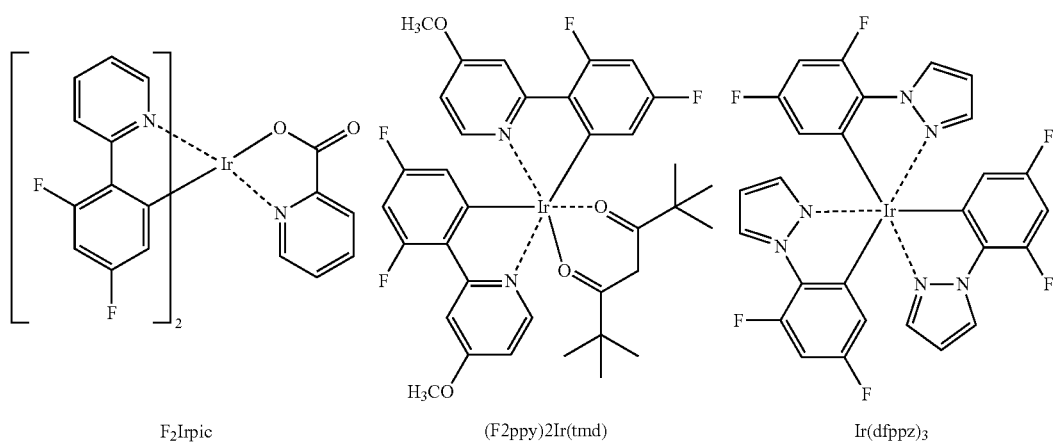

F₂Irpic      (F2ppy)2Ir(tmd)      Ir(dfppz)₃

83
-continued
84
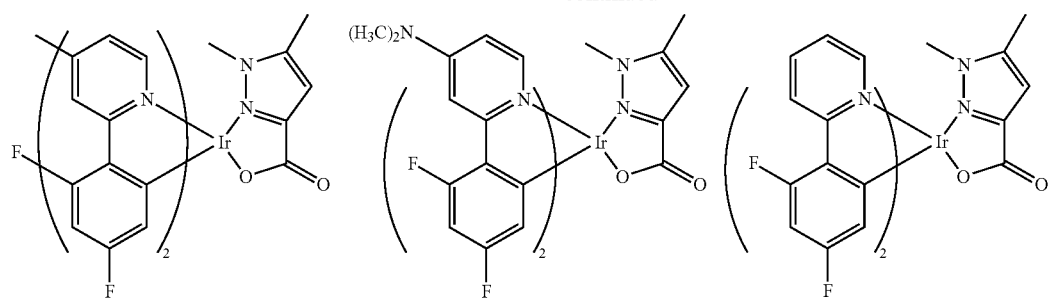
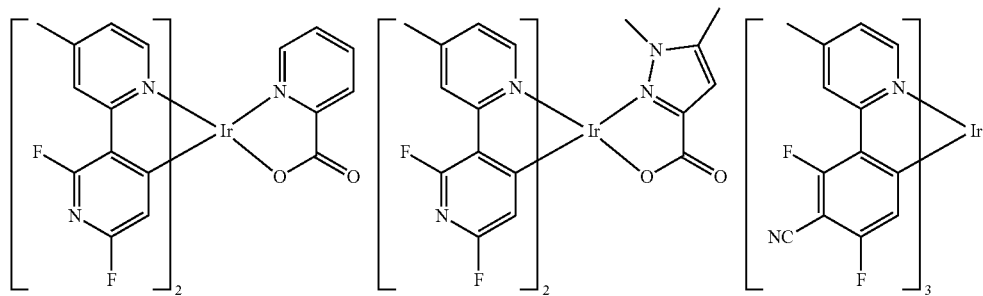
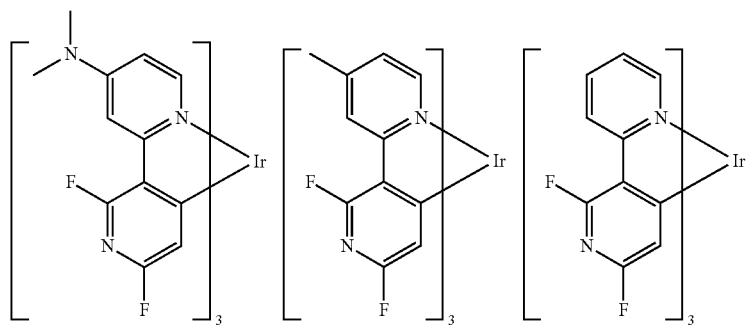
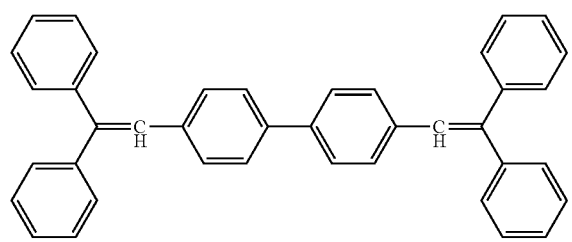
DPVBi
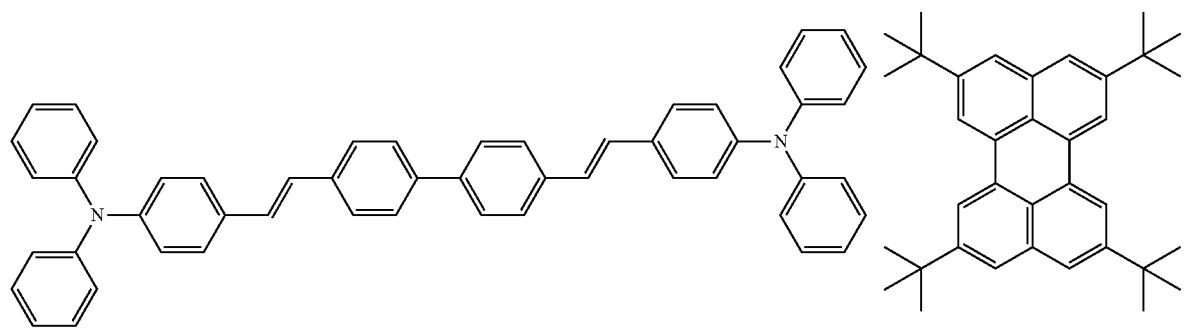
DPAVBi
TBPe For example, a red dopant may be selected from compounds illustrated below:
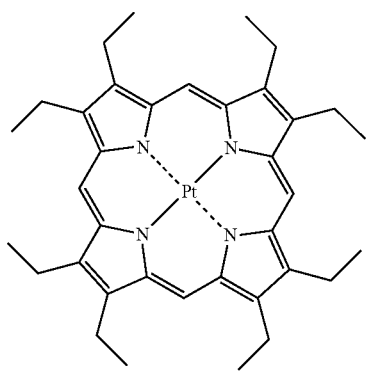
PtOEP
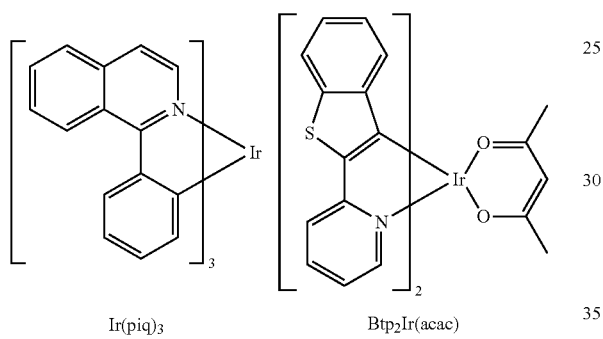
Ir(piq)₃  Btp₂Ir(acac)
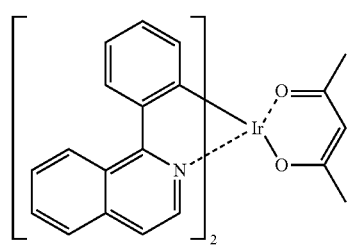
Ir(pq)₂(acac)
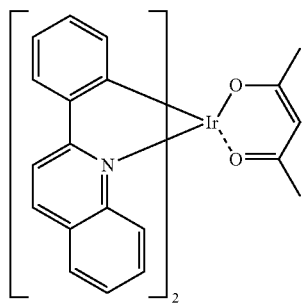
Ir(pq)₂(acac)
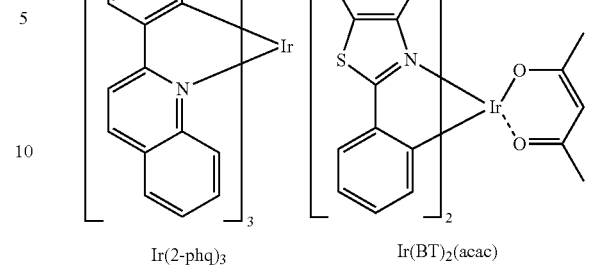
Ir(2-phq)₃  Ir(BT)₂(acac)
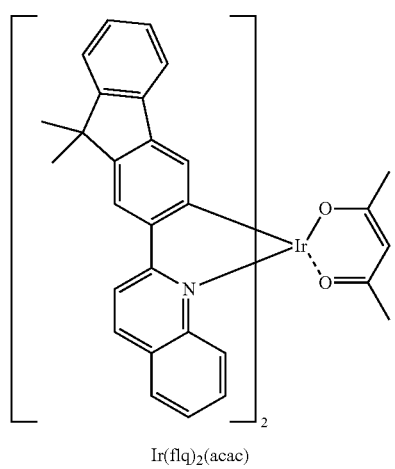
Ir(flq)₂(acac)
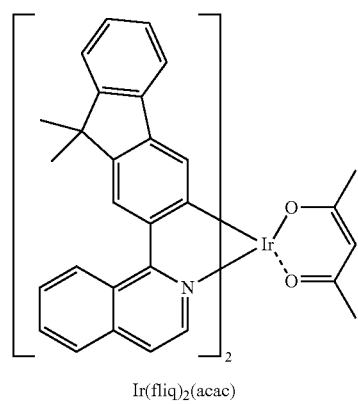
Ir(fliq)₂(acac)
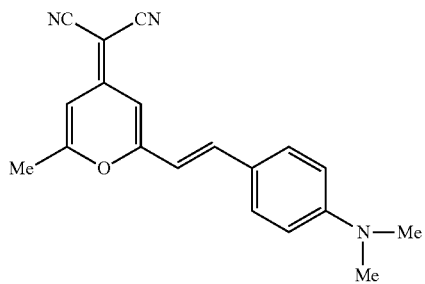
DCM -continued
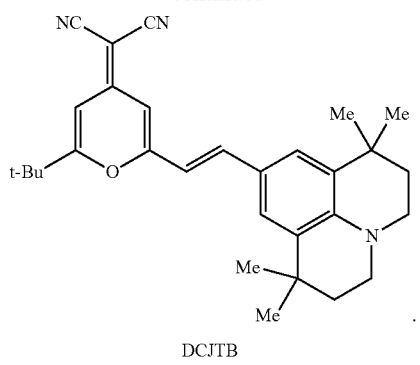 [SMILES: CC(C)(C)C1=CC(=C(C#N)C#N)C=C(/C=C/c2cc3c4c(c2)C(C)(C)CCN4CCC3(C)C)O1]
DCJTB
For example, a green dopant may be selected from compounds illustrated below:
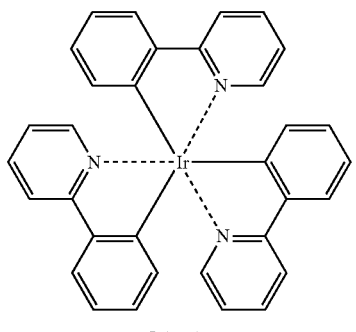
Ir(ppy)$_3$
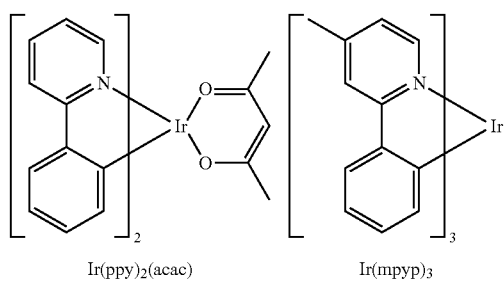
Ir(ppy)$_2$(acac)    Ir(mpyp)$_3$
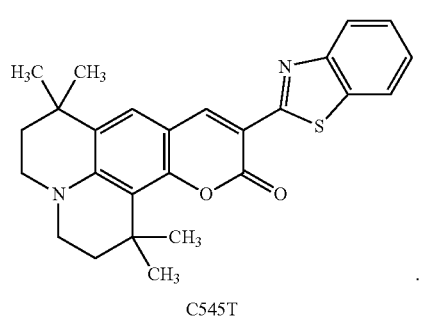
C545T
In an embodiment, a dopant available for use in the emission layer 160 may be an organo-metallic complex illustrated below:
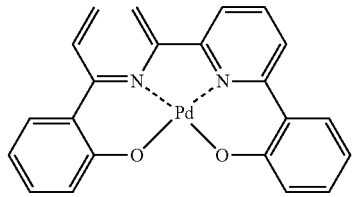
D1
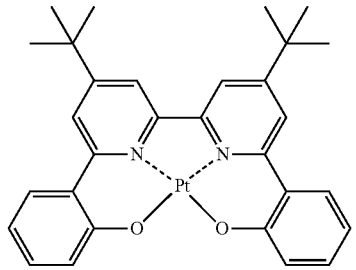
D2
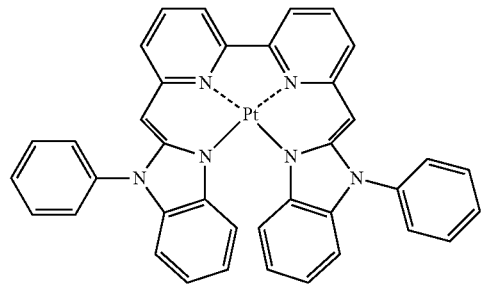
D3
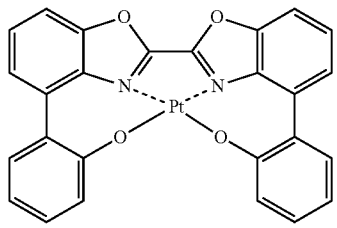
D4
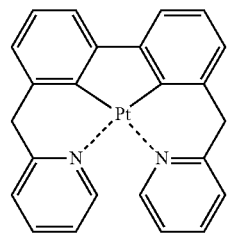
D5
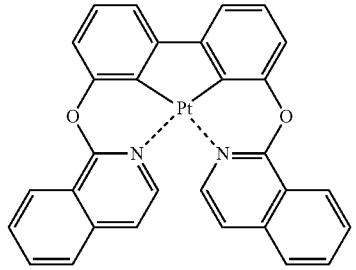
D6

D7 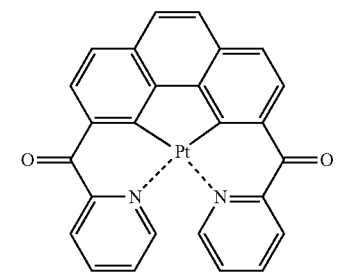
D8 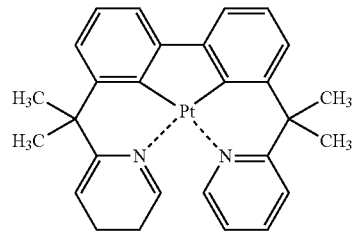
D9 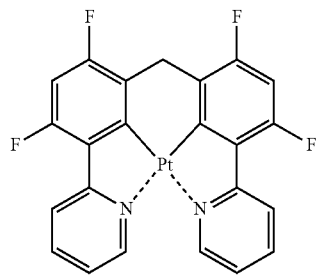
D10 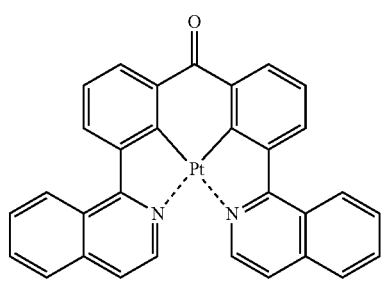
D11 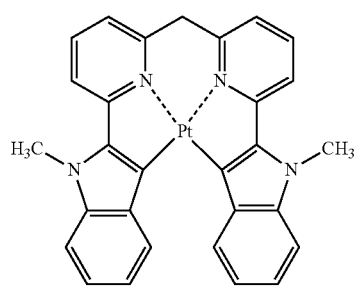
D12 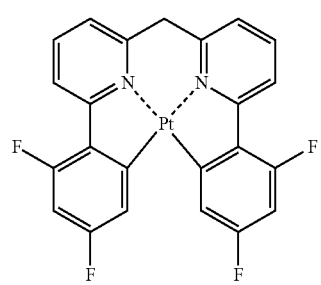
D13 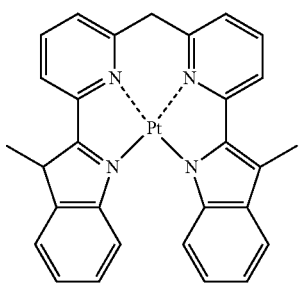
D14 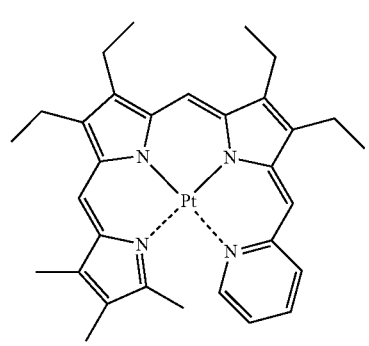
D15 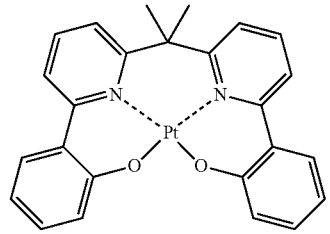
D16 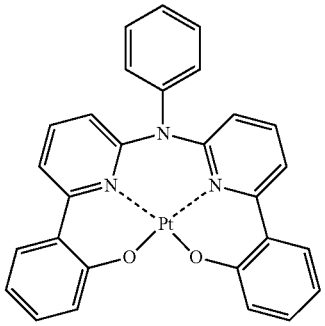
D17 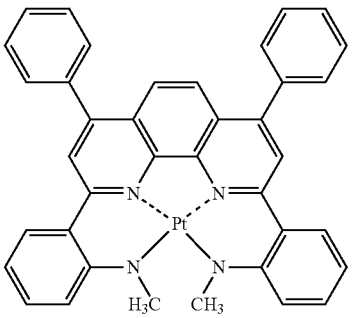

-continued
D18
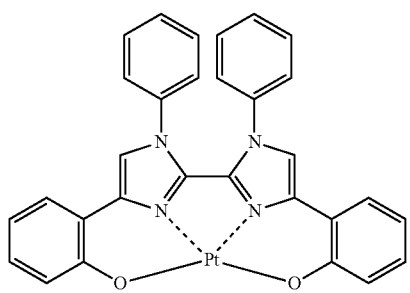
D19
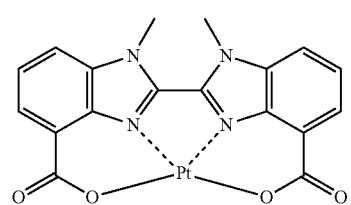
D20
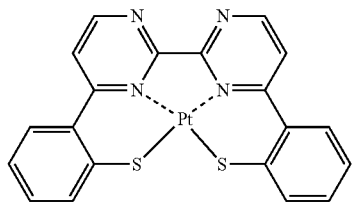
D21
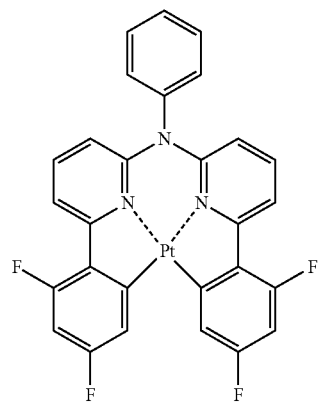
D22
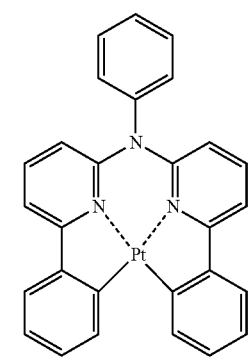
-continued
D23
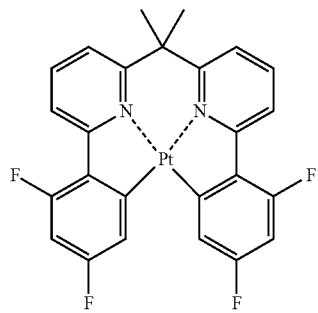
D24
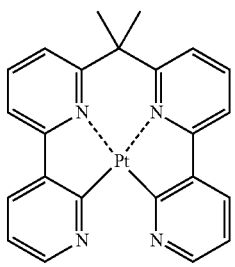
D25
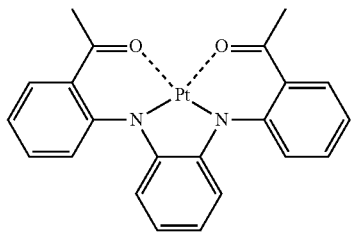
D26
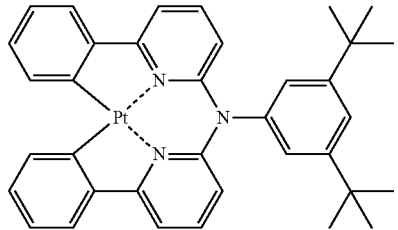
D27
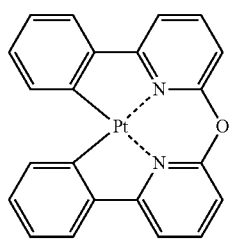
D28
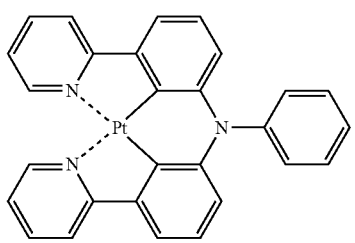

-continued
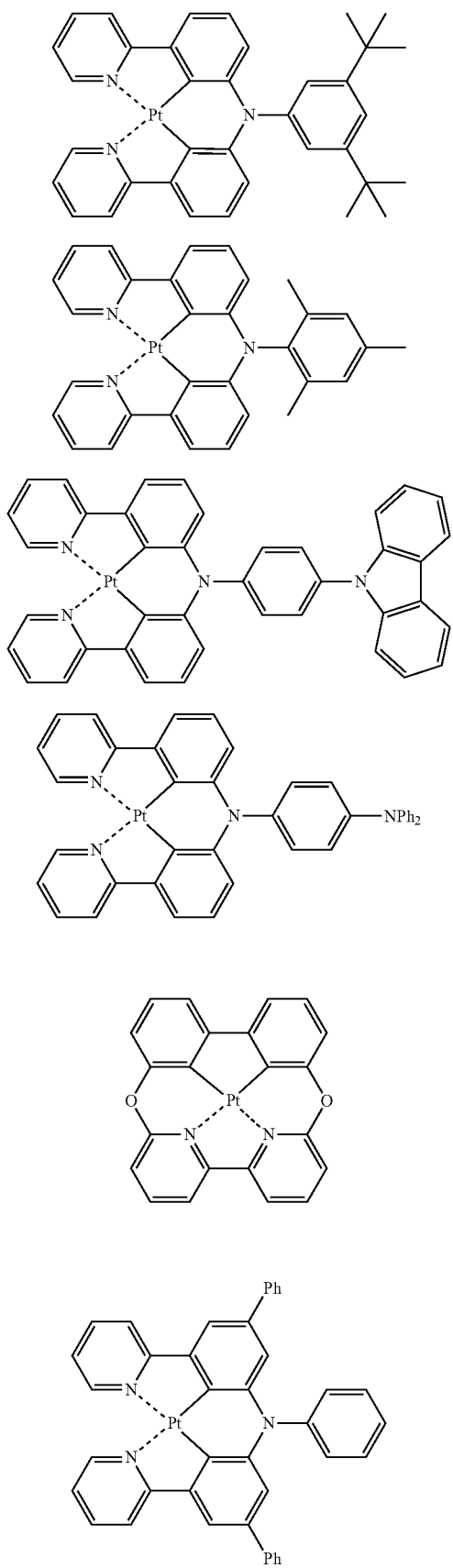
D29
D30
D31
D32
D33
D34
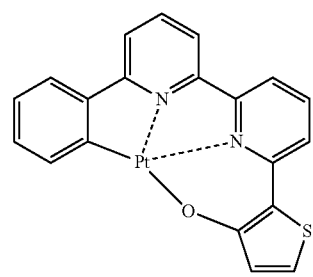
D35
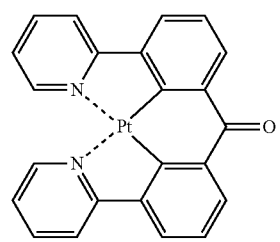
D36
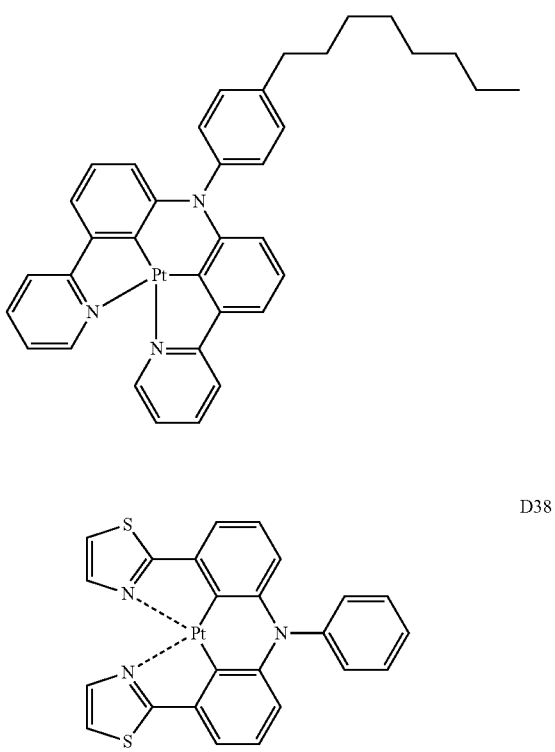
D37
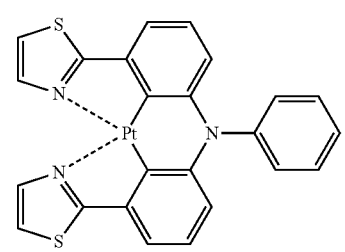
D38
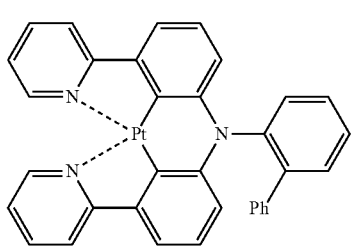
D39

-continued
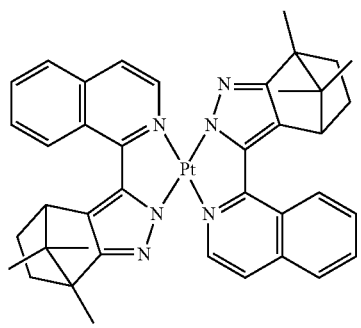
D40
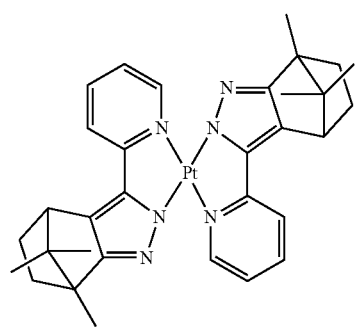
D41
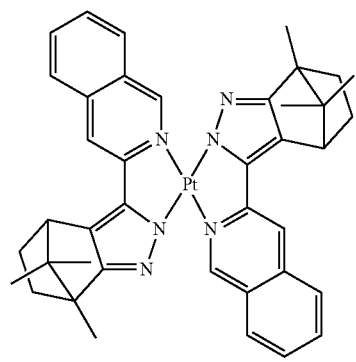
D42
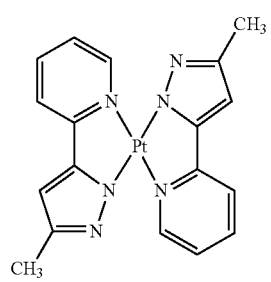
D43
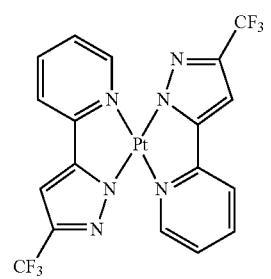
D44
-continued
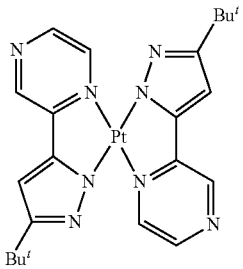
D45
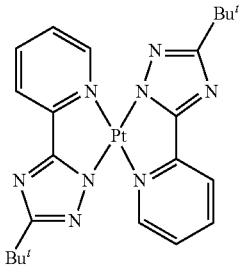
D46
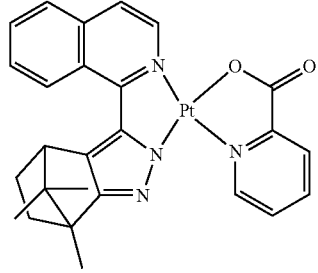
D47
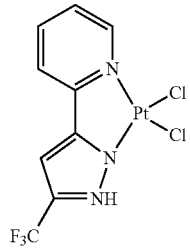
D48
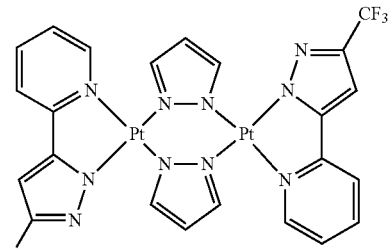
D49
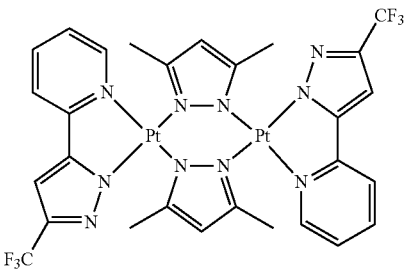
D50

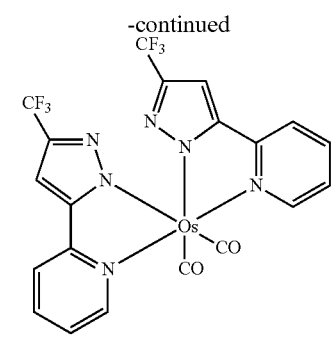

Os(fppz)₂(CO)₂

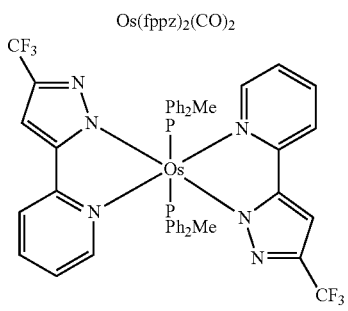

Os(fppz)₂(PPh₂Me)₂

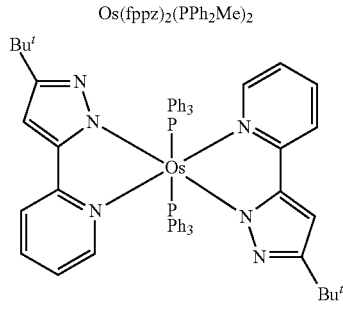

Os(bppz)₂(PPh₃)₂

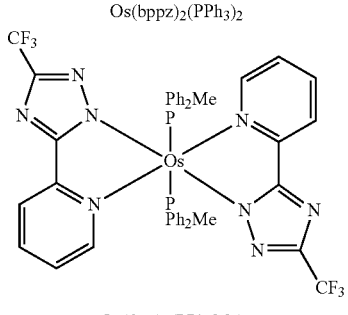

Os(fptz)₂(PPh₂Me)₂

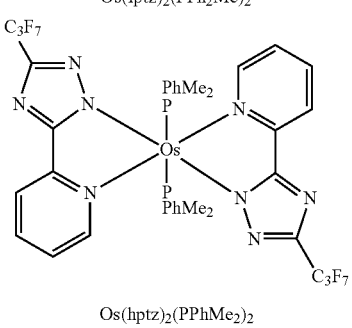

Os(hptz)₂(PPhMe₂)₂

When the emission layer 160 includes a host and a dopant, an amount of the dopant may be, for example, in a range of about 0.01 to about 15 wt % based on 100 wt % of the emission layer 160.

A thickness of the emission layer 160 may be in a range of about 200 Å to about 700 Å. Maintaining the thickness of the emission layer 160 is within this range may help provide excellent light-emission characteristics without a substantial increase in driving voltage.

When the organic light-emitting diode 100 is a full color organic light-emitting device, the emission layer may be patterned into a red emission layer, a green emission layer, and a blue emission layer, according to a sub pixel.

In some embodiments, the emission layer 160 may have a multi-layered structure of a red emission layer, a green emission layer, and a blue emission layer, or may include a red-light emission material, a green-light emission material, and a blue-light emission material, which are mixed with each other in a single layer, to emit white light. In an embodiment, the organic light-emitting diode 100 including the emission layer 160 may emit full-color, and may include a red emission layer, a green emission layer, and a blue emission layer.

Next, an electron transport layer 170 (ETL) is formed on the emission layer by using various methods, for example, by vacuum deposition, spin coating, or casting. When the electron transport layer 170 is formed using vacuum deposition or spin coating, the deposition and coating conditions may be similar to those for the formation of the hole injection layer, though the conditions for deposition and coating may vary according to the material that is used to form the electron transport layer.

A material for forming the electron transport layer 170 may stably transport electrons injected from an electron injection electrode (cathode). Exemplary electron transport material include a quinoline derivative, such as tris(8-quinolinolate)aluminum (Alq₃), 3-(biphenyl-4-yl)-5-(4-tert-butylphenyl)4-phenyl-4H-1,2,4-triazole (TAZ), aluminum (III) bis(2-methyl-8-hydroxyquinoline)-4-phenylphenolate (Balq), berylium bis(benzoquinoli-10-noate) (Bebq₂), 9,10-di(naphthalene-2-yl)anthracene (AND), Compound 101, Compound 102, and 4,7-diphenyl-1,10-phenanthroline (BPhen):

<Compound 101>

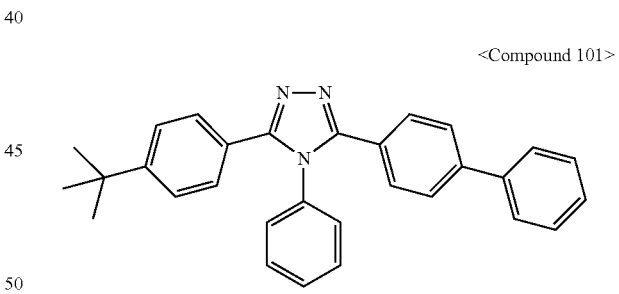

TAZ

<Compound 102>

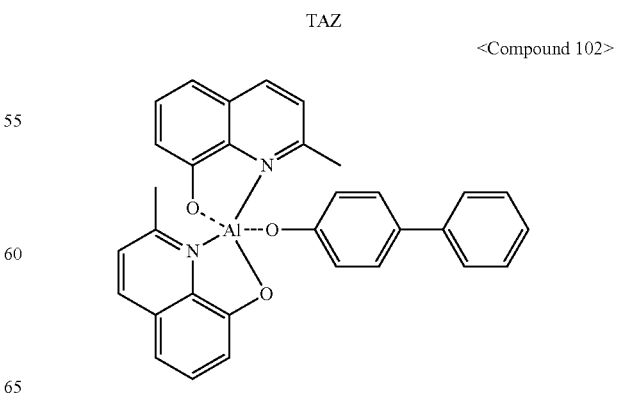

BAlq

-continued

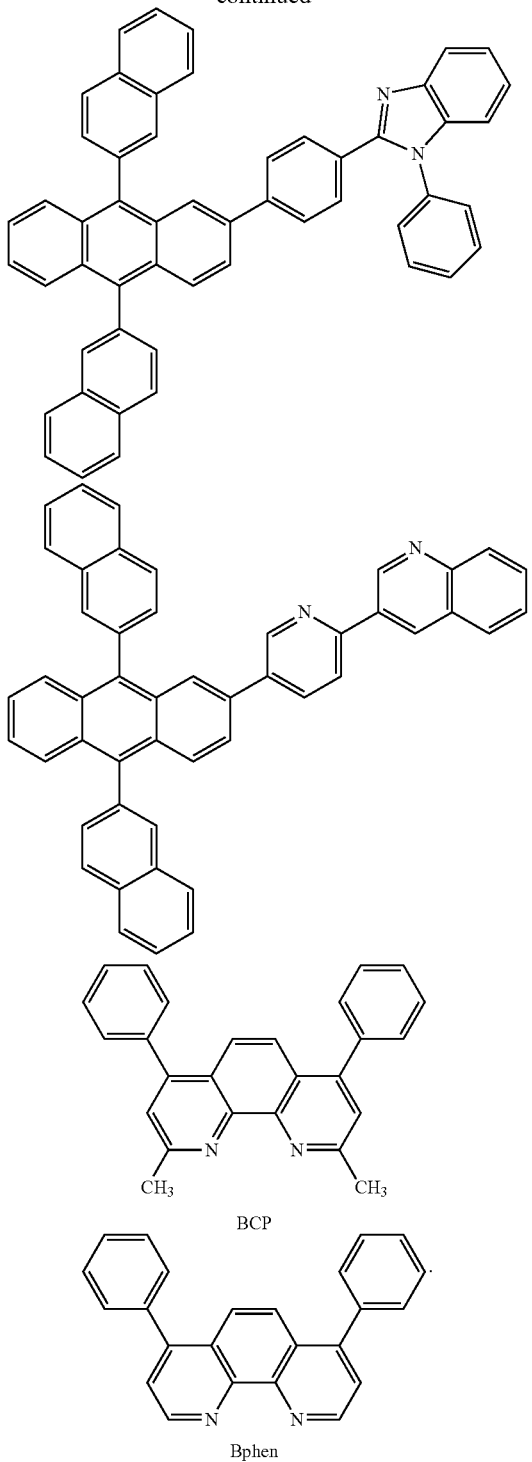

BCP

Bphen

A thickness of the electron transport layer 170 may be in a range of about 100 Å to about 1000 Å, for example, about 150 Å to about 500 Å. Maintaining the thickness of the electron transport layer 170 within the range described above may help provide the electron transport layer 170 with satisfactory electron transportation characteristics without a substantial increase in driving voltage.

In an embodiment, the electron transport layer 170 may further include, in addition to an electron transport organic compound, a metal-containing material. The metal-containing material may include a Li complex. Examples of the Li complex include lithium quinolate (Liq) and Compound 203 illustrated below:

<Compound 203>

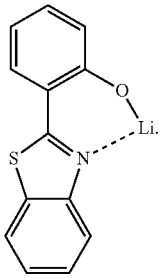

Then, the electron injection layer 180 (EIL), which facilitates injection of electrons from a cathode, may be formed on the electron transport layer. Any suitable electron-injecting material may be used to form the electron injection layer 180.

Examples of materials for forming the electron injection layer 180 including LiF, NaCl, CsF, $Li_2O$, and BaO. The deposition conditions of the electron injection layer 180 may be similar to those used to form the hole injection layer 130, although the deposition conditions may vary according to the material that is used to form the electron injection layer 180.

A thickness of the electron injection layer 180 may be in a range of about 1 Å to about 100 Å, for example, about 3 Å to about 90 Å. Maintaining the thickness of the electron injection layer 180 within the range described above may help provide the electron injection layer 180 with satisfactory electron transportation characteristics without a substantial increase in driving voltage.

A second electrode 190 may be disposed on the electron injection layer 180. The second electrode 190 may be a cathode that is an electron injection electrode. In an embodiment, a material for forming the second electrode 190 may be, for example, a material having a low work function, such as a metal, an alloy, an electrically conductive compound, or a mixture thereof. Examples of the second electrode 190 include lithium (Li), magnesium (Mg), aluminum (Al), aluminum-lithium (Al—Li), calcium (Ca), magnesium-indium (Mg—In), and magnesium-silver (Mg—Ag), and these materials may be formed as a thin film for use as a transmissive electrode. To manufacture a top emission type light-emitting device, a transmissive electrode formed using ITO or IZO may be formed.

An organic light-emitting device including a plurality of hole transport layers, as described above, may include "a first hole transport layer including a first compound and a first charge-generation material/a second hole transport layer including a second compound/a third hole transport layer including a third compound and a second charge-generation material/a fourth hole transport layer including a fourth compound".

The first compound, the second compound, the third compound, and the fourth compound may each independently be selected from compounds represented by Formula 1 or 2.

The compound represented by Formula 1 or 2 has a second benzene linked to a meta position of a first benzene that is linked to a carbazol-based ring in relation to a first carbon of the first benzene linked to the carbazol-based ring.

Accordingly, compared to a case in which the second benzene is linked to a para position of the first benzene linked to the carbazol-based ring in relation to the first carbon linked to the carbazol-based ring, the former case may have a lower HOMO energy level (based on an actually calculated value) and a slower hole mobility. Hole mobility may be faster than electron mobility, and in an emission layer of an organic light-emitting device in which the compound represented by Formula 1 or 2 is employed in a hole transport region between an anode and an emission layer, hole mobility and electron mobility may strike a balance. Also, the leakage of electrons provided from a second electrode (cathode) from an emission layer to a hole transport layer may be prevented. Accordingly, in an embodiment, a hole transport region includes the compound represented by Formula 1 or 2, and an organic light-emitting device including such a hole transport region may have high efficiency and a long lifespan (see Formulae 1' and 2' below).

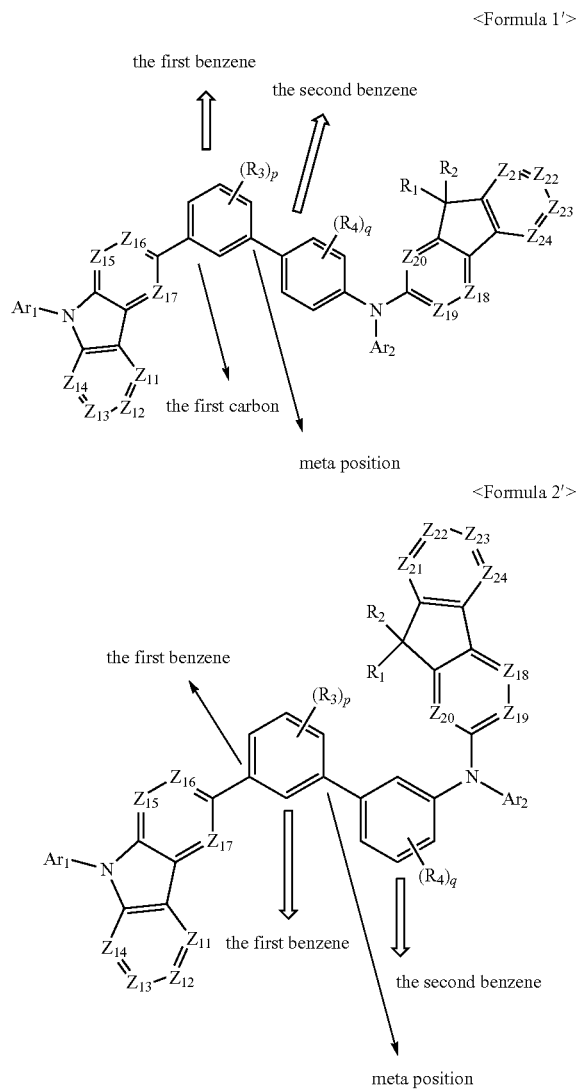

Thus, an organic light-emitting device including a hole transport layer including the compound represented by Formula 1 or 2 may have high efficiency, high brightness, and long lifetime.

Using of a plurality of hole transport layers may help control hole mobility and hole injection characteristics. Accordingly, exciton formation characteristics of an emission layer may be improved and thus, a formed organic light-emitting device may have high efficiency and long lifespan. Also, using of a plurality of hole transport layers may help lower a change in hole transport characteristics (dependency on a hole transport material) according to a hole transport material.

Figure 2:
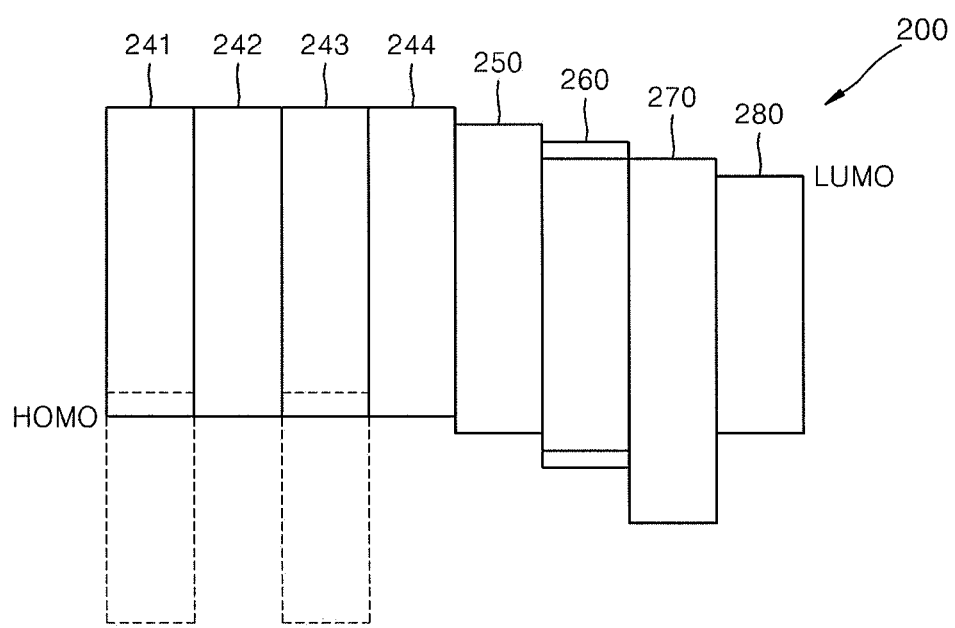
FIG. 2 illustrates a schematic diagram showing energy relationships between layers that constitute an organic light-emitting device according to an embodiment.

FIG. 2 illustrates energy levels of an organic light-emitting device 200 according to an embodiment.

The organic light-emitting device 200 includes a first hole transport layer 241, a second hole transport layer 242, a third electron transport layer 243, a fourth electron transport layer 244, a buffer layer 250, an emission layer 260, an electron transport layer 270, and an electron injection layer 280. The first hole transport layer 241 includes a first compound and a first charge-generation material, and the third electron transport layer 243 includes a third compound and a second charge-generation material, and accordingly, the first hole transport layer 241 and the third electron transport layer 243 may have similar levels of HOMO energy potential and LUMO (lowest unoccupied molecular orbital) energy potential. The first hole transport layer 241 and the third electron transport layer 243 respectively include a first charge-generation material and a second charge-generation material, and HOMO energy potentials and LUMO energy potentials of the first and second hole transport layers 241 and 242 are indicated as a dotted line. The HOMO energy potentials and LUMO energy potentials of the first and second hole transport layers 241 and 242 are relatively too low, and thus, driving voltages of the first hole transport layer 241 and the third electron transport layer 243 may be lowered.

The second hole transport layer 242 includes a second compound and the fourth electron transport layer 244 includes a fourth compound, and accordingly, the second hole transport layer 242 and the fourth electron transport layer 244 may have similar levels of HOMO energy potential and LUMO energy potential.

The unsubstituted $C_1$-$C_{60}$ alkyl group (or $C_1$-$C_{60}$ alkyl group) used herein may be a $C_1$-$C_{60}$ linear or branched alkyl group, such as methyl, ethyl, propyl, isobutyl, sec-butyl, pentyl, iso-amyl, or hexyl, and the substituted $C_1$-$C_{60}$ alkyl group is obtained by substituting at least one hydrogen atom of the substituted $C_1$-$C_{60}$ alkyl group with one selected from a deuterium atom, a halogen atom, a hydroxyl group, a nitro group, a cyano group, an amino group, an amidino group, a hydrazine, a hydrazone, a carboxyl group or salt thereof, a sulfonic acid or salt thereof, a phosphoric acid or salt thereof, a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, —$N(Q_{11})(Q_{12})$, —$Si(Q_{13})(Q_{14})(Q_{15})$, and $B(Q_{16})(Q_{17})$ (wherein $Q_{11}$ to $Q_{17}$ are each independently selected from a hydrogen atom, a $C_1$-$C_{60}$ alkyl group, a $C_2$-$C_{60}$ alkenyl group, a $C_2$-$C_{60}$ alkynyl group, a $C_6$-$C_{60}$ aryl group, and a $C_2$-$C_{60}$ heteroaryl group).

The unsubstituted $C_1$-$C_{60}$ alkoxy group (or $C_1$-$C_{60}$ alkoxy group) used herein refers to a group represented by —OA (wherein A is the unsubstituted $C_1$-$C_{60}$ alkyl group described above), and detailed examples thereof are methoxy, ethoxy, and isopropyloxy, and one or more hydrogen atoms of these alkoxy groups may be substituted with the same substituents as described in connection with the substituted $C_1$-$C_{60}$ alkyl group.

The unsubstituted $C_2$-$C_{60}$ alkenyl group (or $C_2$-$C_{60}$ alkenyl group) used herein refers to an unsubstituted $C_2$-$C_{60}$ alkyl group having one or more carbon double bonds at a center or end thereof. Examples of the unsubstituted $C_2$-$C_{60}$ alkenyl group are an ethenyl group, a prophenyl group, and a butenyl group. One or more hydrogen atoms of these unsubstituted $C_2$-$C_{60}$ alkenyl groups may be substituted with the same substituents as described in connection with the substituted $C_1$-$C_{60}$ alkyl group.

The unsubstituted $C_2$-$C_{60}$ alkynyl group (or $C_2$-$C_{60}$ alkynyl group) used herein refers to an unsubstituted $C_2$-$C_{60}$ alkyl group having one or more carbon triple bonds at a center or end thereof. Examples of the unsubstituted $C_2$-$C_{60}$ alkynyl group are ethynyl, propynyl, and the like. One or more hydrogen atoms of these alkynyl groups may be substituted with the same substituents as described in connection with the substituted $C_1$-$C_{60}$ alkyl group.

The unsubstituted $C_6$-$C_{60}$ aryl group is a monovalent group having a carbocyclic aromatic system having 5 to 60 carbon atoms including at least one aromatic ring. The unsubstituted $C_6$-$C_{60}$ arylene group is a divalent group having a carbocyclic aromatic system having 5 to 60 carbon atoms including at least one aromatic ring. When the aryl group and the arylene group have at least two rings, they may be fused to each other via a single bond. One or more hydrogen atoms of the aryl group and the arylene group may be substituted with the same substituents as described in connection with the substituted $C_1$-$C_{60}$ alkyl group.

Examples of the substituted or unsubstituted $C_6$-$C_{60}$ aryl group are a phenyl group, a $C_1$-$C_{10}$ alkylphenyl group (for example, ethylphenyl group), a $C_1$-$C_{10}$ alkylbiphenyl group (for example, ethylbiphenyl group), a halophenyl group (for example, o-, m- and p-fluorophenyl groups, a dichlorophenyl group), a dicyanophenyl group, a trifluoromethoxyphenyl group, o-, m-, and p-tolyl groups, o-, m- and p-cumenyl groups, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, a fluoronaphthyl group), a $C_1$-$C_{10}$ alkylnaphthyl group (for example, methylnaphthyl group), a $C_1$-$C_{10}$ alkoxynaphthyl group (for example, a methoxynaphthyl group), an anthracenyl group, an azrenyl group, an acenaphthylenyl group, a phenalenyl group, a fluorenyl group, an anthraquinolinyl group, a methylan anthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentasenyl group, a tetraphenylenyl group, a hexaphenyl group, a hexacenyl group, a rubicenyl group, a coroneryl group, a trinaphthylenyl group, a heptaphenyl group, a heptacenyl group, a piranthrenyl group, and an obarenyl group, and examples of the substituted $C_6$-$C_{60}$ aryl group may be easily understood by referring to the examples of the unsubstituted $C_6$-$C_{60}$ aryl group, and the substituents of the substituted $C_1$-$C_{60}$ alkyl group. Examples of the substituted or unsubstituted $C_6$-$C_{60}$ arylene group may be easily understood by referring to examples of the substituted or unsubstituted $C_6$-$C_{60}$ aryl group.

The unsubstituted $C_2$-$C_{60}$ heteroaryl group used herein refers to a monovalent group having a system composed of one or more aromatic rings having at least one hetero atom selected from nitrogen (N), oxygen (O), phosphorous (P), and sulfur (S) and carbon atoms as the remaining ring atoms. The unsubstituted $C_2$-$C_{60}$ heteroarylene group used herein refers to a divalent group having a system composed of one or more aromatic rings having at least one hetero atom selected from nitrogen (N), oxygen (O), phosphorous (P), and sulfur (S) and carbon atoms as the remaining ring atoms. When the heteroaryl group and the heteroarylene group have at least two rings, they may be fused to each other via a single bond. One or more hydrogen atoms of the heteroaryl group and the heteroarylene group may be substituted with the same substituents as described in connection with the substituted $C_1$-$C_{60}$ alkyl group.

Examples of the unsubstituted $C_2$-$C_{60}$ heteroaryl group are a pyrazolyl group, an imidazolyl group, a oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, benzoan imidazolyl group, an imidazo pyridinyl group, and an imidazo pyrimidinyl group. Examples of the unsubstituted $C_2$-$C_{60}$ heteroarylene group may be easily understood by referring to examples of the substituted or unsubstituted $C_2$-$C_{60}$ arylene group.

The substituted or unsubstituted $C_6$-$C_{60}$ aryloxy group may be represented by —$OA_2$ (wherein $A_2$ indicates the substituted or unsubstituted $C_6$-$C_{60}$ aryl group), and the substituted or unsubstituted $C_6$-$C_{60}$ arylthio group may be represented by —$SA_3$ (wherein $A_3$ indicates a substituted or unsubstituted $C_6$-$C_{60}$ aryl group).

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example

Synthesis of Sub 2(1) to 2(6) Used to Synthesize Sub 2

Sub 2(1) to 2(6), which are compounds used to synthesize Sub 2, were synthesized according to Reaction Scheme 1:

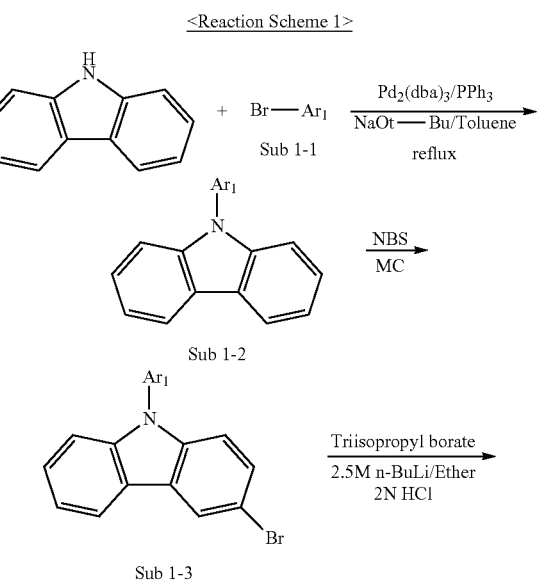

<Reaction Scheme 1>

-continued
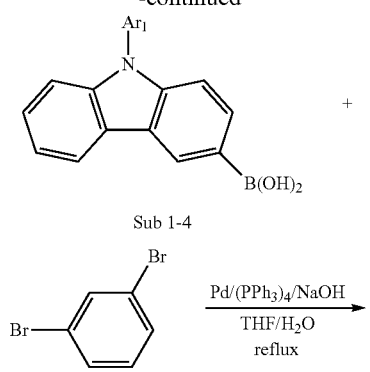
Sub 1-4
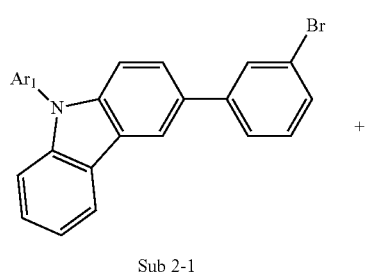
Sub 2-1
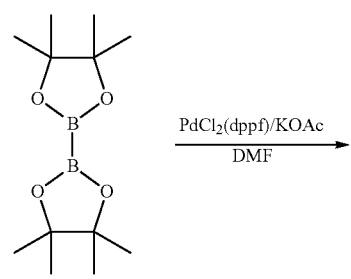
Sub 2-2
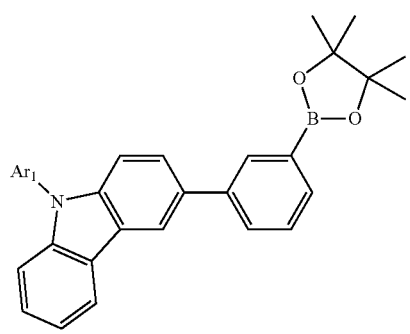
Sub 2-3
-continued
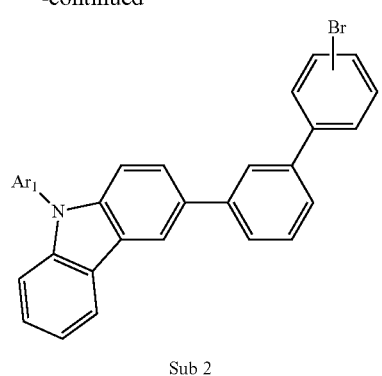
Sub 2
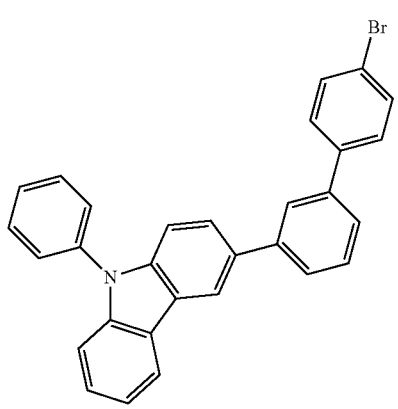
Sub 2(1)
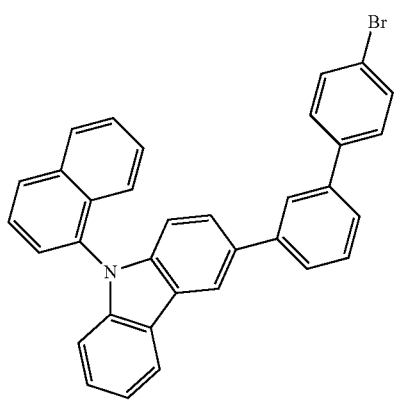
Sub 2(2)
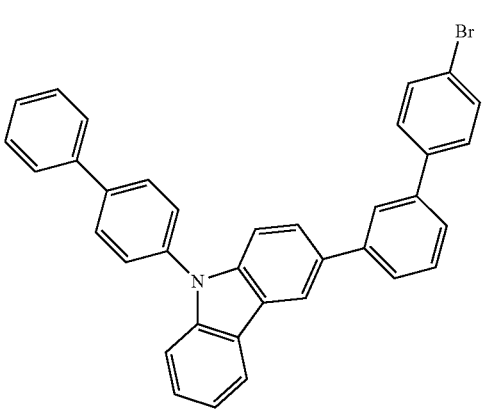
Sub 2(3)

-continued

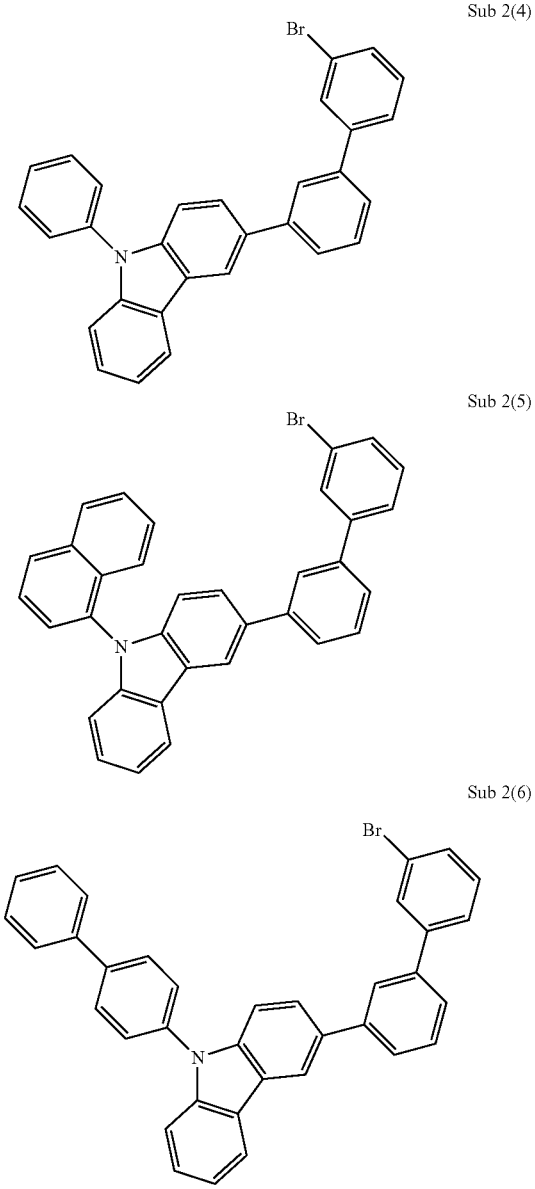

Ar₁ and Sub 2-3 in Reaction Scheme 1 used in synthesizing Sub 2(1) to Sub 2(6) are shown in Table 1:

TABLE 1

| Compound | Reaction Scheme 1 | |
|---|---|---|
| | Ar₁ | Sub 2-3 |
| Sub 2(1) | phenyl | 1-bromo-4-iodobenzene |
| Sub 2(2) | 1-naphthyl | 1-bromo-4-iodobenzene |
| Sub 2(3) | biphenyl | 1-bromo-4-iodobenzene |
| Sub 2(4) | phenyl | 1-bromo-4-iodobenzene |
| Sub 2(5) | 1-naphthyl | 1-bromo-4-iodobenzene |
| Sub 2(6) | biphenyl | 1-bromo-4-iodobenzene |

Synthesis of Sub 1-2

Carbazole (1 eq.) and Sub 1-1 (1.1 eq.) were added to toluene, and then, Pd$_2$(dba)$_3$ (0.05 eq.), PPh$_3$ (0.1 eq.), and NaOt-Bu (3 eq.) were added thereto, and then, the mixture was refluxed at a temperature of 100° C. for 24 hours while stirring, and then, extracted with ether and water. An organic layer was dried by using MgSO$_4$, and the obtained organic material was re-crystallized by silicagel column chromatography to produce Sub 1-2.

Synthesis of Sub 1-3

Sub 1-2 (1 eq.) was dissolved in methylenechloride, and then, N-bromosuccimide (NBS) (1.1 eq.) was slowly added thereto, and then, the mixture was stirred at room temperature for 24 hours. When the reaction stopped, 5% concentration of HCl was added thereto, and then water was added thereto to remove the residual NBS. Thereafter, the resultant solution was extracted with ether and water, and an organic layer was dried and concentrated by using MgSO$_4$, and the obtained organic material was purified by silicagel column chromatography and re-crystallized to obtain Sub 1-3.

Synthesis of Sub 1-4

Sub 1-3 (1 eq.) was dissolved in an anhydrous ether, and the temperature of the reaction product was lowered to −78° C., and n-BuLi (2.5 M in hexane) (1.1 eq.) was slowly dropped thereto, and the reaction product was stirred for 30 minutes. Thereafter, the temperature of the reaction product was lowered to −78° C., and triisopropylborate (1.5 eq.) was dropped thereto. The resultant mixture was stirred at room temperature and then, diluted by adding water thereto and 2 N HCl was added thereto. When the reaction stopped, an extraction process was performed thereon by using ethyl acetate and water, and then, an organic layer was dried and concentrated by using MgSO4, and then, the obtained organic material was purified by silicagel column chromatography and re-crystallized to obtain Sub1-4.

Synthesis of Sub 2-1

Sub 1-4 (1 eq.) was dissolved in THF, and then, 1,3-dibromobenzene (1.1 eq.), Pd(PPh$_3$)$_4$ (0.03 eq.), NaOH (3 eq.), and water were added thereto, and the mixture was refluxed while stirring. When the reaction stopped, an extraction process was performed thereon by using ether and water, and then, an organic layer was dried and concentrated by using MgSO4, and then, the obtained organic material was purified by silicagel column chromatography and re-crystallized to obtain Sub 2-1.

Synthesis of Sub 2-2

Sub 2-1 (1 eq.) was dissolved in DMF, and then, bispinacolatodiboron (1.1 eq.), PdCl$_2$(dppf) (0.03 eq.), and KOAc (3 eq.) were sequentially added thereto, and then, the mixture was stirred for 24 hours to synthesize a borate compound, and then, the obtained compound was purified by silicagel column chromatography and re-crystallized to obtain Sub 2-2.

Synthesis of Sub 2

Sub 2-2 (1.1 eq.) was dissolved in THF, and then, Sub 2-3 (1.1 eq.), Pd(PPh$_3$)$_4$ (0.03 eq.), NaOH (3 eq.), and water were added thereto, and the mixture was refluxed while stirring. When the reaction stopped, an extraction process was performed thereon by using ether and water, and then, an organic layer was dried and concentrated by using MgSO$_4$, and then, the obtained organic material was purified by silicagel column chromatography and re-crystallized to obtain Sub 2.

MS data of Sub 2(1) to 2(6), which were used to synthesize Sub 2, are shown in Table 2 below:

TABLE 2

| Compound | FD-MS | Compound | FD-MS |
| --- | --- | --- | --- |
| Sub 2(1) | m/z = 473.08($C_{30}H_{20}BrN$ = 474.39) | Sub 2(2) | m/z = 523.09($C_{34}H_{22}BrN$ = 524.45) |
| <Formula 23> | m/z = 549.11($C_{36}H_{24}BrN$ = 550.49) | <Formula 24> | m/z = 473.08($C_{30}H_{20}BrN$ = 474.39) |
| Sub 2(5) | m/z = 523.09($C_{34}H_{22}BrN$ = 524.45) | Sub 2(6) | m/z = 549.11($C_{36}H_{24}BrN$ = 550.49) |

Synthesis of Sub 3(1) to 3(24) Belonging to Sub 3

Sub 3(1) to 3(24), which are compounds used to synthesize Sub 3, were synthesized according to Reaction Scheme 2:

<Reaction Scheme 2>

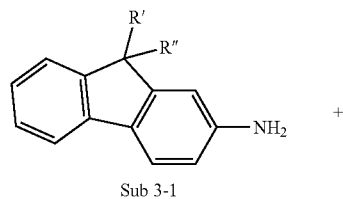

Sub 3-1

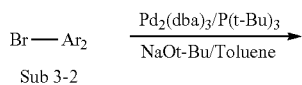

Sub 3-2

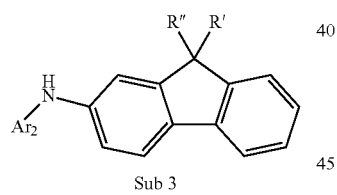

Sub 3

Sub 3(1)

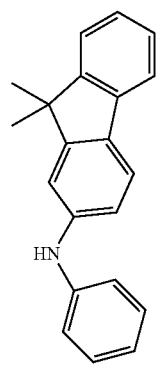

-continued

Sub 3(2)

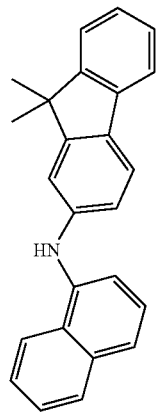

Sub 3(3)

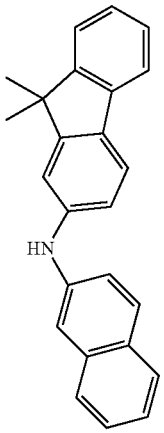

Sub 3(4)

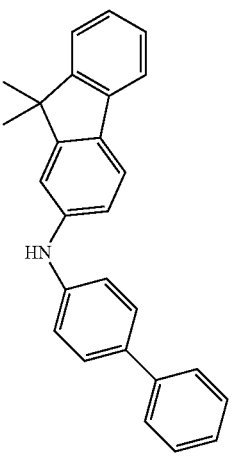

Sub 3(5)
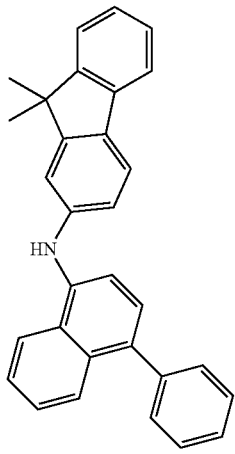
Sub 3(6)
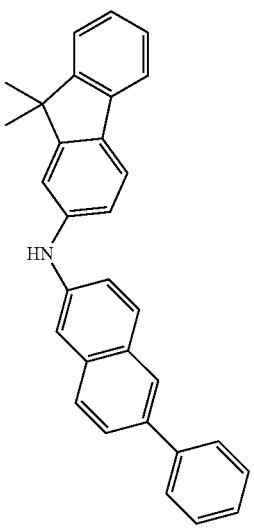
Sub 3(7)
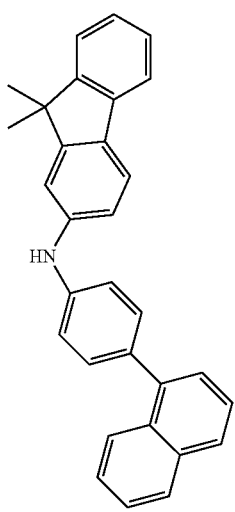
Sub 3(8)
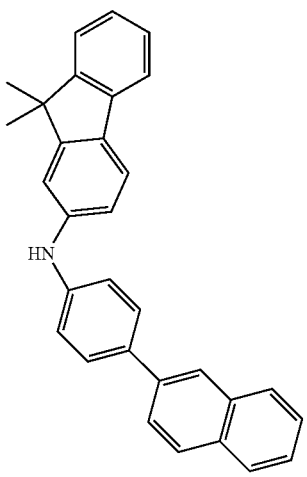
Sub 3(9)
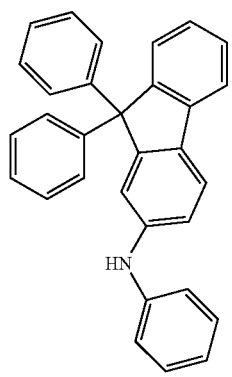
Sub 3(10)
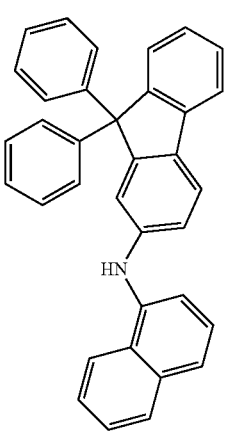

Sub 3(11)
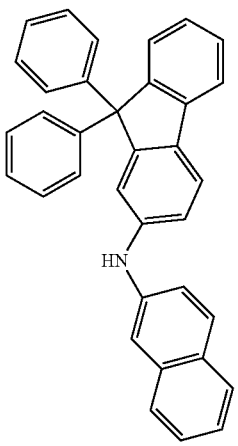
Sub 3(14)
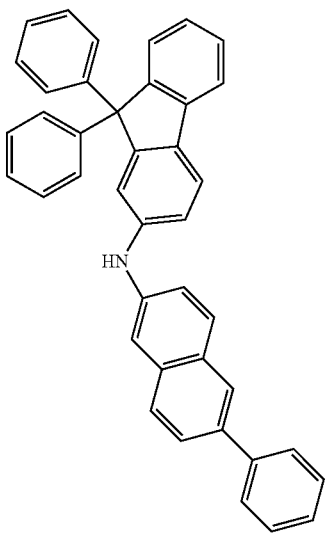
Sub 3(12)
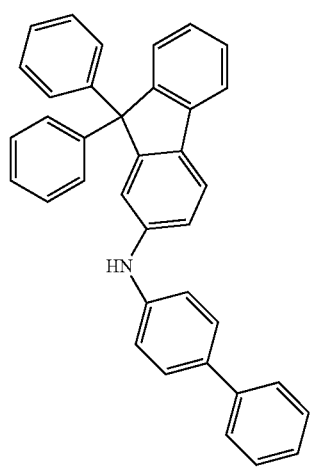
Sub 3(15)
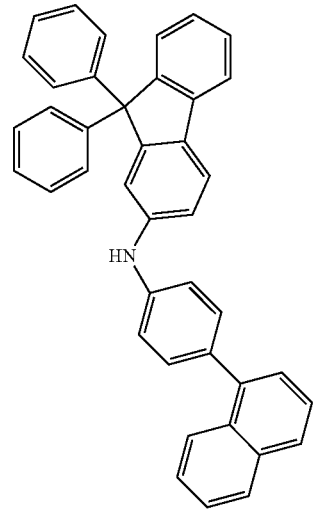
Sub 3(13)
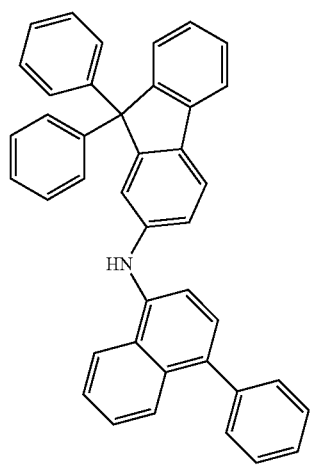
Sub 3(16)
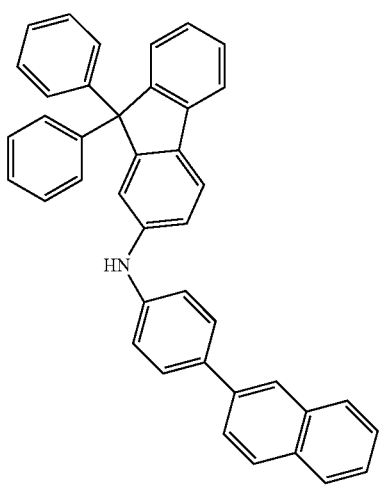

Sub 3(17)
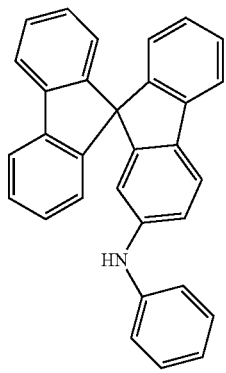
Sub 3(20)
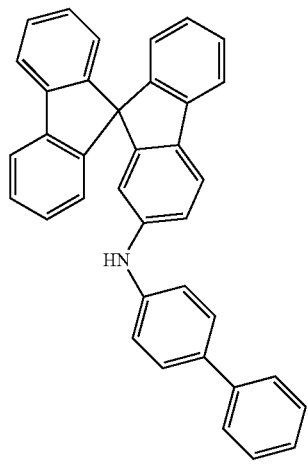
Sub 3(18)
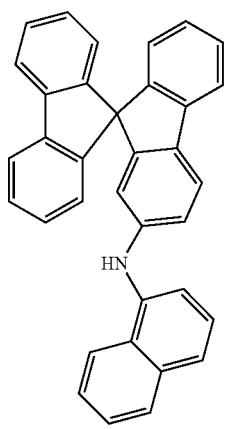
Sub 3(21)
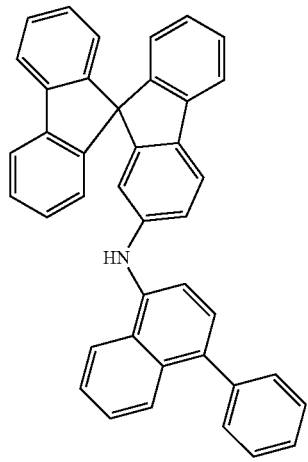
Sub 3(19)
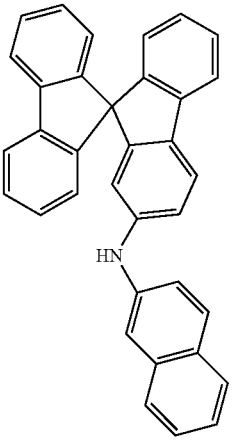
Sub 3(22)
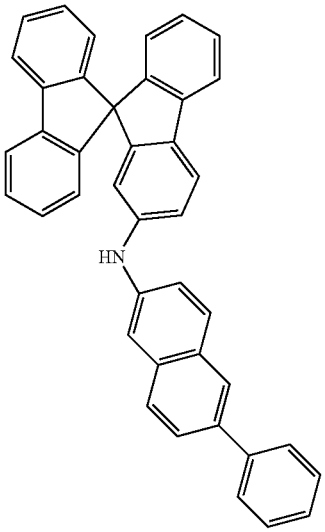

-continued
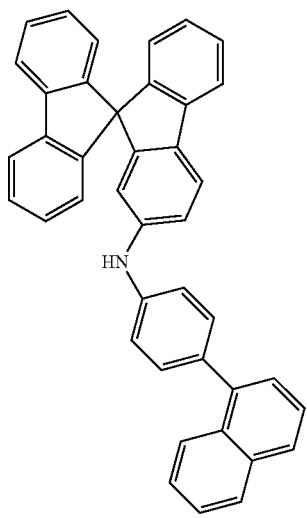
Sub 3(23)
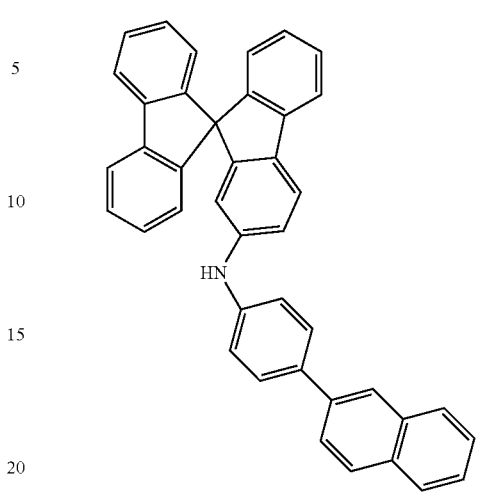
Sub 3(24)
Ar₂ and Sub 3-1 in Reaction Scheme 2 synthesized by using Sub 3(1) to Sub 3(24) are shown in Table 3:
TABLE 3
| | Reaction Scheme 2 | |
|---|---|---|
| Compound | Ar₂ | Sub 3-1 |
| Sub 3(1) | phenyl | 9,9-dimethyl-9H-fluorene-2-amine |
| Sub 3(2) | 1-naphthyl | |
| Sub 3(3) | 2-naphthyl | |
| Sub 3(4) | *-biphenyl | |
| Sub 3(5) | *-(4-phenyl-1-naphthyl) | |
| Sub 3(6) | *-(6-phenyl-2-naphthyl) | |
| Sub 3(7) | *-(4-(1-naphthyl)phenyl) | |
| Sub 3(8) | *-(4-(2-naphthyl)phenyl) | |
| Sub 3(9) | phenyl | 9,9-diphenyl-9H-fuorene-2-amine |
| Sub 3(10) | 1-naphthyl | |
| Sub 3(11) | 2-naphthyl | |

TABLE 3-continued
| Reaction Scheme 2 | | |
|---|---|---|
| Compound | Ar₂ | Sub 3-1 |
| Sub 3(12) | 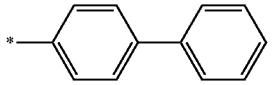 | |
| Sub 3(13) | 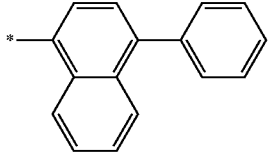 [SMILES: *c1ccc(-c2ccccc2)c2ccccc12] | |
| Sub 3(14) | 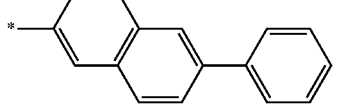 | |
| Sub 3(15) | 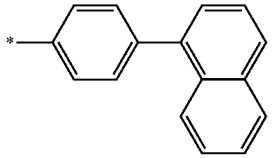 [SMILES: *c1ccc(-c2cccc3ccccc23)cc1] | |
| Sub 3(16) | 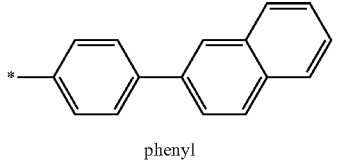 | |
| Sub 3(17) | phenyl | 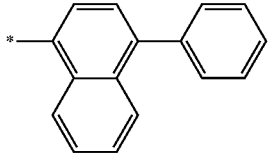 [SMILES: *c1ccc(-c2ccccc2)c2ccccc12] |
| Sub 3(18) | 1-naphthyl | |
| Sub 3(19) | 2-naphthyl | |
| Sub 3(20) | 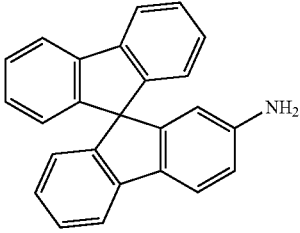 | |
| Sub 3(21) | 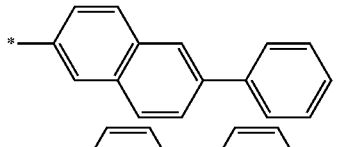 | |
| Sub 3(22) | 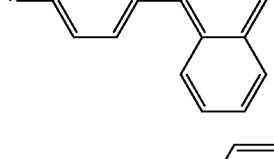 | |
| Sub 3(23) | 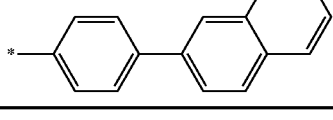 | |
| Sub 3(24) | | |

Sub 3-1 (1 eq.), Sub 3-2 (1.1 eq.), Pd2(dba)$_3$ (0.05 eq.), P(t-Bu)$_3$ (0.1 eq.), NaOt-Bu (3 eq.), and toluene (10.5 mL/1 mmol starting material) were added to a round-bottomed flask and then, the reaction was performed thereon at a temperature of 100° C. When the reaction stopped, an extraction process was performed thereon by using ether and water, and then, an organic layer was dried and concentrated by using MgSO$_4$, and then, the obtained organic material was purified by silicagel column chromatography and re-crystallized to obtain Sub 3.

MS data of Sub 3(1) to 3(24), which were used to synthesize Sub 2, are shown in Table 4 below:

TABLE 4

| Compound | FD-MS | Compound | FD-MS |
| --- | --- | --- | --- |
| Sub 3(1) | m/z = 285.15($C_{21}H_{19}N$ = 285.38) | Sub 3(2) | m/z = 335.17($C_{25}H_{21}N$ = 335.44) |
| Sub 3(3) | m/z = 335.17($C_{25}H_{21}N$ = 335.44) | Sub 3(4) | m/z = 361.18($C_{27}H_{28}N$ = 361.48) |
| Sub 3(5) | m/z = 411.20($C_{31}H_{25}N$ = 411.54) | Sub 3(6) | m/z = 411.20($C_{31}H_{25}N$ = 411.54) |
| Sub 3(7) | m/z = 411.20($C_{31}H_{25}N$ = 411.54) | Sub 3(8) | m/z = 411.20($C_{31}H_{25}N$ = 411.54) |
| Sub 3(9) | m/z = 409.18($C_{31}H_{23}N$ = 409.52) | Sub 3(10) | m/z = 459.20($C_{35}H_{25}N$ = 459.58) |
| Sub 3(11) | m/z = 459.20($C_{35}H_{25}N$ = 459.58) | Sub 3(12) | m/z = 485.21($C_{37}H_{27}N$ = 485.62) |
| Sub 3(13) | m/z = 535.23($C_{41}H_{29}N$ = 535.68) | Sub 3(14) | m/z = 535.23($C_{41}H_{29}N$ = 535.68) |
| Sub 3(15) | m/z = 535.23($C_{41}H_{29}N$ = 535.68) | Sub 3(16) | m/z = 535.23($C_{41}H_{29}N$ = 535.68) |
| Sub 3(17) | m/z = 407.17($C_{31}H_{21}N$ = 407.51) | Sub 3(18) | m/z = 457.18($C_{35}H_{23}N$ = 457.56) |
| Sub 3(19) | m/z = 457.18($C_{35}H_{23}N$ = 457.56) | Sub 3(20) | m/z = 483.20($C_{37}H_{25}N$ = 483.60) |
| Sub 3(21) | m/z = 533.21($C_{41}H_{27}N$ = 533.66) | Sub 3(22) | m/z = 533.21($C_{41}H_{27}N$ = 533.66) |
| Sub 3(23) | m/z = 533.21($C_{41}H_{27}N$ = 533.66) | Sub 3(24) | m/z = 533.21($C_{41}H_{27}N$ = 533.66) |

Synthesis Example 1

Synthesis of Compound 2

Sub 312 (1 eq.), Sub 21 (1.1 eq.), Pd2(dba)$_3$ (0 eq.), P(t-Bu)$_3$ (0.1 eq.), NaOt-Bu (3 eq.), and toluene (10.5 mL/1 mmol starting material) were added to a round-bottomed flask and then, the reaction was performed thereon at a temperature of 100° C. When the reaction stopped, an extraction process was performed thereon by using ether and water, and then, an organic layer was dried and concentrated by using MgSO4, and then, the obtained organic material was purified by silicagel column chromatography and re-crystallized to obtain Compound 2. The synthesized compound was identified by MS/FAB an $^1$H NMR.

m/z=878.37 ($C_{67}H_{46}N_2$=879.10)

$^1$H NMR (CDCl$_3$, 400 MHz) δ(ppm) 7.13-7.23 (m, 15H), 7.30-7.75 (m, 28H), 7.92 (s, 1H), 8.22 (d, J=7.7 Hz, 1H), 8.43 (d, J=1.3 Hz, 1H)

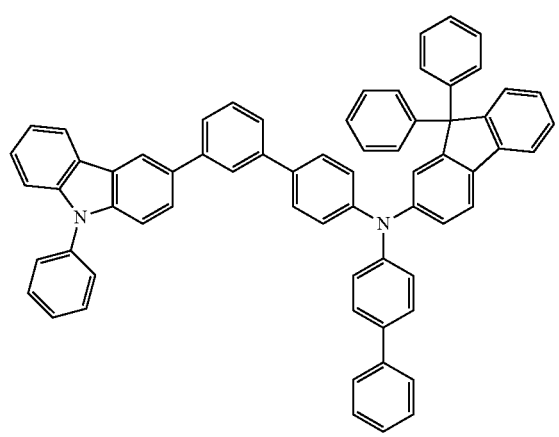

2

Synthesis Example 2

Synthesis of Compound 8

Compound 8 was synthesized in the same manner as in Synthesis Example 1, except that Sub2 (3) was used instead of Sub 2(1). The synthesized compound was identified by MS/FAB an $^1$H NMR.

m/z=954.40 ($C_{73}H_{50}N_2$=955.19)

$^1$H NMR (CDCl$_3$, 400 MHz) δ(ppm) 7.12-7.79 (m, 45H), 7.86 (d, J=8.5 Hz, 2H), 7.94 (s, 1H), 8.24 (d, J=7.6 Hz, 1H), 8.45 (d, J=1.4 Hz, 1H)

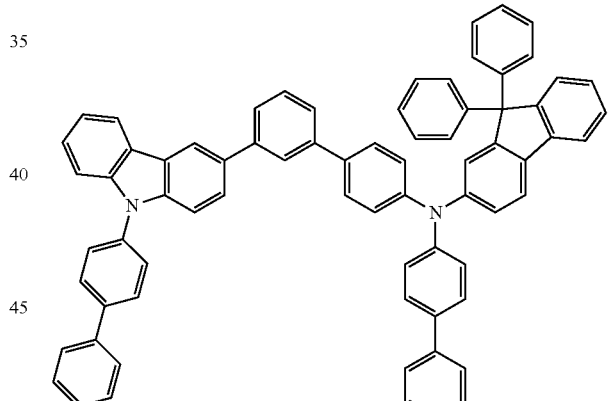

8

Synthesis Example 3

Synthesis of Compound 7

Compound 7 was synthesized in the same manner as in Synthesis Example 1, except that Sub 3(9) and Sub 2(3) were respectively used instead of Sub 3(12) and Sub 2(1). The synthesized compound was identified by MS/FAB an $^1$H NMR.

m/z=878.37 ($C_{67}H_{46}N_2$=879.10)

$^1$H NMR (CDCl$_3$, 400 MHz) δ(ppm) 6.99-7.79 (m, 41H), 7.86 (d, J=8.5 Hz, 2H), 7.93 (s, 1H), 8.24 (d, J=7.6 Hz, 1H), 8.44 (d, J=1.3 Hz, 1H)

7

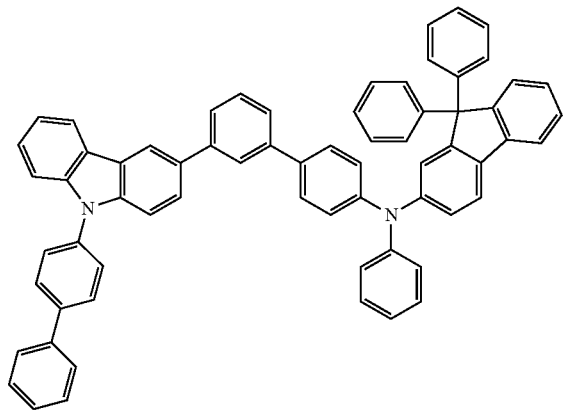

Synthesis Example 4

Synthesis of Compound 26

Compound 26 was synthesized in the same manner as in Synthesis Example 1, except that Sub 3(4) and Sub 2(3) were respectively used instead of Sub 3(12) and Sub 2(1). The synthesized compound was identified by MS/FAB an $^1$H NMR.

m/z=754.33 ($C_{57}H_{42}N_2$=754.96)

$^1$H NMR (CDCl$_3$, 400 MHz) δ(ppm) 1.45 (s, 6H), 7.15 (brs, 2H), 7.27-7.34 (m, 8H), 7.39-7.74 (m, 23H), 7.94 (s, 1H), 8.21 (d, J=7.7 Hz, 1H), 8.42 (d, J=1.6 Hz, 1H)

26

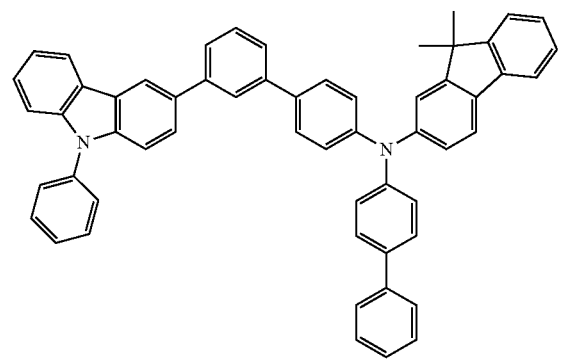

Synthesis Example 5

Synthesis of Compound 55

Compound 55 was synthesized in the same manner as in Synthesis Example 1, except that Sub 3(9) and Sub 2(6) were respectively used instead of Sub 3(12) and Sub 2(1). The synthesized compound was identified by MS/FAB an $^1$H NMR.

m/z=878.37 ($C_{67}H_{46}N_2$=879.10)

$^1$H NMR (CDCl$_3$, 400 MHz) δ(ppm) 6.97-7.75 (m, 41H), 7.80-7.87 (m, 3H), 8.18 (d, J=7.6 Hz, 1H), 8.36 (d, J=1.2 Hz, 1H)

55

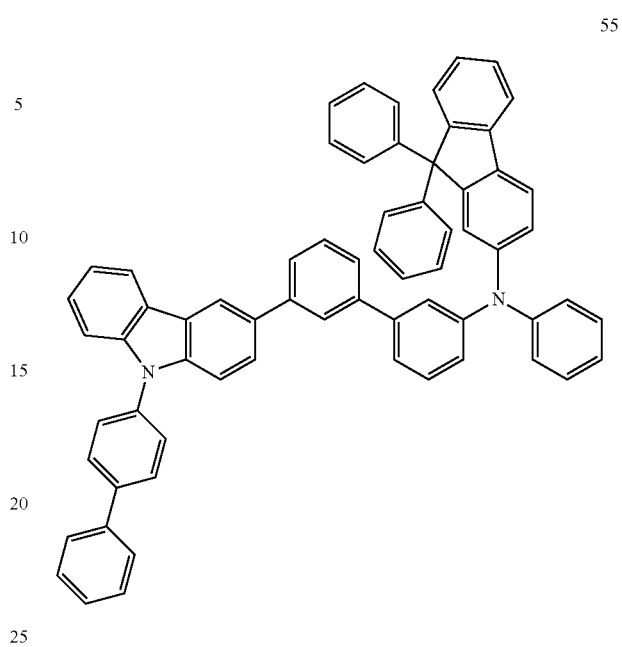

Synthesis Example 6

Synthesis of Compound 50

Compound 50 was synthesized in the same manner as in Synthesis Example 1, except that Sub2 (4) was used instead of Sub 2(1). The synthesized compound was identified by MS/FAB an $^1$H NMR.

m/z=878.37 ($C_{67}H_{46}N_2$=879.10)

$^1$H NMR (CDCl$_3$, 400 MHz) δ(ppm) 7.06-7.76 (m, 43H), 7.84 (s, 1H), 8.18 (d, J=7.7 Hz, 1H), 8.38 (d, J=1.6 Hz, 1H)

50

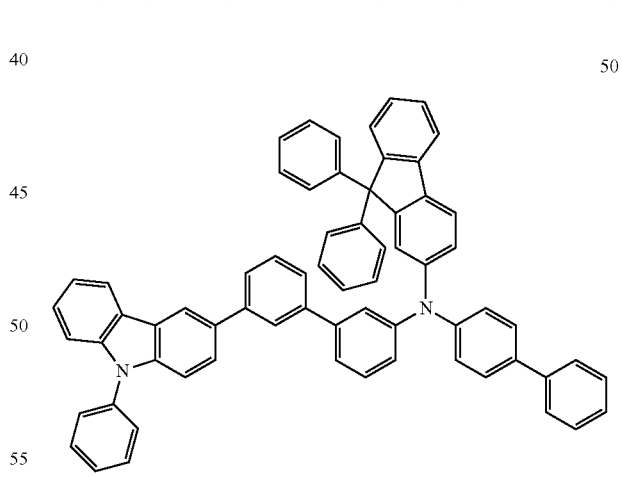

Synthesis Example 7

Synthesis of Compound 14

Compound 14 was synthesized in the same manner as in Synthesis Example 1, except that Sub 2 (4) was used instead of Sub 2(1). The synthesized compound was identified by MS/FAB an $^1$H NMR.

m/z=928.38 ($C_{71}H_{48}N_2$=929.15)

¹H NMR (CDCl₃, 400 MHz) δ(ppm) 7.01-7.24 (m, 16H), 7.27-7.79 (m, 27H), 7.92 (s, 1H), 8.02-8.10 (m, 2H), 8.25-8.29 (m, 1H), 8.48 (d, J=1.2 Hz, 1H)

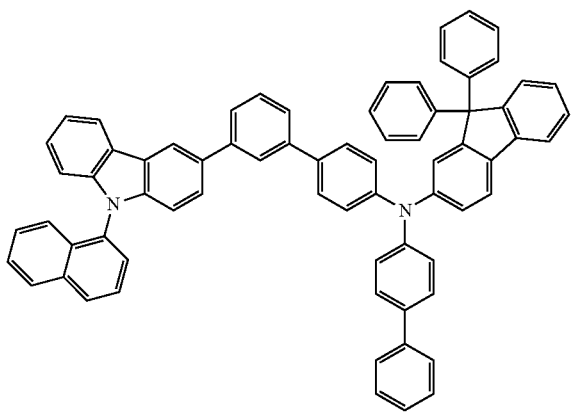

Synthesis Example 8

Synthesis of Compound 5

Compound 5 was synthesized in the same manner as in Synthesis Example 1, except that Sub 3 (10) was used instead of Sub 3(12). The synthesized compound was identified by MS/FAB an ¹H NMR.

m/z=852.35 (C₆₅H₄₄N₂=853.06)

¹H NMR (CDCl₃, 400 MHz) δ(ppm) 6.98 (dd, J=8.3, 2.1 Hz, 1H), 7.04 (d, J=8.6 Hz, 2H), 7.09-7.22 (m, 11H), 7.27-7.38 (m, 6H), 7.42-7.66 (m, 17H), 7.70 (dd, J=8.5, 1.7 Hz, 1H), 7.78 (d, J=8.3 Hz, 1H), 7.87-7.91 (m, 3H), 8.19 (d, J=7.7 Hz, 1H), 8.39 (d, J=1.6 Hz, 1H)

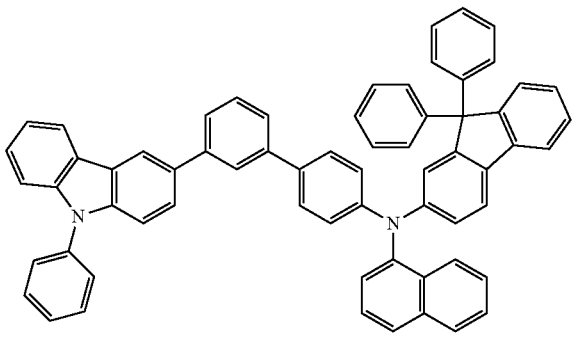

Example 1

An anode was manufactured as follows: an ITO glass substrate (a product of Corning Co., Ltd) having an ITO layer having a thickness of 15 Ω/cm² (1200 Å) was cut to a size of 50 mm×50 mm×0.7 mm, and then, sonicated by using isopropyl alcohol and pure water each for 5 minutes, and cleaned by the exposure to ultraviolet rays for 30 minutes, and then ozone. The anode, that is, the ITO glass substrate, was mounted on a vacuum deposition apparatus.

Compound 26 and Compound 501 were vacuum co-deposited on the ITO glass at a weight ratio of 99:1 to form a first hole transport layer having a thickness of 100 Å, and then, Compound 26 was vacuum deposited on the first hole transport layer to form a second hole transport layer having a thickness of 600 Å, Compound 26 and Compound 501 were vacuum co-deposited on the second hole transport layer at a weight ratio of 99:1 to form a third hole transport layer having a thickness of 100 Å, and Compound 26 was vacuum deposited on the third hole transport layer to form a fourth hole transport layer having a thickness of 600 Å.

Compound 26 was vacuum deposited on the fourth hole transport layer to form a buffer layer having a thickness of 100 Å.

ADN(host) and DPAVBi(dopant) were co-deposited on the buffer layer at a weight ratio of 98:2 to form an emission layer having a thickness of 200 Å.

Subsequently, Compound 101 was vacuum deposited on the fourth hole transport layer to form an electron transport layer having a thickness of 360 Å.

LiQ was vacuum deposited on the electron transport layer, to form an electron injection layer having a thickness of 10 Å, and then, Mg and Agwere vacuum deposited to form a cathode having a thickness of 110 Å, thereby completing manufacturing an organic light-emitting device.

<Compound 101>

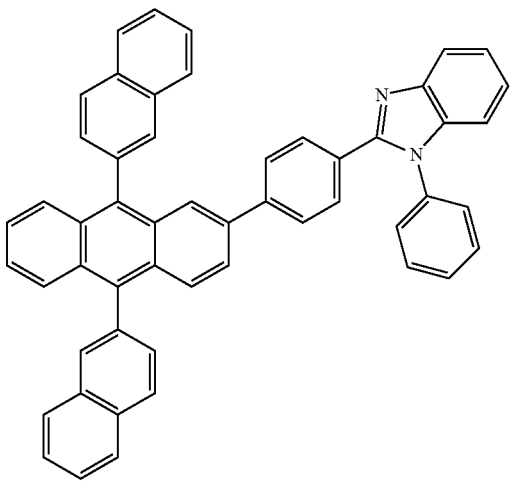

Example 2

An organic light-emitting device was manufactured in the same manner as in Example 1, except that in forming the first hole transport layer and the third hole transport layer, Compound 26 and Compound 501 were used at a weight ratio of 98:2.

Example 3

An organic light-emitting device was manufactured in the same manner as in Example 1, except that in forming the third hole transport layer, a thickness of the third hole transport layer was 200 Å.

Example 4

An organic light-emitting device was manufactured in the same manner as in Example 1, except that in forming the first hole transport layer, Compound 26 and Compound 501 were used at a weight ratio of 98:2, and in forming the third hole transport layer, a thickness of the third hole transport layer was 200 Å.

Comparative Example 1

An organic light-emitting device was manufactured in the same manner as in Example 1, except that in forming the first hole transport layer, the second hole transport layer, the third hole transport layer, and the fourth hole transport layer, Compound A was used instead of Compound 26, and the buffer layer was not formed.

<Compound A>

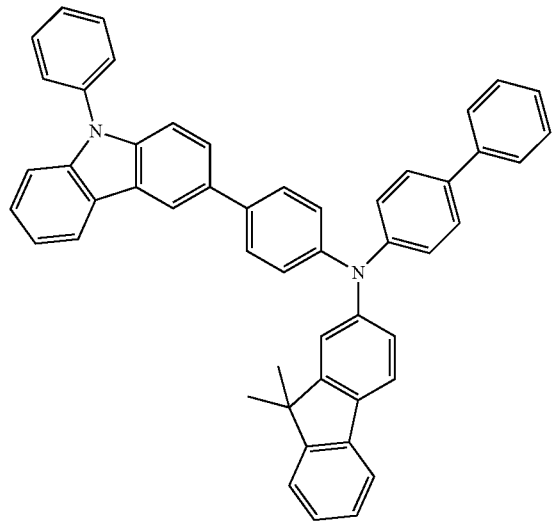

Comparative Example 2

An organic light-emitting device was manufactured in the same manner as in Example 1, except that in forming the first hole transport layer, the second hole transport layer, the third hole transport layer, and the fourth hole transport layer, Compound A was used instead of Compound 26.

Evaluation Example

Driving voltage, current density, efficiency, brightness, color coordinate, efficiency/y, and lifespan of the organic light-emitting devices manufactured according to Examples 1 to 4 and Comparative Examples 1 and 2 were evaluated. Evaluation results are shown in Table 5 below.

TABLE 5

| | Driving voltage (V) | Current density (mA/cm$^2$) | Efficiency (cd/A) | Brightness (lm/W) | CIE color coordinate (x, y) | Efficiency/y |
|---|---|---|---|---|---|---|
| Example 1 | 3.9 | 10.8 | 5.3 | 4.3 | (0.145, 0.044) | 121.1 |
| Example 2 | 4.0 | 9.5 | 6.4 | 5.0 | (0.144, 0.046) | 138.4 |
| Example 3 | 4.2 | 9.0 | 6.9 | 5.1 | (0.143, 0.048) | 144.4 |

TABLE 5-continued

| | Driving voltage (V) | Current density (mA/cm$^2$) | Efficiency (cd/A) | Brightness (lm/W) | CIE color coordinate (x, y) | Efficiency/y |
|---|---|---|---|---|---|---|
| Example 4 | 4.0 | 9.7 | 6.3 | 5.0 | (0.143, 0.047) | 135.2 |
| Comparative Example 1 | 4.0 | 10.3 | 4.5 | 2.2 | (0.146, 0.048) | 93.8 |
| Comparative Example 2 | 4.0 | 10.5 | 5.2 | 2.2 | (0.146, 0.048) | 108.3 |

Referring to Table 1, the organic light-emitting devices of Examples 1 to 4 had higher efficiency than the organic light-emitting devices of Comparative Example 1 and 2. Efficiency of the organic light-emitting device of Example 3 was 65% greater than the organic light-emitting device of Comparative Example 1.

By way of summation and review, an organic light-emitting diode may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, are recombined with each other in the emission layer to generate excitons. Then, the excitons are transitioned from an excited state to a ground state, thereby generating light.

According to embodiments, an organic light-emitting device may have an increased efficiency and lifespan without an increase in driving voltage. The organic light-emitting device may include of a plurality of hole transport layers.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic light-emitting device, comprising:
a first electrode;
a second electrode facing the first electrode;
an emission layer disposed between the first electrode and the second electrode;
a first hole transport layer that is disposed between the emission layer and the first electrode and includes a first compound and a first charge-generation material;
a second hole transport layer that is disposed between the emission layer and the first hole transport layer and includes a second compound;
a third hole transport layer that is disposed between the emission layer and the second hole transport layer and includes a third compound and a second charge-generation material; and a fourth hole transport layer that is disposed between the emission layer and the third hole transport layer and includes a fourth compound;

wherein the first compound, the second compound, the third compound, and the fourth compound are each independently a compound represented by Formula 1 or 2:

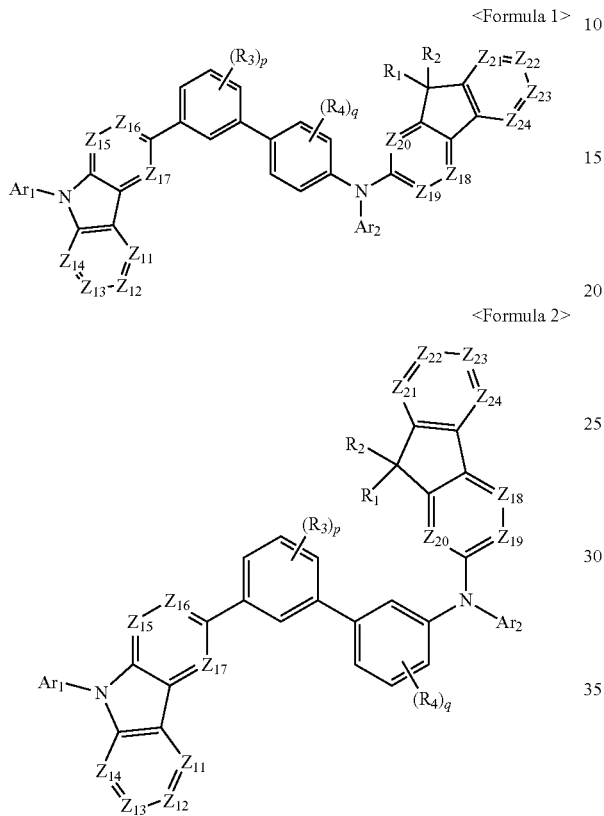

<Formula 1>

<Formula 2> wherein in Formulae 1 and 2, $Z_{11}$ is N or $C(R_{11})$, $Z_{12}$ is N or $C(R_{12})$, $Z_{13}$ is N or $C(R_{13})$, $Z_{14}$ is N or $C(R_{14})$, $Z_{15}$ is N or $C(R_{15})$, $Z_{16}$ is N or $C(R_{16})$, $Z_{17}$ is N or $C(R_{17})$, $Z_{18}$ is N or $C(R_{18})$, $Z_{19}$ is N or $C(R_{19})$, $Z_{20}$ is N or $C(R_{20})$, $Z_{21}$ is N or $C(R_{21})$, $Z_{22}$ is N or $C(R_{22})$, $Z_{23}$ is N or $C(R_{23})$, and $Z_{24}$ is N or $C(R_{24})$;

$Ar_1$ and $Ar_2$ are each independently selected from:

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group; and a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group, each substituted with at least one selected from a deuterium, a halogen atom, a hydroxyl group, a cyano group, a nitro group, an amino group, an amidino group, a hydrazine group, a hydrazone group, a carboxyl group and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_2$-$C_{60}$ aryloxy group, a $C_6$-$C_{60}$ arylthio group, and a $C_2$-$C_{60}$ heteroaryl group; and $R_1$ and $R_2$ are each independently selected from:

a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group; and a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group, each substituted with at least one selected from a deuterium, a halogen atom, a hydroxyl group, a cyano group, a nitro group, an amino group, an amidino group, a hydrazine group, a hydrazone group, a carboxyl group and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_2$-$C_{60}$ aryloxy group, a $C_6$-$C_{60}$ arylthio group, and a $C_2$-$C_{60}$ heteroaryl group; and $R_3$, $R_4$, and $R_{11}$ to $R_{24}$ are each independently selected from:

a hydrogen, a deuterium, a halogen atom, a hydroxyl group, a cyano group, a nitro group, an amino group, an amidino group, a hydrazine group, a hydrazone group, a carboxyl group and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, and a $C_2$-$C_{60}$ heteroaryl group, each substituted with at least one selected from a deuterium, a halogen atom, a hydroxyl group, a cyano group, a nitro group, an amino group, an amidino group, a hydrazine group, a hydrazone group, a carboxyl group and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_2$-$C_{60}$ aryloxy group, a $C_6$-$C_{60}$ arylthio group, and a $C_2$-$C_{60}$ heteroaryl group; and —N($Q_{11}$)($Q_{12}$), —Si($Q_{13}$)($Q_{14}$)($Q_{15}$), and —B($Q_{16}$)($Q_{17}$) (wherein $Q_{11}$ to $Q_{17}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group); and p and q are each independently an integer of 1 to 4.

2. The organic light-emitting device as claimed in claim 1, wherein $Ar_1$ and $Ar_2$ are each independently selected from:
  i) a phenyl group, a pentalenyl group, an indenyl group, a naphtyl group, an azulenyl group, an indacenyl group, an acenaphtyl group, a fluorenyl group, a spiro-fluorenyl group, a phenalenyl group, a phenanthrenyl group, an anthryl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, a dibenzofuranyl group, a dibenzothiophenyl group, and a benzocarbazolyl group; and
  ii) a phenyl group, a naphtyl group, a fluorenyl group, a spiro-fluorenyl group group, a phenanthrenyl group, an anthryl group, a fluoranthenyl group, a triphenylenyl group, a pyrenyl group, a chrysenyl group, a pyridinyl group, a pyrazinyl group, a pyrimidinyl group, a pyridazinyl group, a isoindolyl group, an indolyl group, a quinolinyl group, a benzoquinolinyl group, a quinoxalinyl group, a quinazolinyl group, a cinnolinyl group, a carbazolyl group, and a triazinyl group, each substituted with at least one selected from a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphtyl group, a fluorenyl group, a spiro-fluorenyl group group, a phenanthrenyl group, an anthryl group, a fluoranthenyl group, a triphenylenyl group, a pyrenyl group, a chrysenyl group, a pyridinyl group, a pyrazinyl group, a pyrimidinyl group, a pyridazinyl group, a isoindolyl group, an indolyl group, a quinolinyl group, a benzoquinolinyl group, a quinoxalinyl group, a quinazolinyl group, a cinnolinyl group, a carbazolyl group, and a triazinyl group.

3. The organic light-emitting device as claimed in claim 1, wherein:
  $Ar_1$ and $Ar_2$ are each independently represented by one of Formulae 3-1 to 3-20:

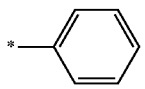

3-1

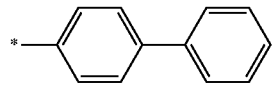

3-2

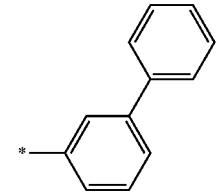

3-3

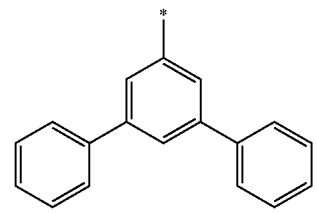

3-4

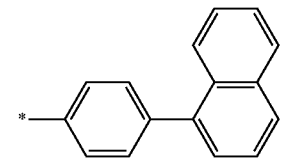

3-5

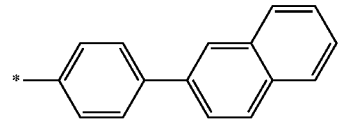

3-6

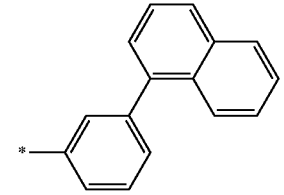

3-7

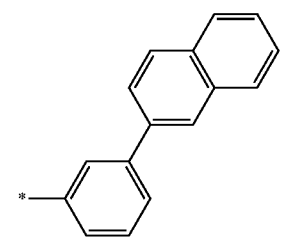

3-8

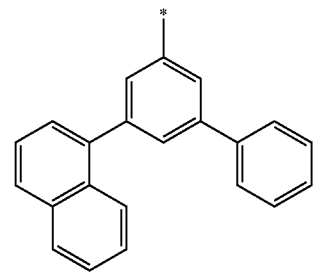

3-9

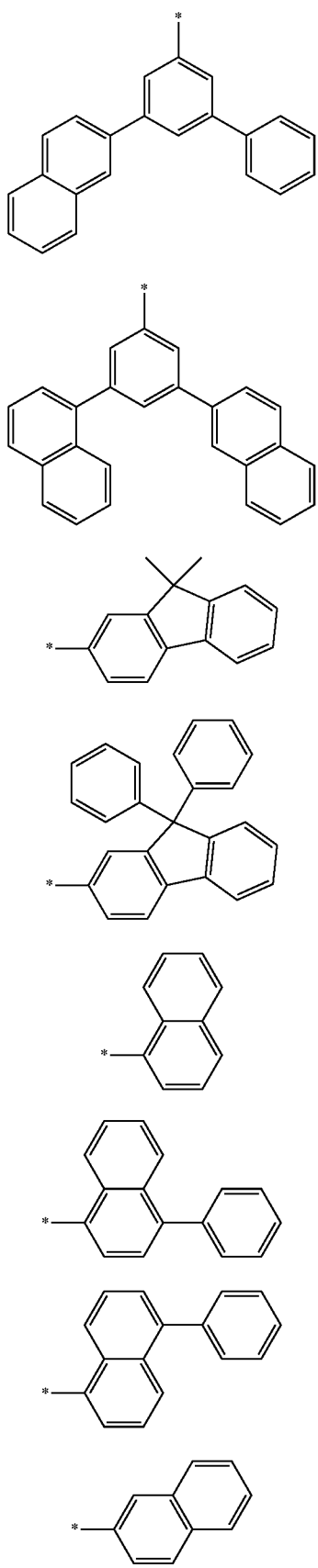
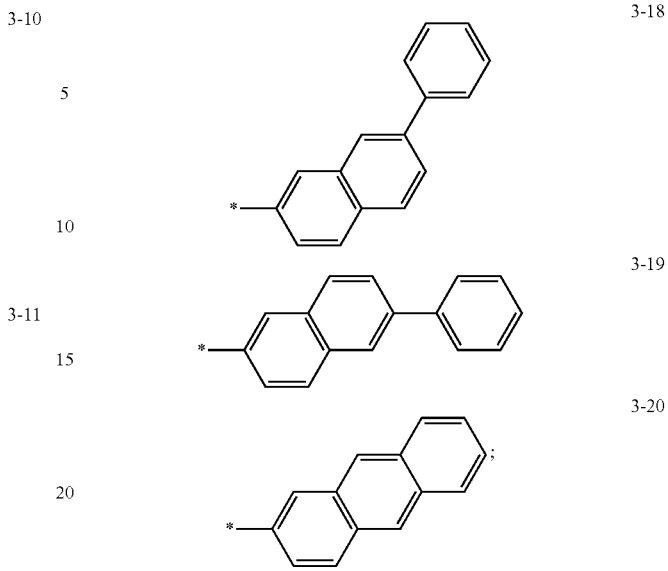
and
* in Formulae 3-1 to 3-20 indicates a binding site to a nitrogen atom (N) of Formula 1 or 2.
4. The organic light-emitting device as claimed in claim 1, wherein the first compound, the second compound, the third compound, and the fourth compound are each independently a compound represented by Formula 1A or 2A:
<Formula 1A>
<Formula 2A>
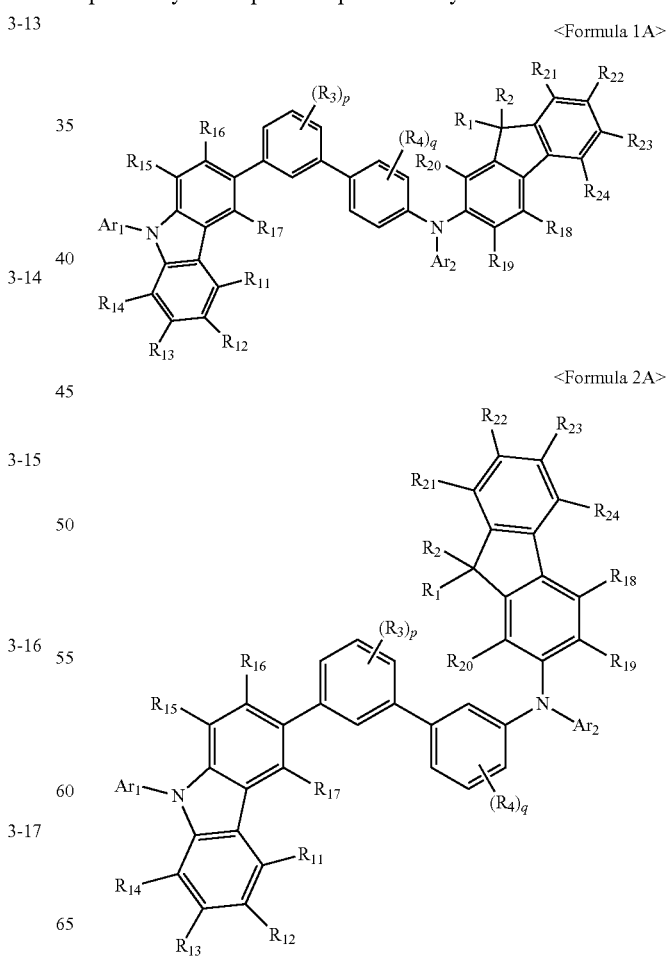

wherein in Formulae 1A and 2A,
Ar$_1$, Ar$_2$, R$_1$ to R$_4$, R$_{11}$ to R$_{24}$, p and q are each independently the same as groups defined for Formula 1 or Formula 2.
5. The organic light-emitting device as claimed in claim 1, wherein the first compound, the second compound, the third compound, and the fourth compound are each independently selected from Compounds 1 to 96:
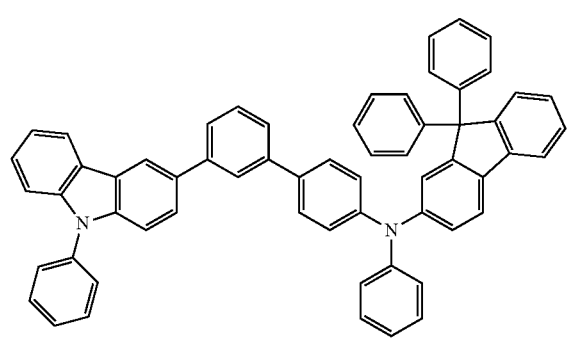
1
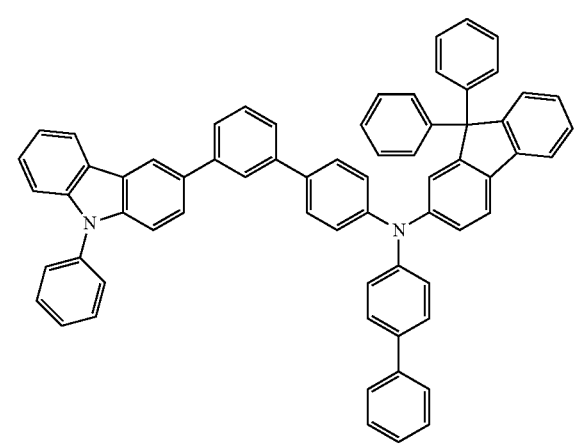
2
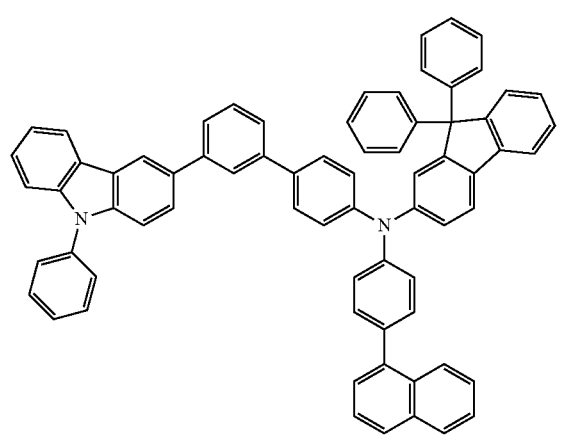
3
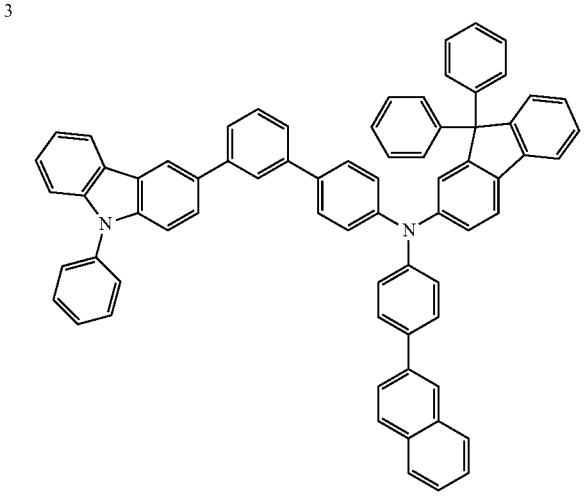
4
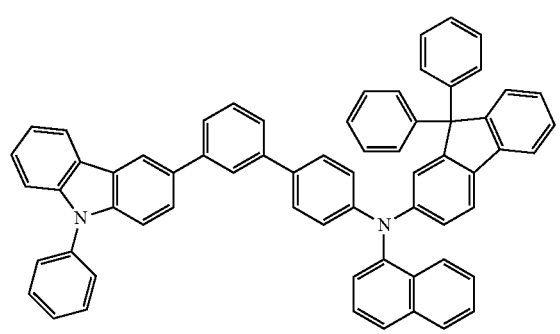
5
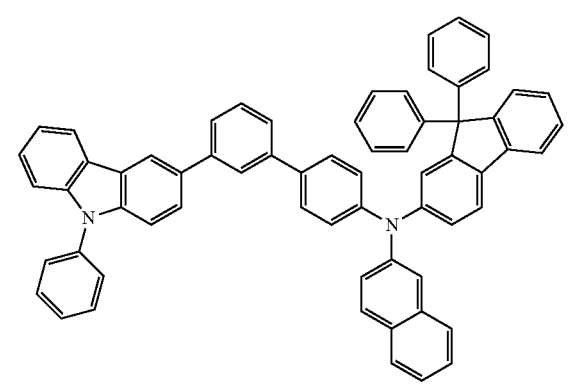
6

-continued
7
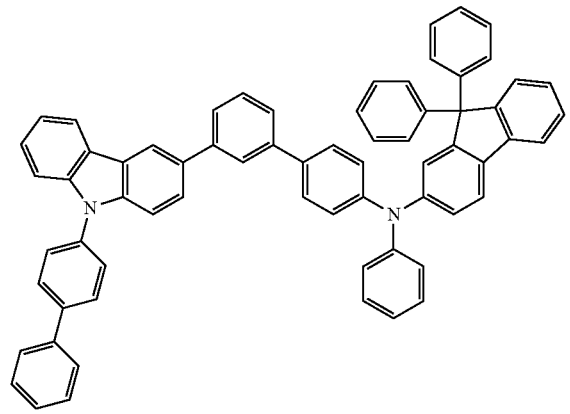
8
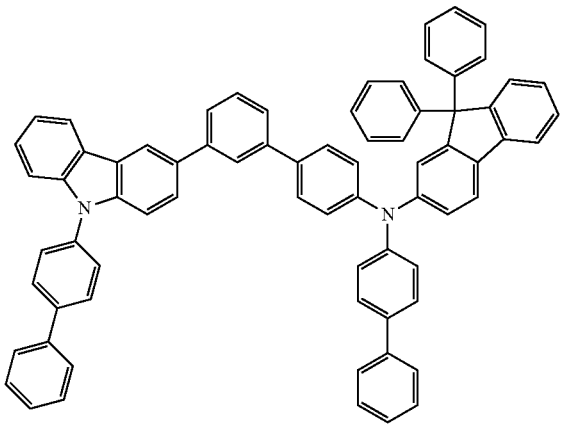
9
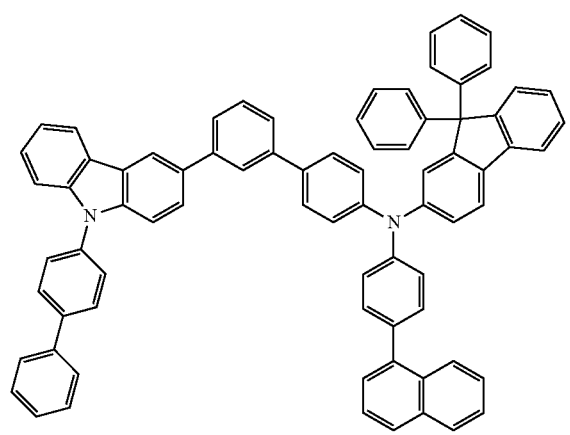
10
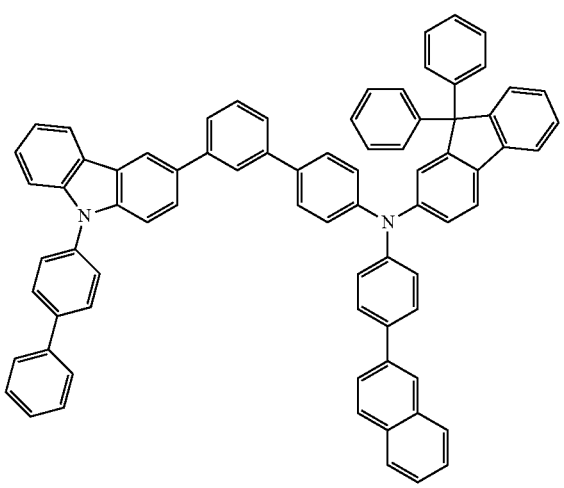
11
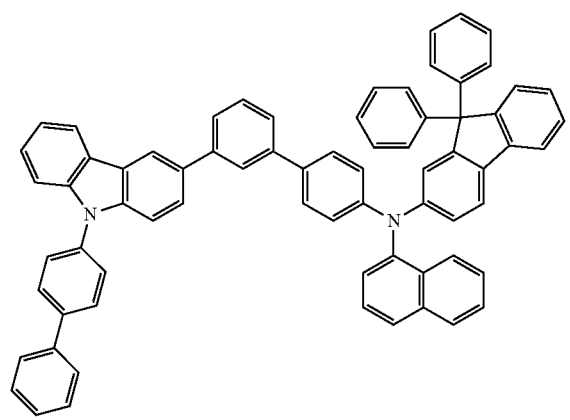
12
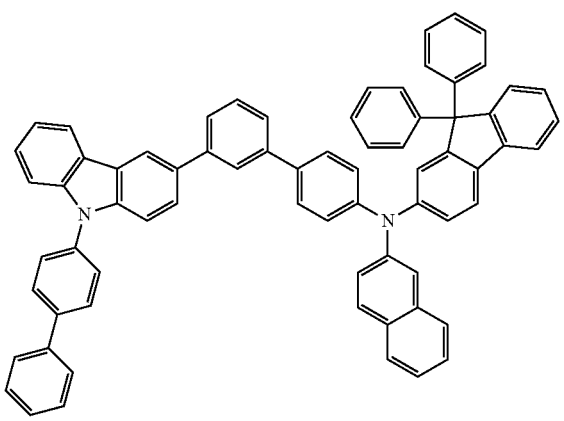

-continued
13
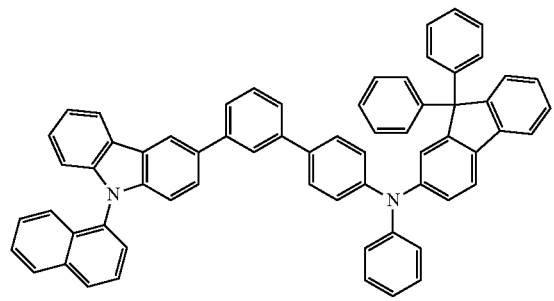
14
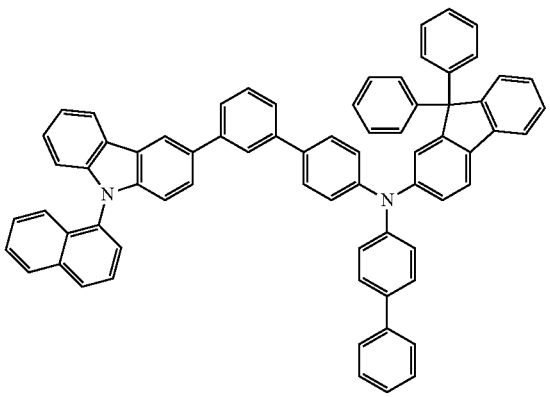
15
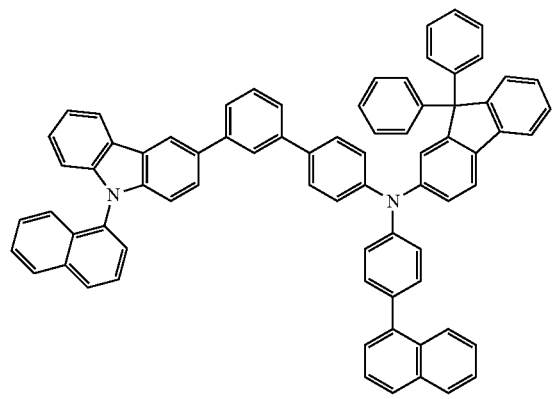
16
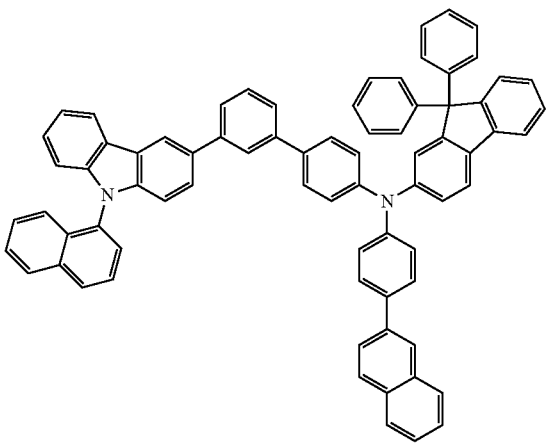
17
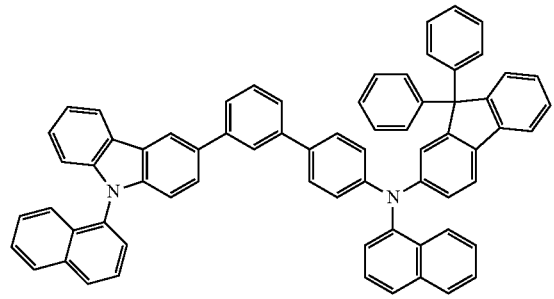
18
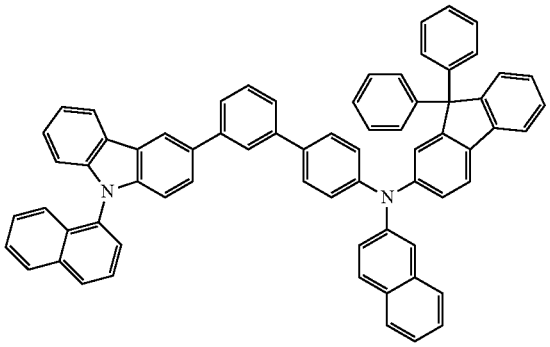
19
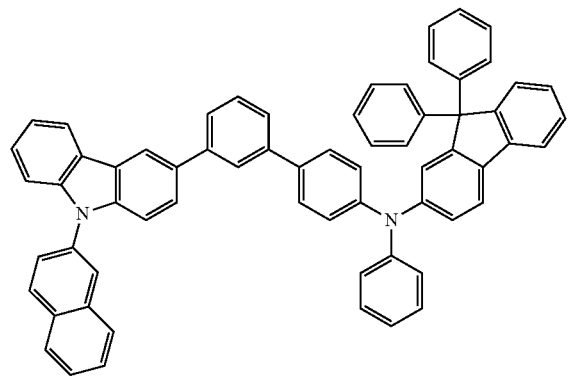
20
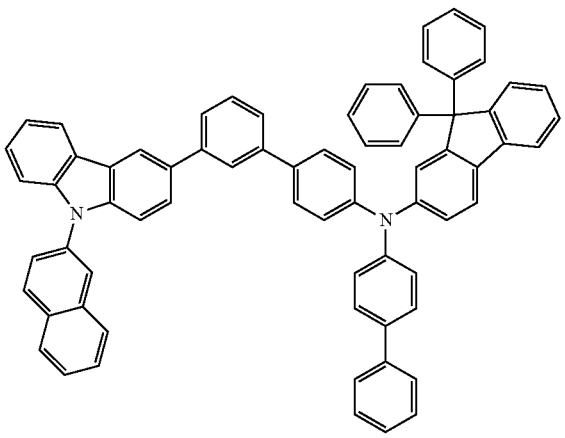

-continued
21
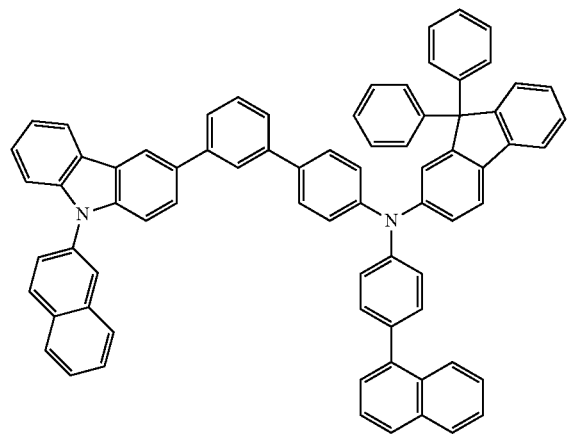
22
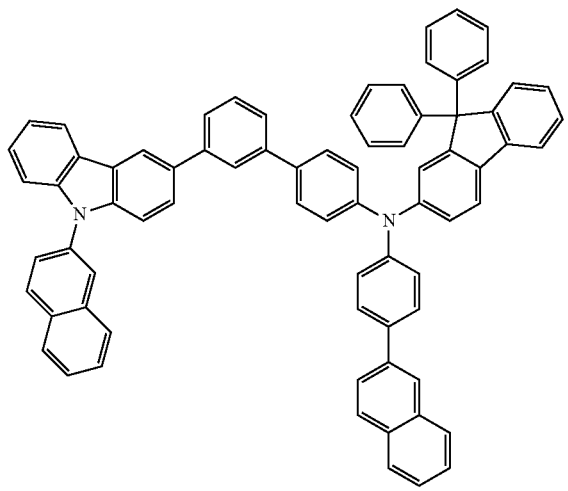
23
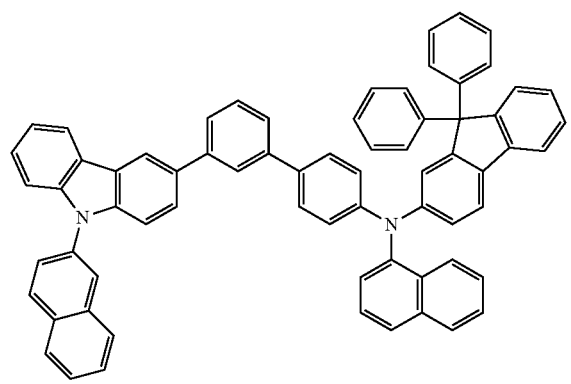
24
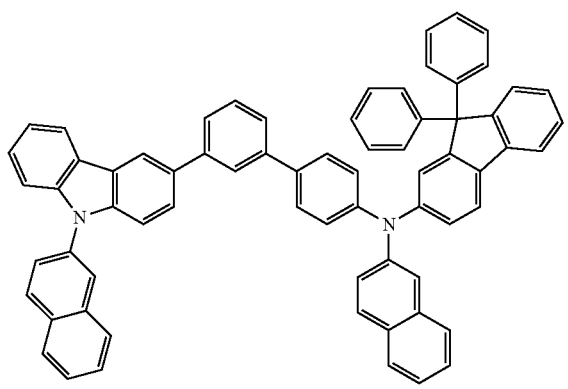
25
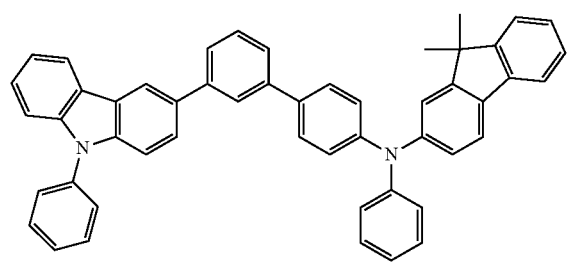
26
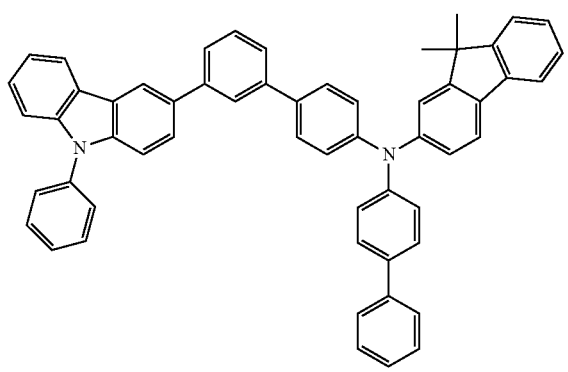

-continued
27
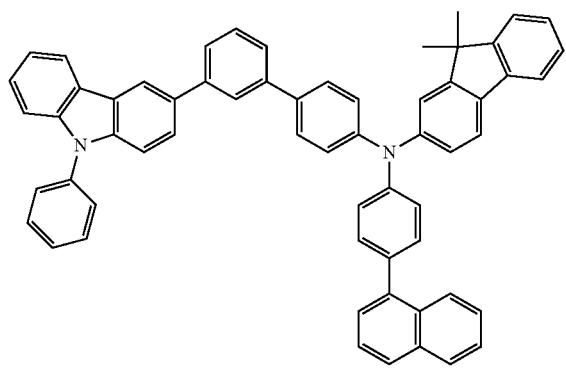
28
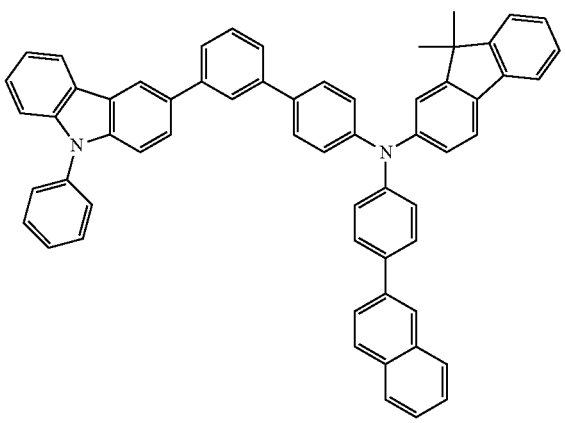
29
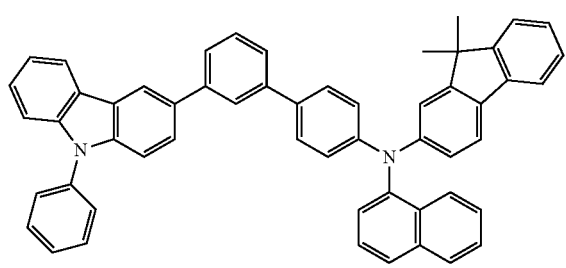
30
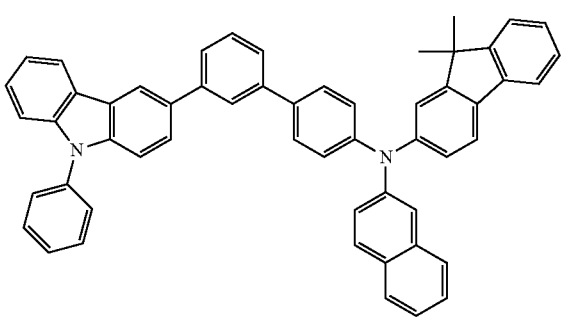
31
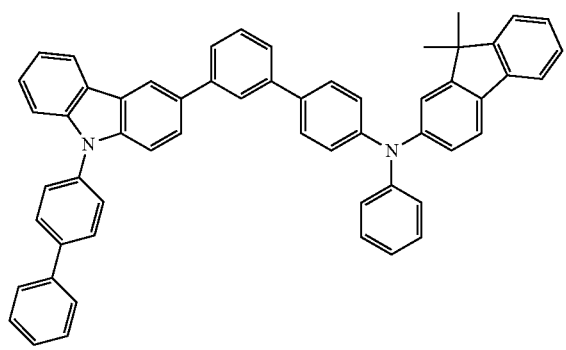
32
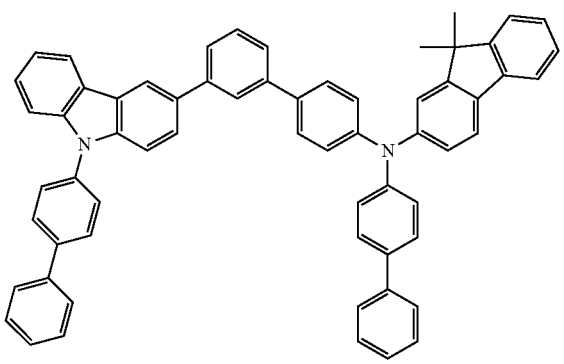
33
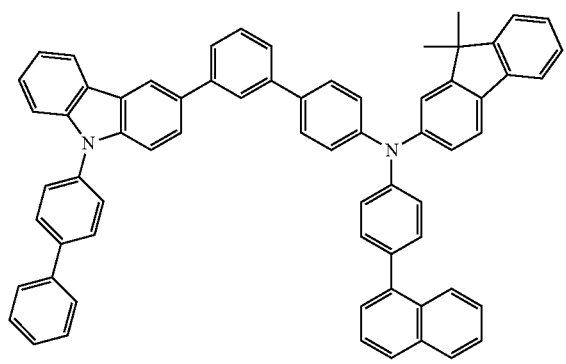
34
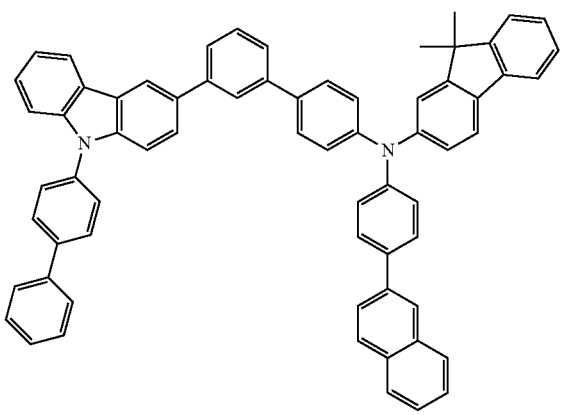

35
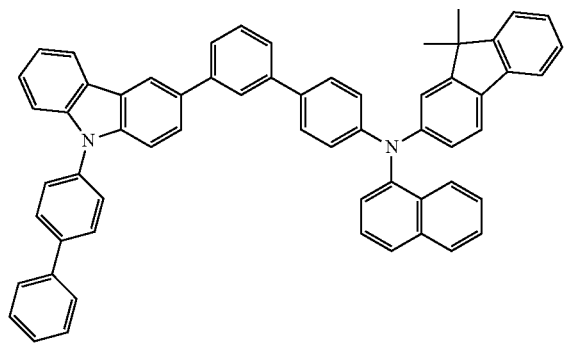
36
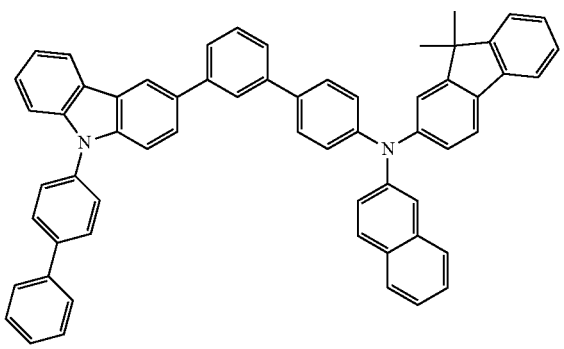
37
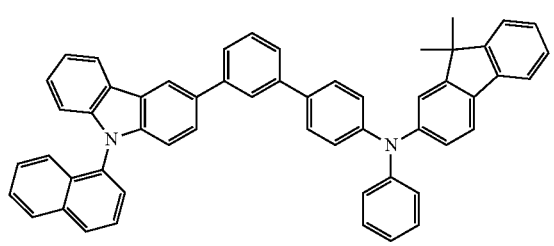
38
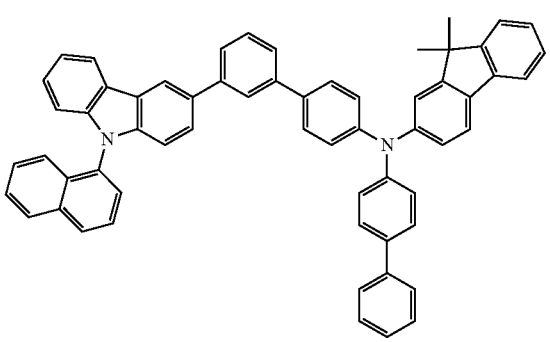
39
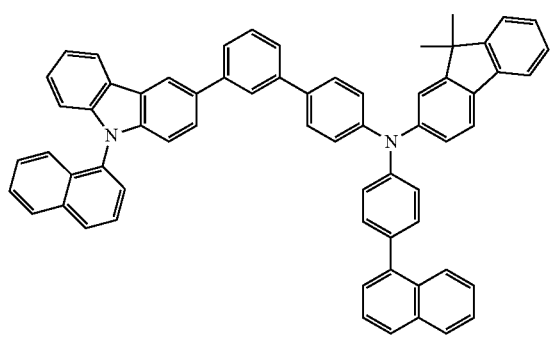
40
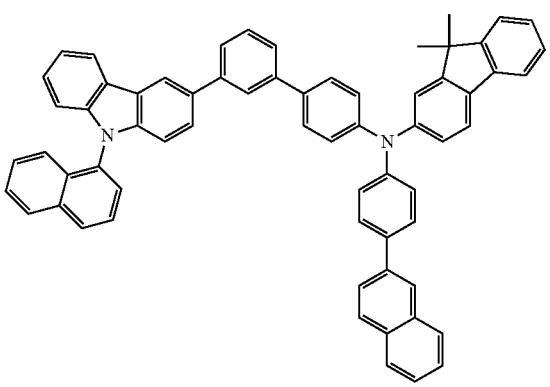
41
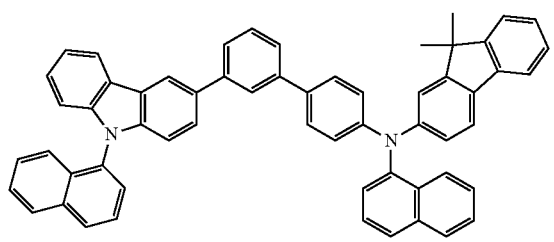
42
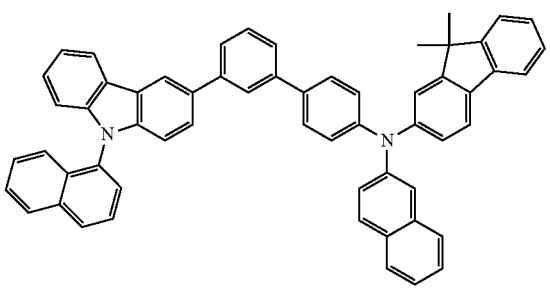

-continued
43
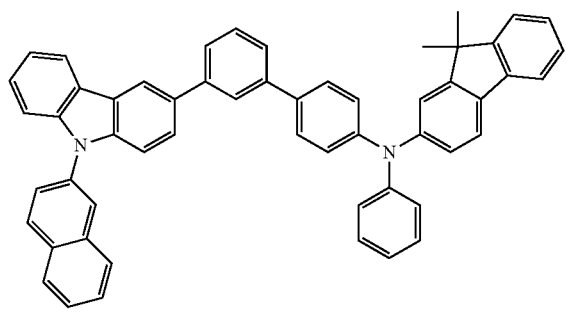
44
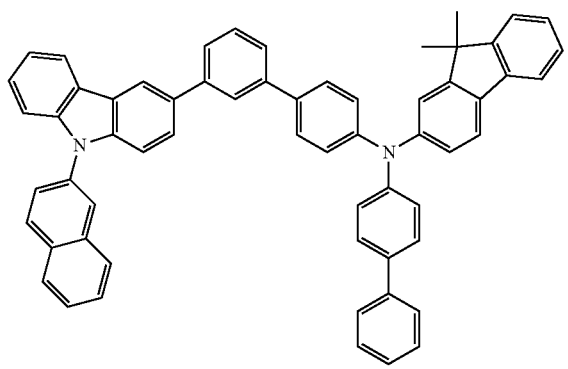
45
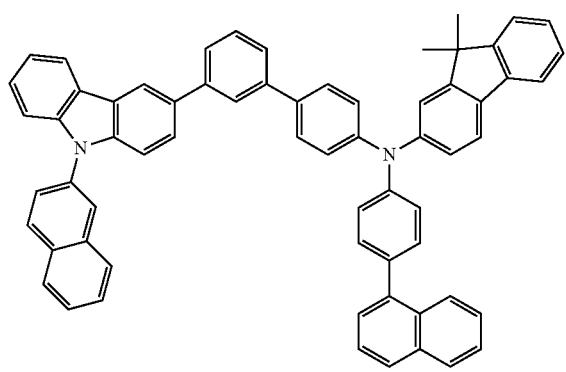
46
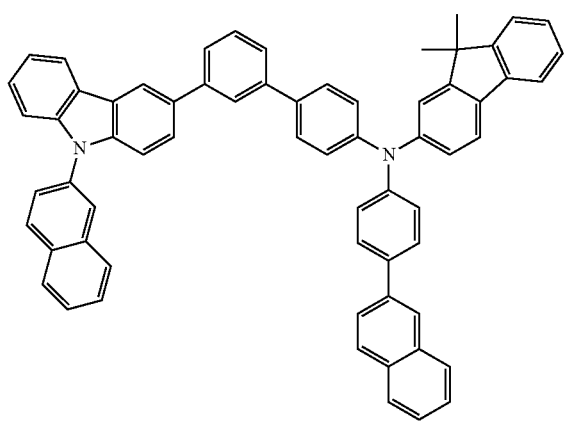
47
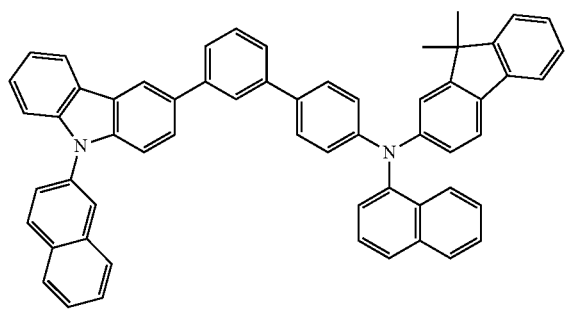
48
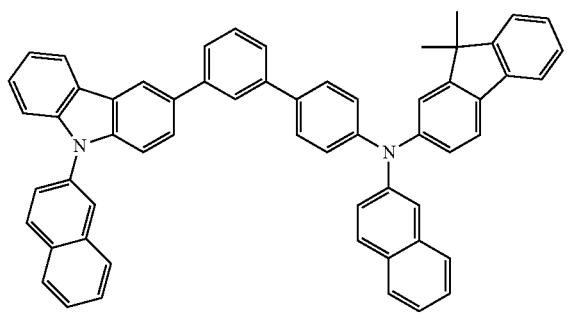
49
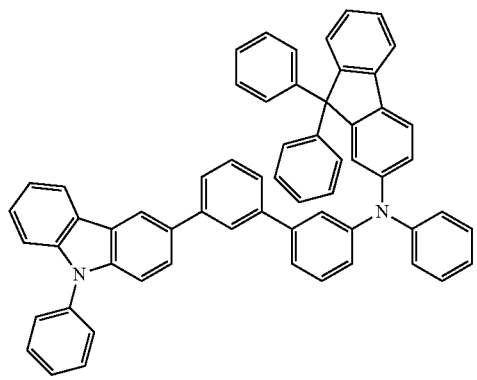
50
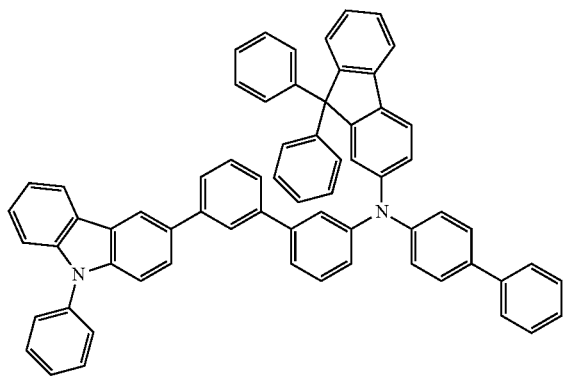

-continued
51
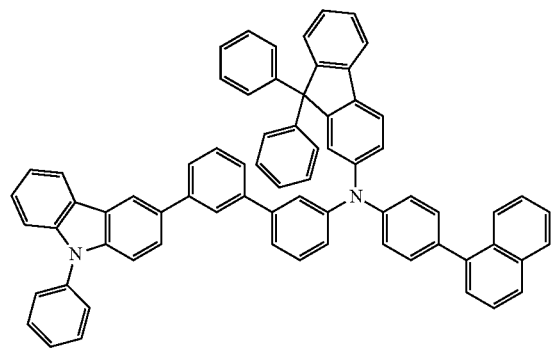
52
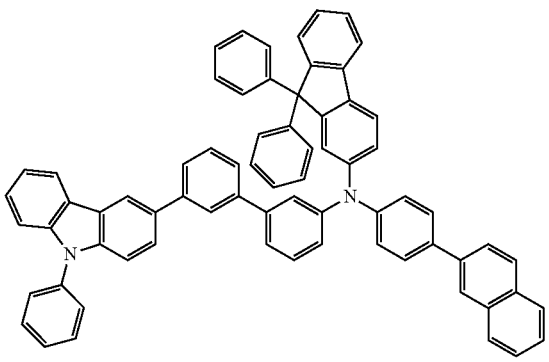
53
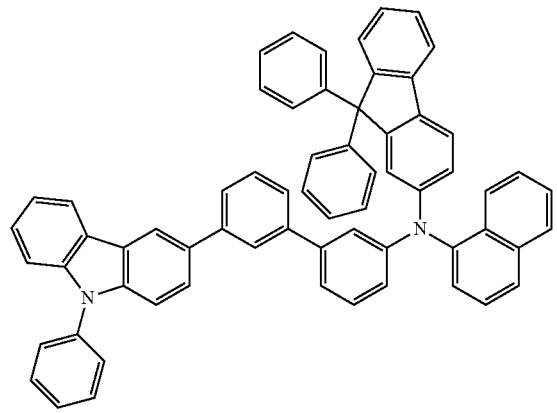
54
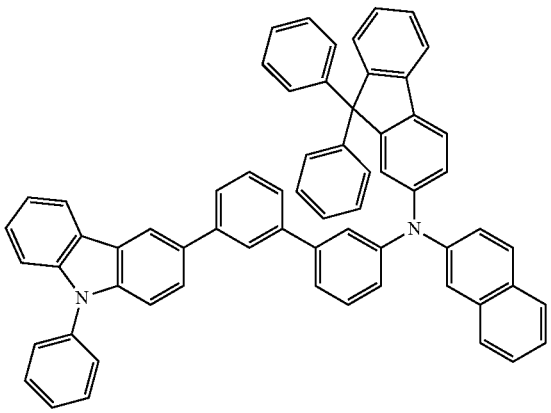
55
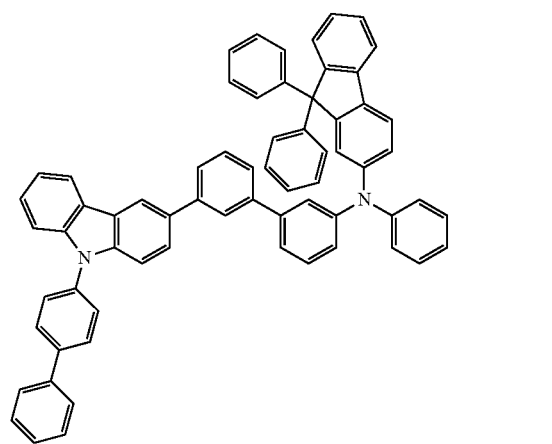
56
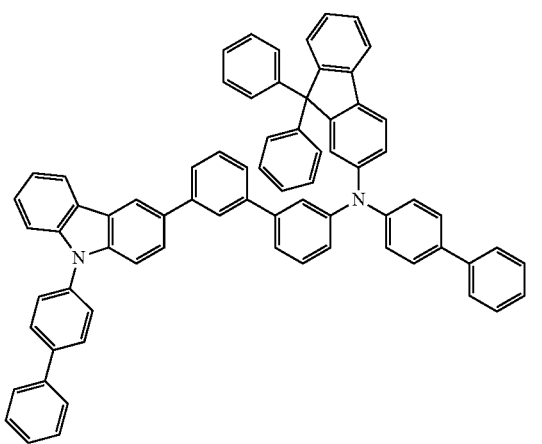
57
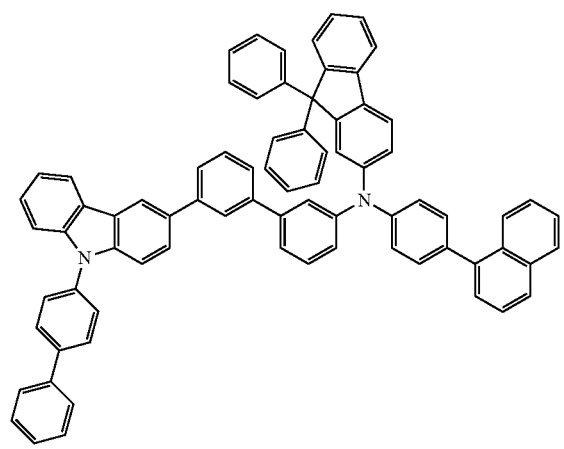
58
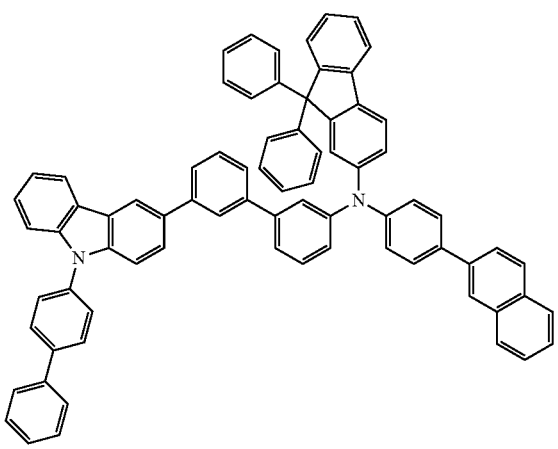

59
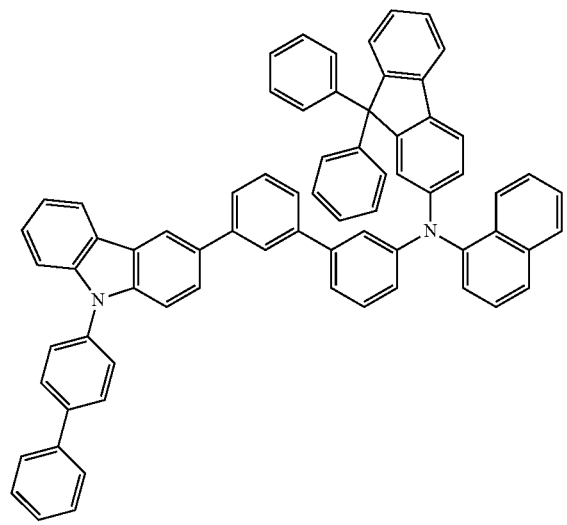
60
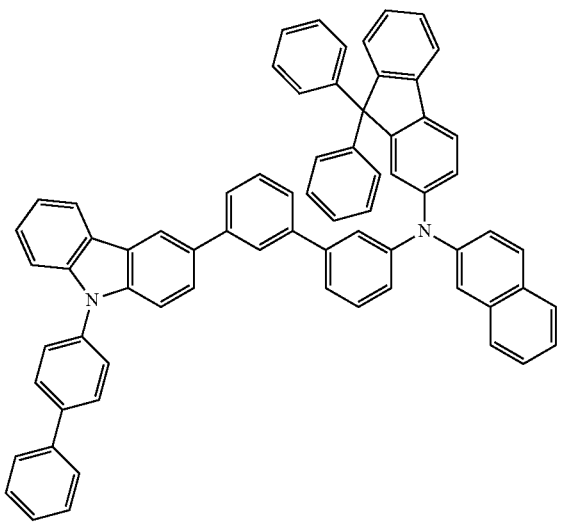
61
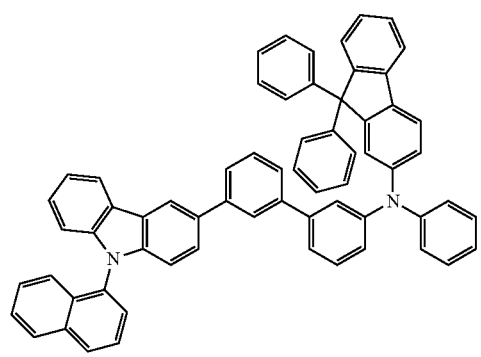
62
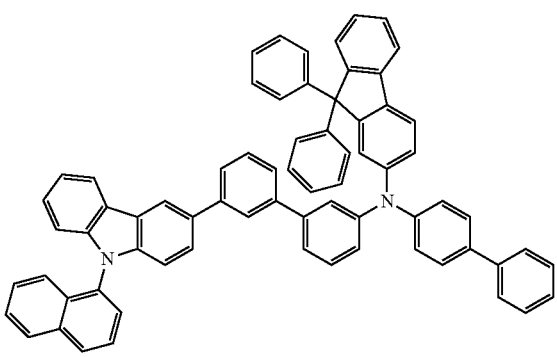
63
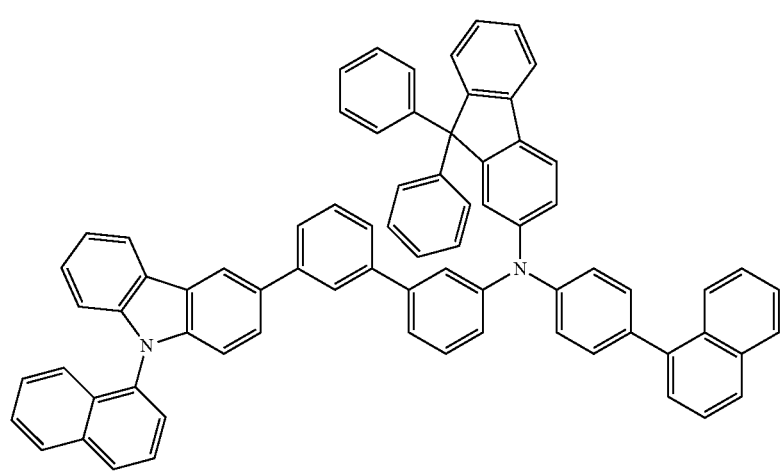

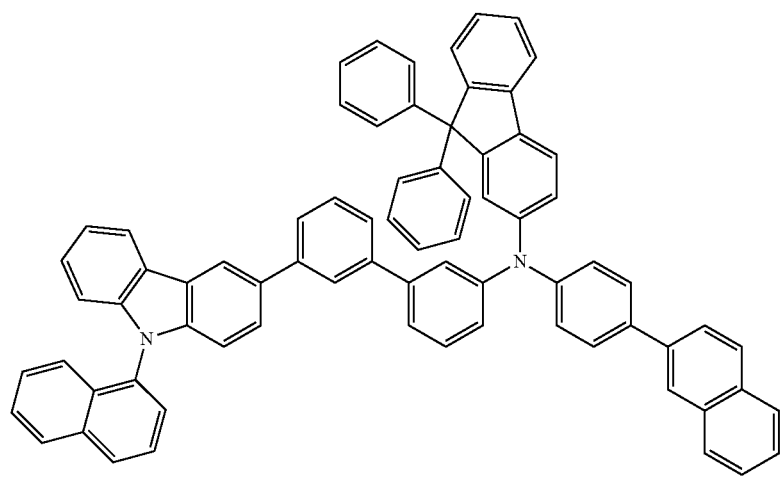
64
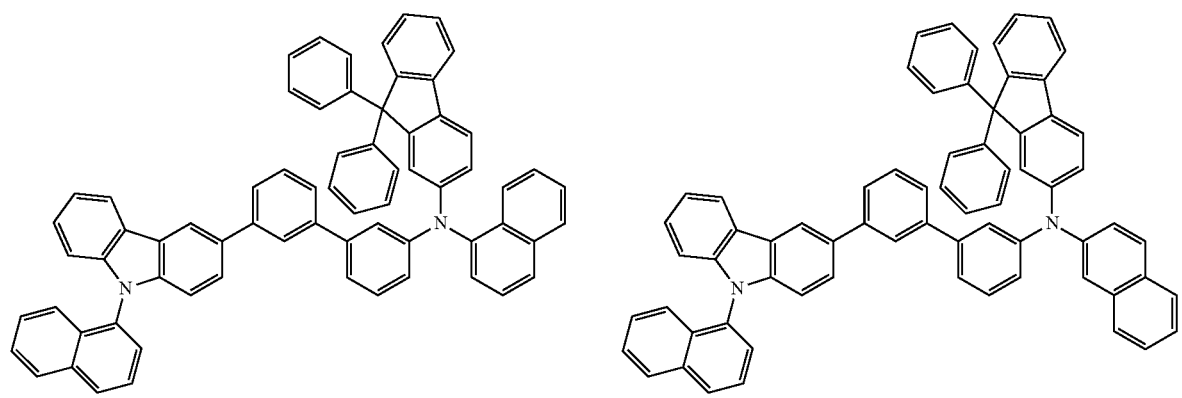
65
66
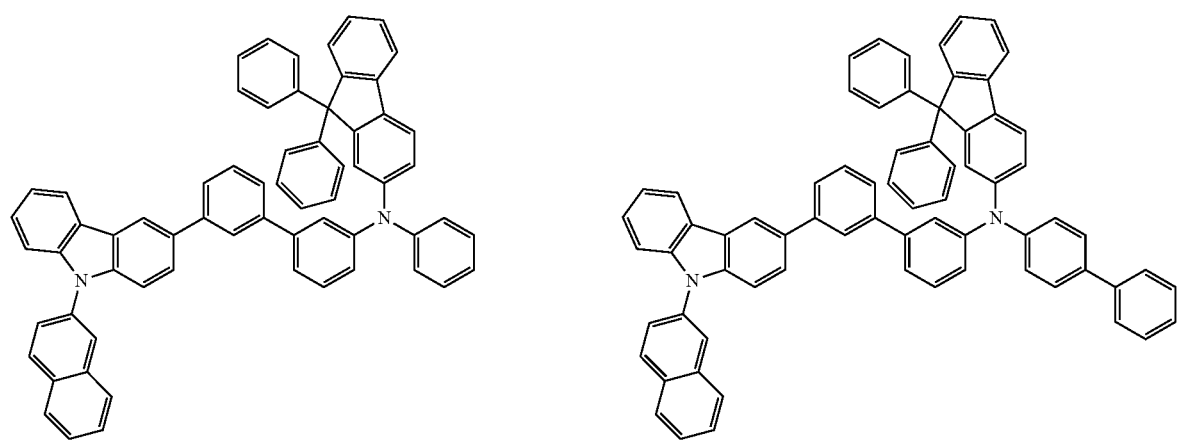
67
68

69
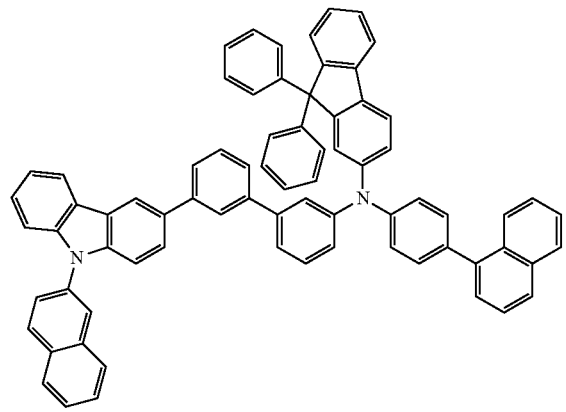
70
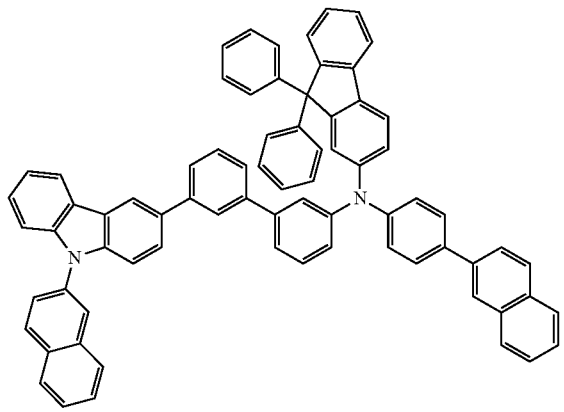
71
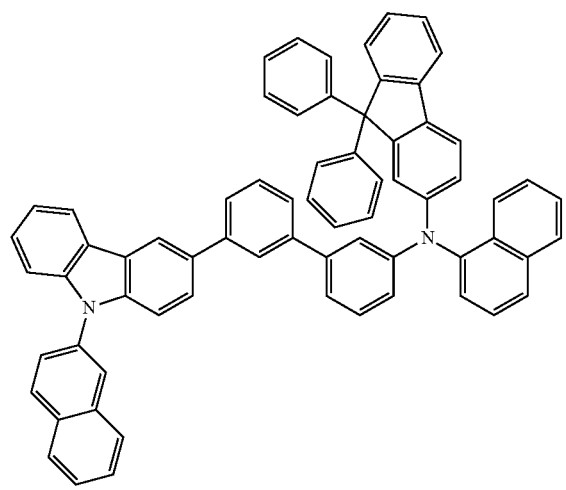
72
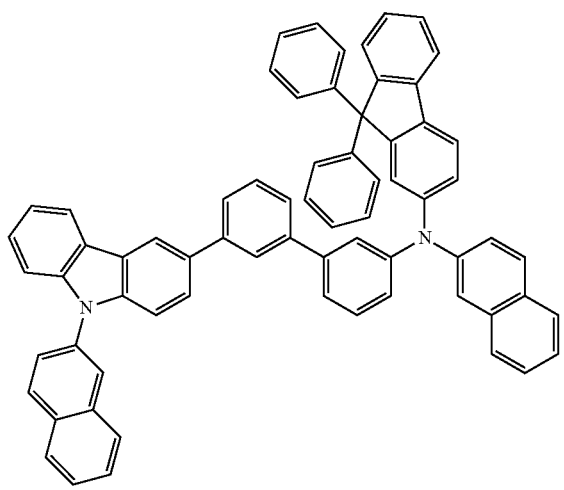
73
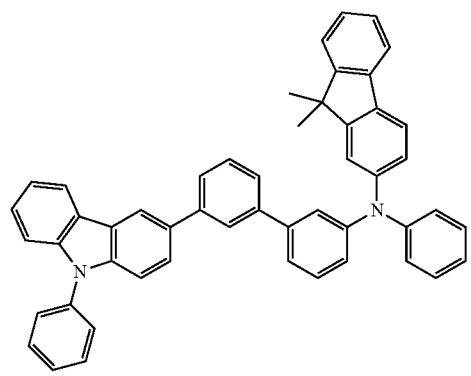
74
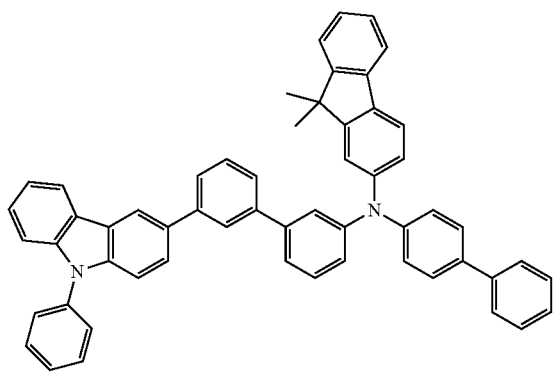
75
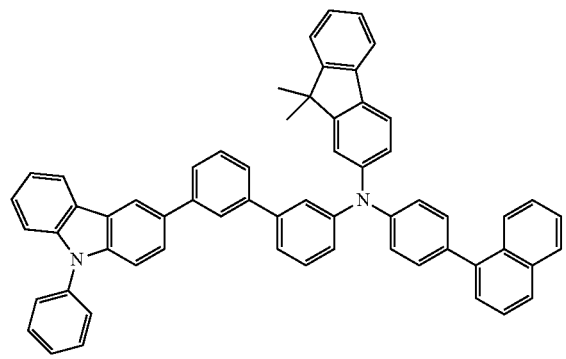
76
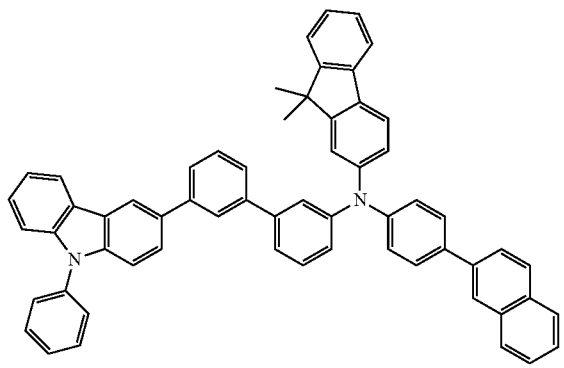

77
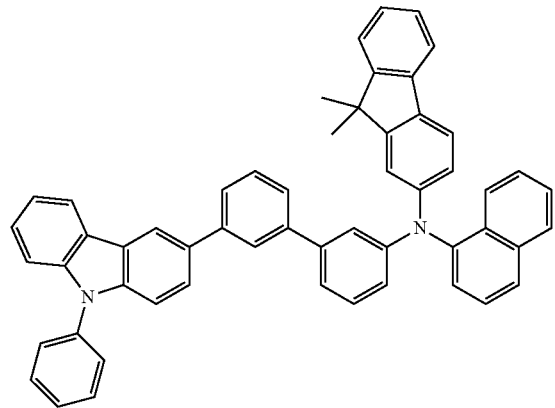
78
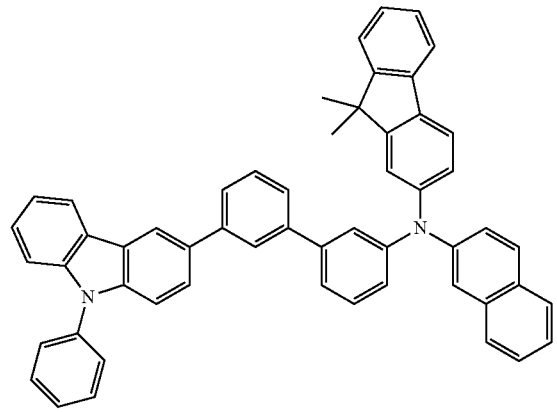
79
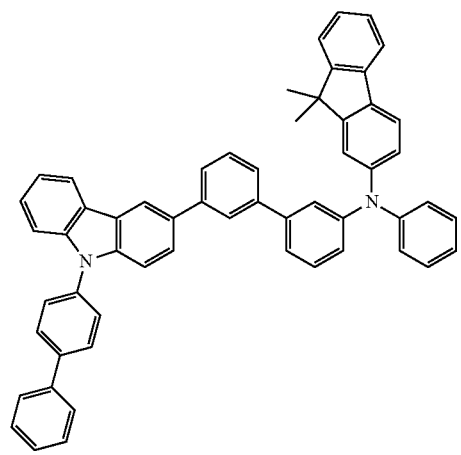
80
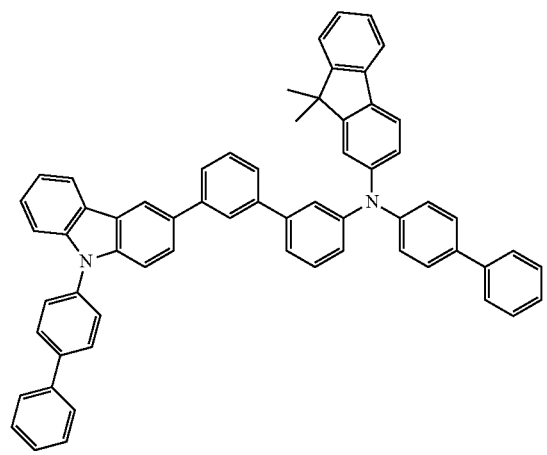
81
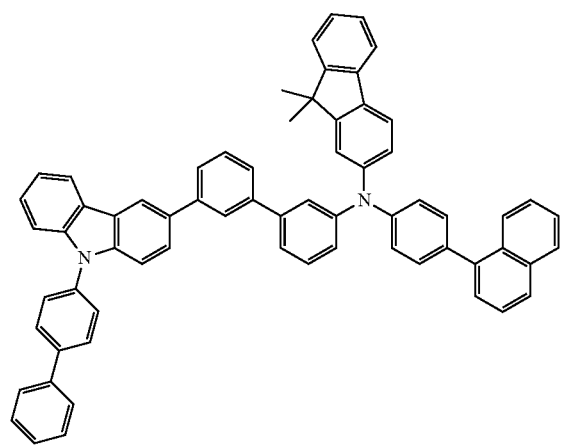
82
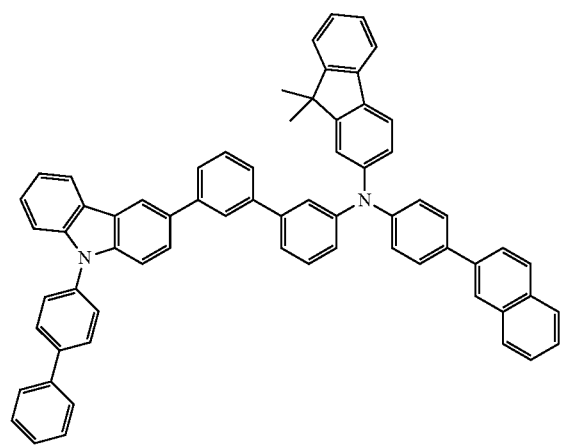

-continued
83
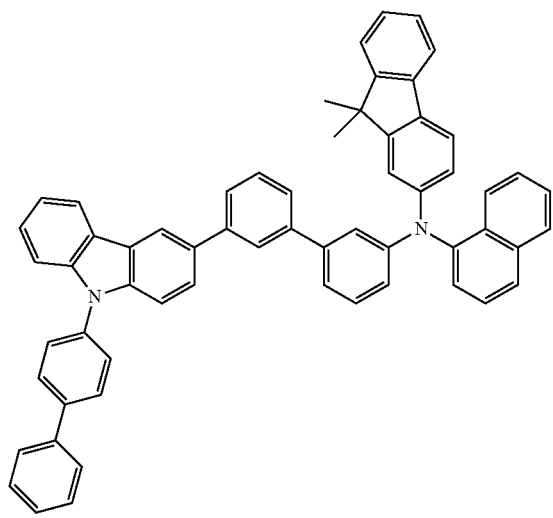
84
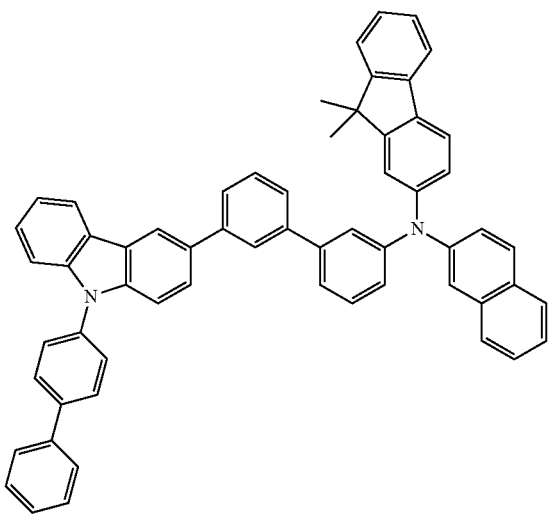
85
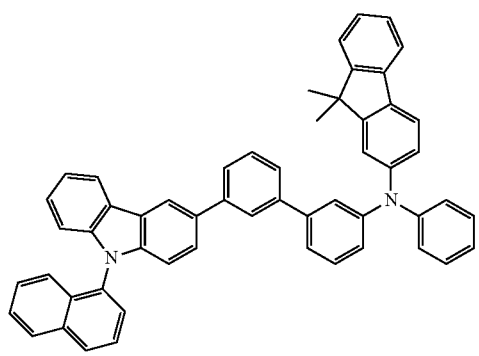
86
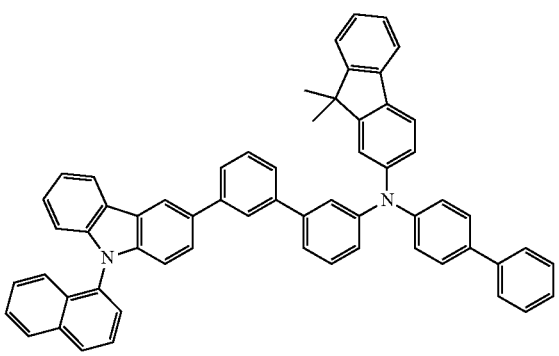
87
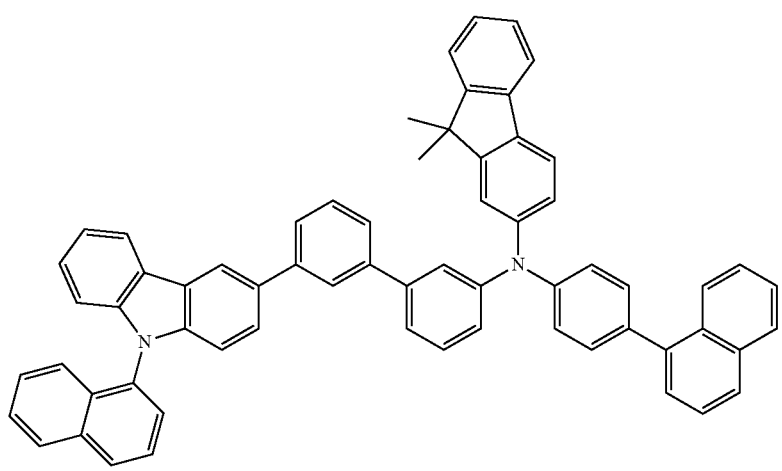

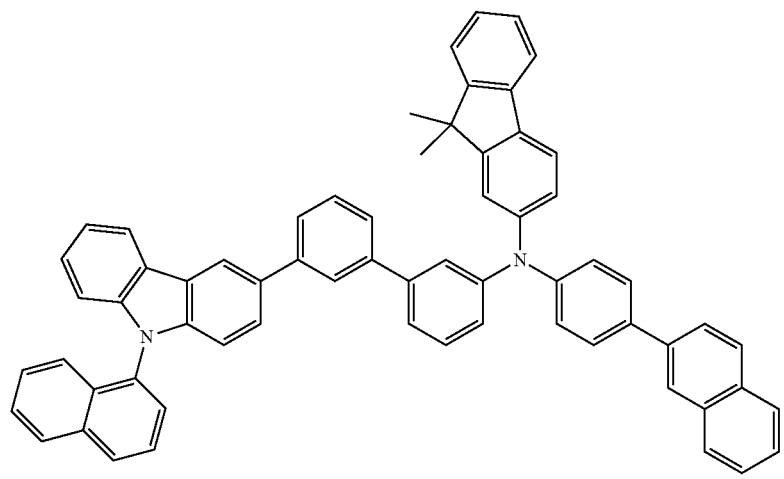
88
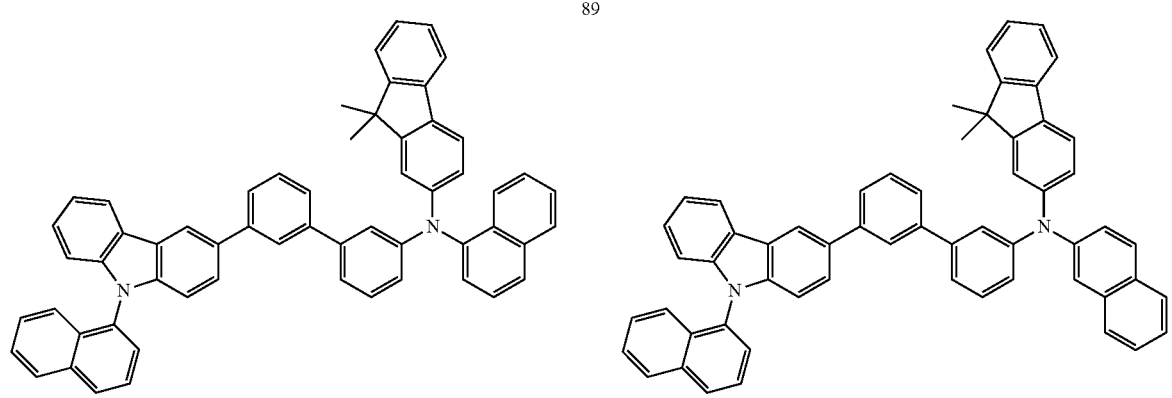
89   90
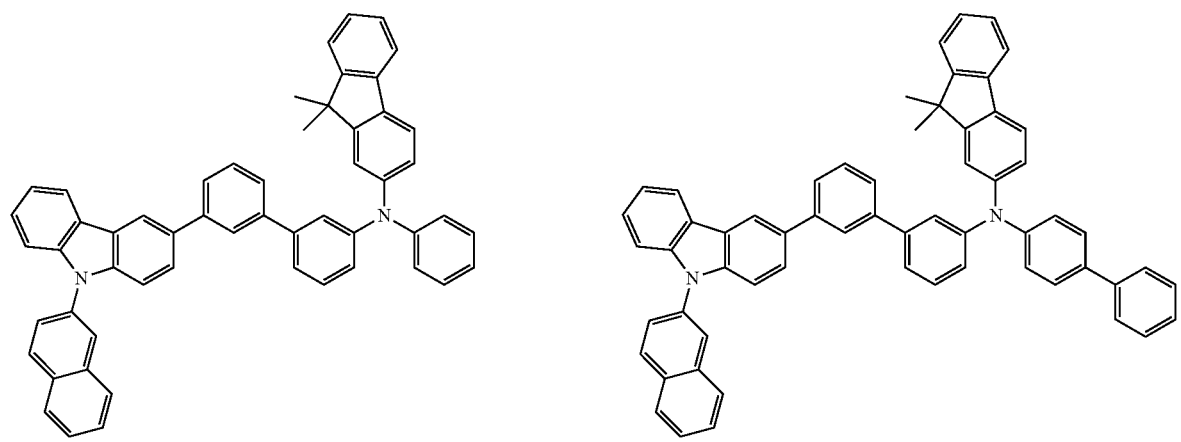
91   92

-continued

93

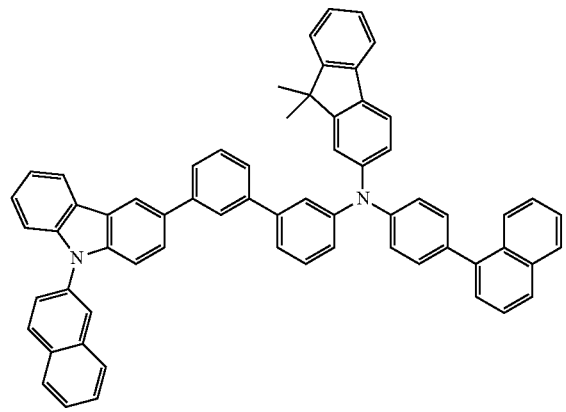

94

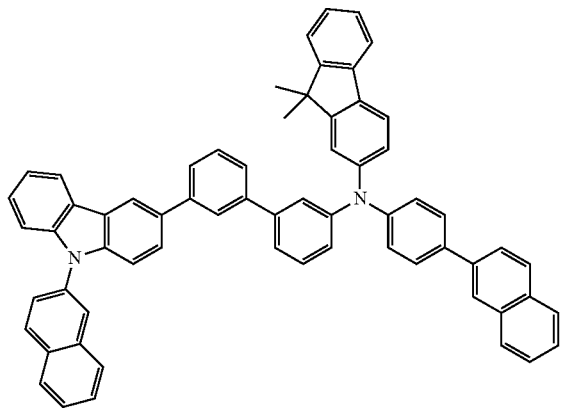

95

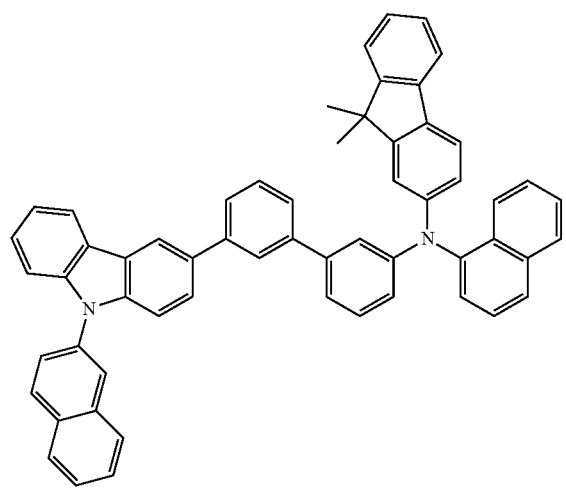

96

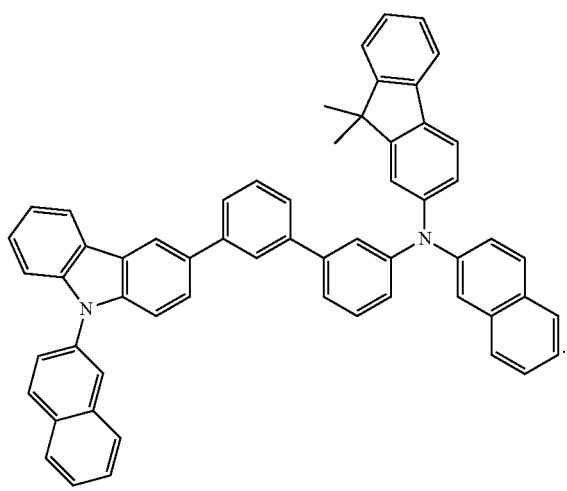

6. The organic light-emitting device as claimed in claim 1, wherein the first charge-generation material and the second charge-generation material are each independently selected from a quinone derivative, a metal oxide, or a compound containing a cyano group.

7. The organic light-emitting device as claimed in claim 1, wherein the first charge-generation material and the second charge-generation material are each independently selected from tetracyanoquinonedimethane (TCNQ), 2,3,5,6-tetrafluoro-tetracyano-1,4-benzoquinonedimethane (F4-TCNQ), or Compound 501:

<Compound 501>

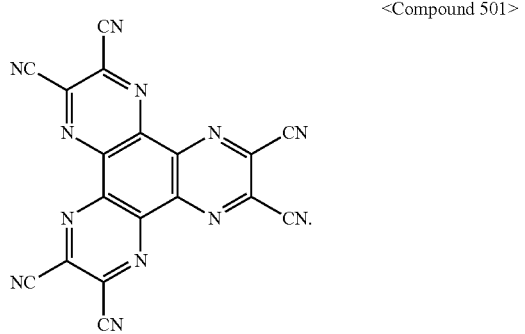 [SMILES: N#Cc1nc2c3nc(C#N)c(C#N)nc3c3nc(C#N)c(C#N)nc3c2nc1C#N]

8. The organic light-emitting device as claimed in claim 1, wherein the first compound is identical to the third compound, and the second compound is identical to the fourth compound.

9. The organic light-emitting device as claimed in claim 1, wherein the first compound is identical to the second compound, and the third compound is identical to the fourth compound.

10. The organic light-emitting device as claimed in claim 1, wherein an amount of the first charge-generation material is in a range of about 0.01 to about 3 wt % based on 100 wt % of the first hole transport layer.

11. The organic light-emitting device as claimed in claim 1, wherein an amount of the second charge-generation material is in a range of about 0.01 to about 3 wt % based on 100 wt % of the third hole transport layer.

12. The organic light-emitting device as claimed in claim 1, wherein a thickness of each of the first hole transport layer and the third hole transport layer is in a range of about 5 nm to about 30 nm.

13. The organic light-emitting device as claimed in claim 1, wherein a thickness of each of the second hole transport layer and the fourth hole transport layer is in a range of about 60 nm to about 100 nm.

14. The organic light-emitting device as claimed in claim 1, further comprising a buffer layer disposed between the emission layer and the fourth hole transport layer.

15. The organic light-emitting device as claimed in claim 14, wherein the buffer layer includes at least one compound represented by Formula 1 or 2.

16. The organic light-emitting device as claimed in claim 14, wherein a thickness of the buffer layer is in a range of 1 nm to 20 nm.

17. The organic light-emitting device as claimed in claim 1, wherein the first hole transport layer contacts the second hole transport layer.

18. The organic light-emitting device as claimed in claim 1, wherein the third hole transport layer contacts the fourth hole transport layer.

19. The organic light-emitting device as claimed in claim 1, further comprising at least one layer disposed between the emission layer and the second electrode and selected from a hole blocking layer, an electron transport layer, an electron injection layer, and a functional layer having an electron transport capability and an electron injection capability.

20. An organic light-emitting device, comprising:
a first electrode;
a second electrode facing the first electrode;
an emission layer disposed between the first electrode and the second electrode;
a first hole transport layer that is disposed between the emission layer and the first electrode and includes a first compound and a first charge-generation material;
a second hole transport layer that is disposed between the emission layer and the first hole transport layer and includes a second compound;
a third hole transport layer that is disposed between the emission layer and the second hole transport layer and includes a third compound and a second charge-generation material; and
a fourth hole transport layer that is disposed between the emission layer and the third hole transport layer and includes a fourth compound;
wherein the first compound, the second compound, the third compound, and the fourth compound are each independently a compound represented by Formula 1A or 2A:

<Formula 1A>

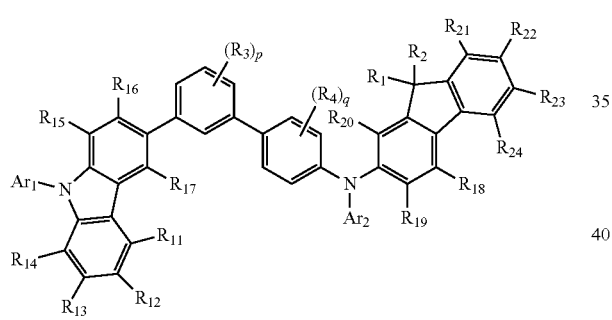

<Formula 2A>

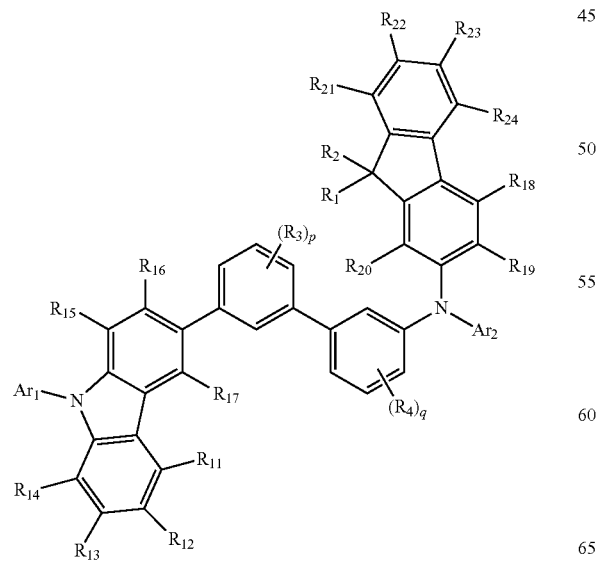

wherein in Formulae 1A and 2A,
$Ar_1$ and $Ar_2$ are each independently represented by one of Formulae 3-1 to 3-20:

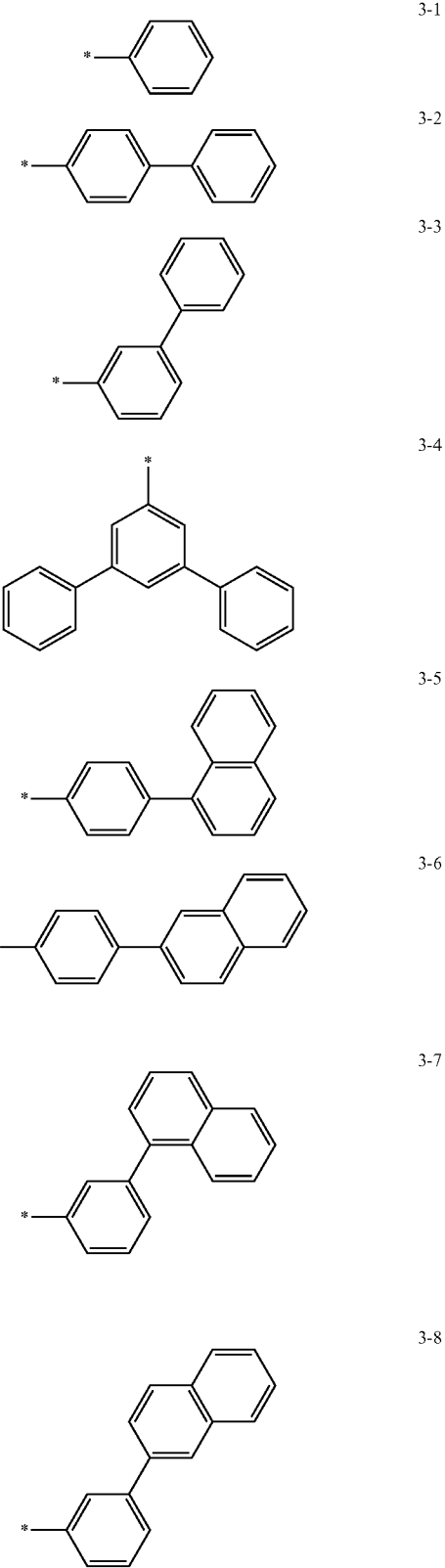

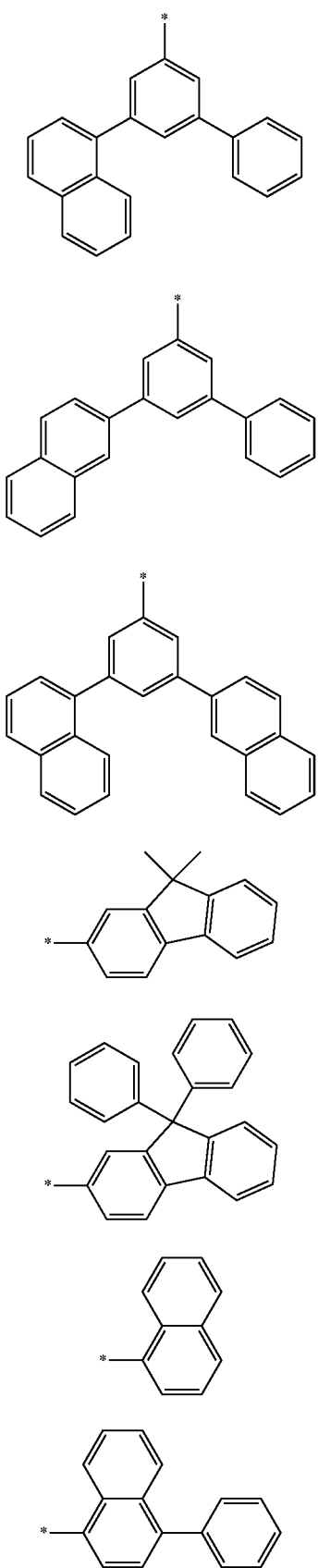
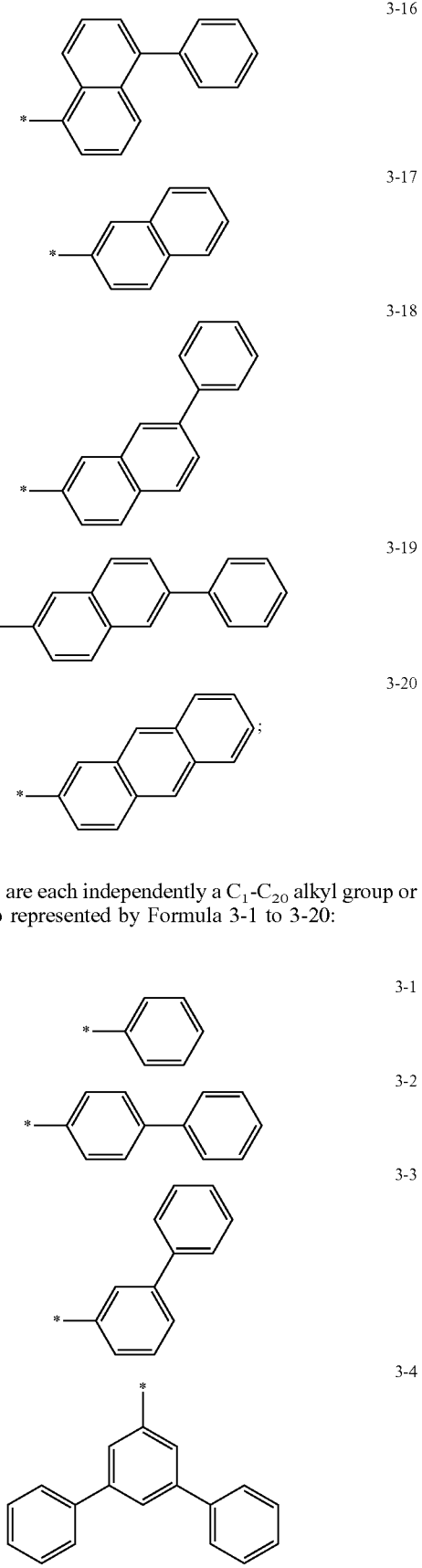
$R_1$ and $R_2$ are each independently a $C_1$-$C_{20}$ alkyl group or a group represented by Formula 3-1 to 3-20:

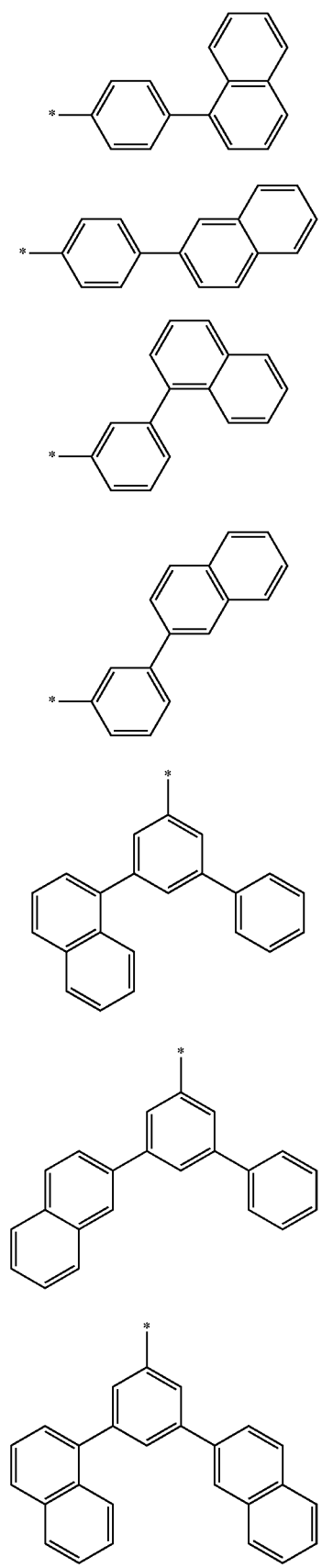
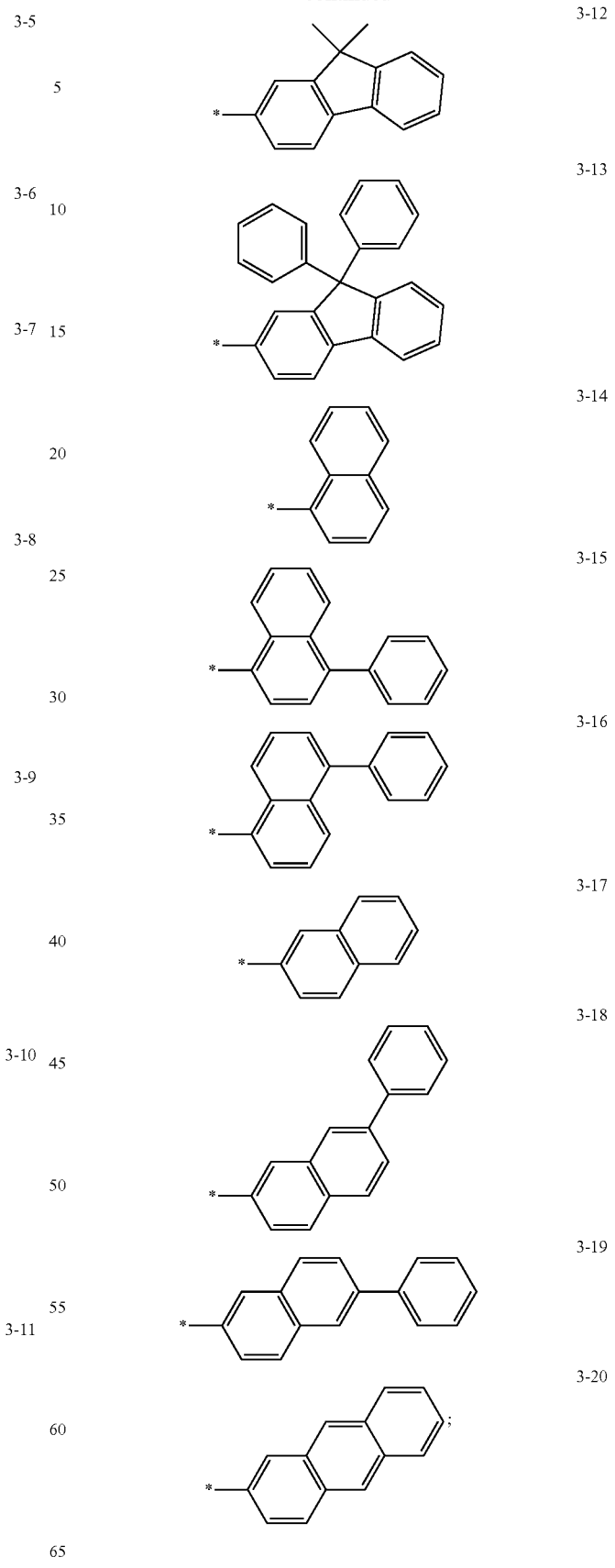
$R_3$, $R_4$ and $R_{11}$ to $R_{24}$ are each independently a hydrogen, a deuterium, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, or a group represented by Formulae 3-1 to 3-20:
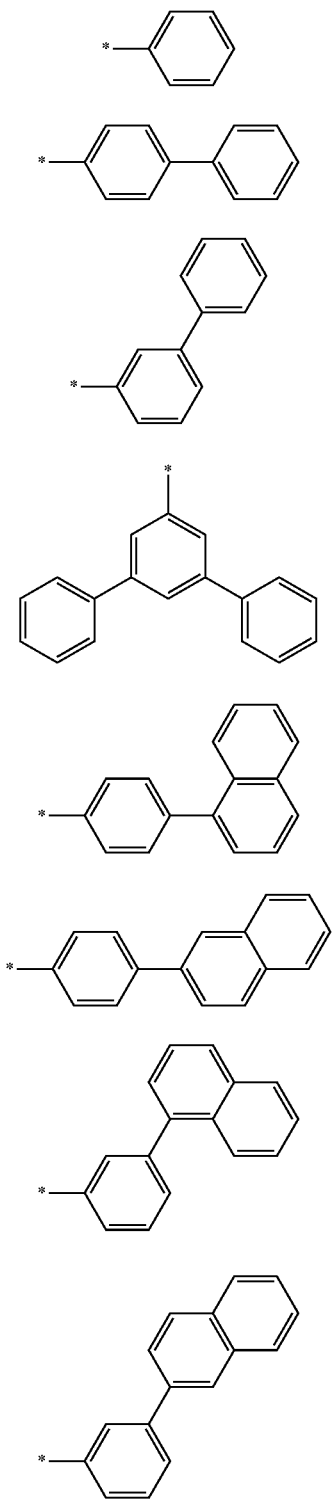
-continued
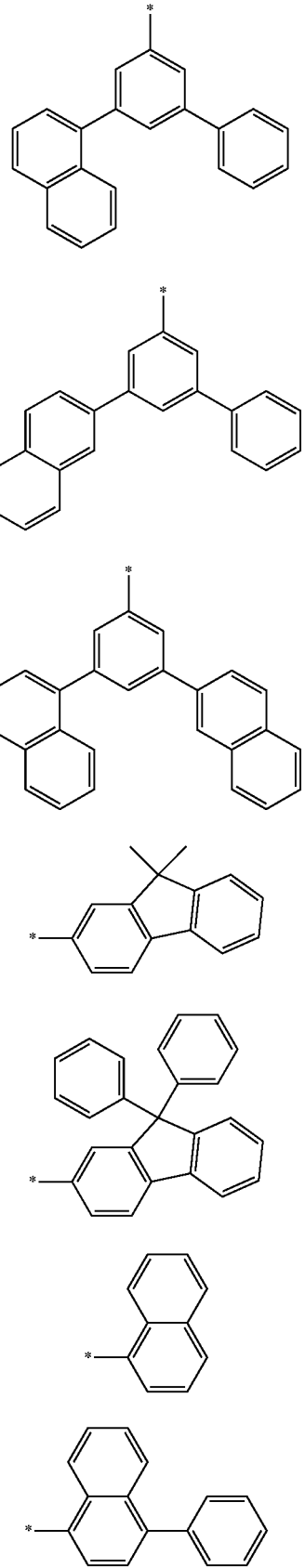

3-16 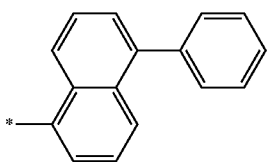
3-17 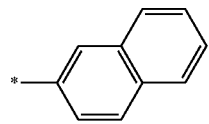
3-18 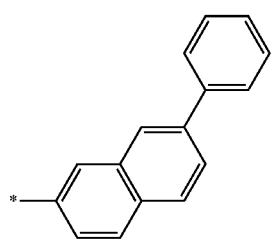
3-19 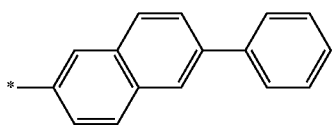
3-20 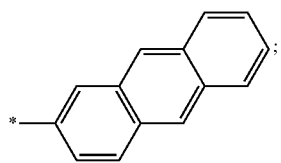
and
p and q are each independently an integer of 1 to 4.
* * * * *